US007977321B2

(12) United States Patent
Kania et al.

(10) Patent No.: US 7,977,321 B2
(45) Date of Patent: Jul. 12, 2011

(54) SMALL INTERFERING RNAS TARGETING FELINE HERPES VIRUS

(75) Inventors: Stephen A. Kania, Powell, TN (US); Rebecca P. Wilkes, Maryville, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 117 days.

(21) Appl. No.: 12/370,213

(22) Filed: Feb. 12, 2009

(65) Prior Publication Data

US 2009/0203138 A1    Aug. 13, 2009

Related U.S. Application Data

(60) Provisional application No. 61/027,972, filed on Feb. 12, 2008.

(51) Int. Cl.
*A61K 31/70* (2006.01)
*C07H 21/02* (2006.01)
*C07H 21/04* (2006.01)
*C12Q 1/68* (2006.01)

(52) U.S. Cl. .......... 514/44 A; 435/6; 435/375; 536/23.1; 536/24.1; 536/24.5

(58) Field of Classification Search .................. None
See application file for complete search history.

(56) References Cited

U.S. PATENT DOCUMENTS

2004/0259247 A1* 12/2004 Tuschl et al. .................. 435/375

OTHER PUBLICATIONS

Barton, G. and Medzhitov, R., "Retroviral delivery of small interfering RNA into primary cells", *Proc Natl Aced Sci*, Nov. 12, 2002, pp. 14943-14945, vol. 99, No. 23.
Bhuyan, P. et al., "Short Interfering RNA-Mediated Inhibition of Herpes Simplex Virus Type 1 Gene Expression and Function during Infection of Human Keratinocytes", *Journal of Virology*, Oct. 2004, pp. 10276-10281, vol. 78, No. 19, American Society for Microbiology.
Bitko, V. et al., "Inhibition of respiratory viruses by nasally administered siRNA", *Nature Medicine*, Jan. 2005, pp. 50-55, vol. 11, No. 1, Nature Publishing Group.
Devroe, E. and Silver, P., "Retrovirus-delivered siRNA", *BMC Biotechnology*, 2002, pp. 1-5, vol. 2, No. 15.
Fattal, E. et al., "Biodegradable polyalkylcyanoacrylate nanoparticles for the delivery of oligonucleotides", *Journal of Controlled Release*, 1998, pp. 137-143, vol. 53, Elsevier Science B.V.
Kim, D. and Rossi, J., "Strategies for silencing human disease using RNA interference", *Nature Reviews Genetics*, Mar. 2007, pp. 173-184, vol. 8, Nature Publishing Group.

Lambert, G. et al., "Nanoparticulate systems for the delivery of antisense oligonucleotides", *Advanced Drug Delivery Reviews*, 2001, pp. 99-112, vol. 47, Elsevier Science B.V.
Li, B. et al., "Using siRNA in prophylactic and therapeutic regimens against SARS coronavirus in Rhesus macaque", *Nature Medicine*, Sep. 2005, pp. 944-951, vol. 11, No. 9, Nature Publishing Group.
Morris, M. et al., "Translocating peptides and proteins and their use for gene delivery", *Current Opinion in Biotechnology*, 2000, pp. 461-466, vol. 11, Elsevier Science Ltd.
Nasisse, M. et al., "Detection of feline herpesvirus 1 DNA in corneas of cats with eosinophilic keratitis or corneal sequestration", *Am J Vet Res*, Jul. 1998, pp. 856-858, vol. 59, No. 7.
Nasisse, M. et al., "Experimental Ocular Herpesvirus Infection in the Cat", *Investigative Ophthalmology & Visual Science*, Aug. 1989, pp. 1758-1768, vol. 30, No. 8, Association for Research in Vision and Ophthalmology.
Palliser, D. et al., "An siRNA-based microbicide protects mice from lethal herpes simplex virus 2 infection", *Nature*, Jan. 5, 2006, pp. 89-94, vol. 439, Nature Publishing Group.
Paul, C. et al., "Effective expression of small interfering RNA in human cells", *Nature Biotechnology*, May 2002, pp. 505-508, vol. 29, Nature Publishing Group.
Shuey, D. et al., "RNAi: gene-silencing in therapeutic intervention", *Drug Discovery Today*, Oct. 2002, pp. 1040-1046, vol. 7, No. 20, Elsevier Science Ltd.
Spagnou, S. et al., "Lipidic Carriers of siRNA: Differences in the Formulation, Cellular Uptake, and Delivery with Plasmid DNA", *Biochemistry*, 2004, pp. 13348-13356, vol. 43, No. 42, American Chemical Society.
Sui, G. et al., "A DNA vector-based RNAi technology to suppress gene expression in mammalian cells", *Proc Natl Aced Sci*, Apr. 16, 2002, pp. 5515-5520, vol. 99, No. 8.
GenBank Accession No. AF079125.1, Mar. 16, 2000, pp. 1-2.
GenBank Accession No. AJ224971, Mar. 11, 1998, pp. 1-4.
GenBank Accession No. D30767.1, Feb. 17, 2007, pp. 1-3.
Wilkes, R. and Kania, S., "Can an ancient defense mechanism against viral infections in yeast, plants, and mammals help prevent or cure cate flu?" *Winn News*, Winter 2005, pp. 1-4.
Wilkes, R. and Kania, S., "RNA interference of the glycoprotein-D and DNA polymerase genes of feline herpesvirus by synthetic siRNAs", *The Winn Feline Foundation for the Health and Well-Being of All Cats*, 2005 Grant Awards, George and Phyllis Miller Trust.
Wilkes, R. et al. "Evaluation of the effects of small interfering RNAs on in vitro replication of feline herepsvirus-1," *AJVR*, Jun. 2010, pp. 655-663, vol. 71, No. 6.
Wilkes, R. P. et al. "Use of interfering RNAs targeted against feline herpesvirus 1 glycoprotein D for inhibition of feline herpesvirus 1 infection of feline kidney cells" *AJVR*, Aug. 2009, pp. 1018-1025, vol. 70, No. 98.

* cited by examiner

*Primary Examiner* — Sean R McGarry
(74) *Attorney, Agent, or Firm* — Saliwanchik, Lloyd & Eisenschenk

(57) ABSTRACT

The present application provides polynucleotides, compositions thereof and methods of treating feline herpes virus infections. In certain embodiments, the polynucleotides and compositions thereof can be used to reduce replication of feline herpes simplex virus 1 (FHV-1) in vivo and/or in vitro.

18 Claims, 25 Drawing Sheets

SMALL INTERFERING RNAS TARGETING FELINE HERPES VIRUS

CROSS REFERENCE TO RELATED APPLICATION

This application claims the benefit of U.S. Provisional Application 61/027,972, filed Feb. 12, 2008, which is hereby incorporated by reference in its entirety, including all figures, tables, amino acid sequences and polynucleotide sequences.

BACKGROUND OF THE INVENTION

Feline herpesvirus 1 (FHV-1) is a member of the subfamily Alphaherpesvirinae and consists of a single linear molecule of double-stranded DNA (Rota et al., 1986). FHV-1 is widespread in the feline population, with as many as 71% of cats seropositive for this virus (Lappin et al., 2002), and it causes 50% of the cases of upper respiratory disease in cats (Maggs et al., 1999). Of these infections, FHV-1 causes the most severe clinical disease (Povey, 1976). Acute infections are usually localized to the respiratory tract, and clinical signs include pyrexia, ocular and nasal discharge, rhinitis, tracheitis, and depression (Burgener et al., 1988; Love, 1971). Primary ocular infection, as occurs in humans with the related herpes simplex virus type 1, consistently produces conjunctivitis and minimal corneal involvement. Acute signs, though potentially severe, usually resolve in a few weeks (Povey, 1976).

FHV-1 is very fragile in nature and does not survive long outside the host, so transmission requires close contact, especially mucosal contact; sneezing and short distance, droplet spread are significant in transmission in large confined populations, such as in breeding colonies and rescue catteries (Murphy et al., 1999). Upper respiratory infections in cats is second only to overcrowding as the leading cause of euthanasia in shelters, and FHV-1 is one of the main causes of shelter respiratory disease (Bannasch et al., 2005).

FHV-1 has been perpetuated in nature as a result of its ability to produce latent infections, and latently infected cats represent the most important reservoir of the virus (Gaskell et al., 1977; Maggs et al., 2003). Approximately 80% of cats infected with the virus become latently infected (Gaskell et al., 1977). During periods of stress such as changes in housing, parturition and lactation, or with corticosteroid administration, recrudescence occurs with associated viral shedding, with or without clinical disease. Also, 29% of latently infected cats are spontaneous shedders (Gaskell et al., 1977). Though the majority of latently infected cats do not develop chronic clinical disease (Andrew, 2001), there is still a large percentage of adult cats that have this problem (Stiles, 2003). The clinical manifestations of disease due to repeated recrudescence, including corneal ulcerations (Bistner et al., 1971), eosinophilic keratitis, or corneal sequestration (Nasisse et al., 1998), are significant and can lead to blindness (Andrew, 2001).

Antiviral medications approved for treatment of herpes simplex virus type 1 in humans are only minimally effective for treatment of these chronic cases in cats (Stiles, 1995). This is possibly due in part to the need for frequent application of the virostatic drugs and poor owner compliance (Stiles, 1995). Vaccines are available for FHV-1, but because the virus is poorly immunogenic (August, 1984), the vaccines do not prevent infection or shedding and only produce partial protection from clinical disease (Bittle et al., 1975). Therefore, development of a new therapeutic for FHV-1 would be beneficial.

Recently, a mechanism called RNA interference (RNAi) has been manipulated for prevention of various mammalian viral infections both in vitro and in vivo (Kim et al., 2007). RNA interference is a double stranded, RNA-guided gene silencing pathway that is found in a variety of eukaryotic organisms, including yeast, plants, and mammals (for a review, see reference Hammond, 2005). The double stranded RNA, small interfering RNAs (siRNA), that triggers the pathway can be supplied exogenously to silence specific genes (Elbashir et al., 2001; Hammond, 2005).

BRIEF SUMMARY OF THE INVENTION

The present application provides polynucleotides, compositions thereof and methods of treating feline herpes virus infections. In certain embodiments, the polynucleotides and compositions thereof can be used to reduce replication of feline herpes simplex virus 1 (FHV-1) in vivo and/or in vitro.

BRIEF DESCRIPTION OF THE DRAWINGS

FIGS. 15A and 15D are from non-transfected, uninfected CRFK cells.

BRIEF DESCRIPTION OF THE TABLES

Figure 1:
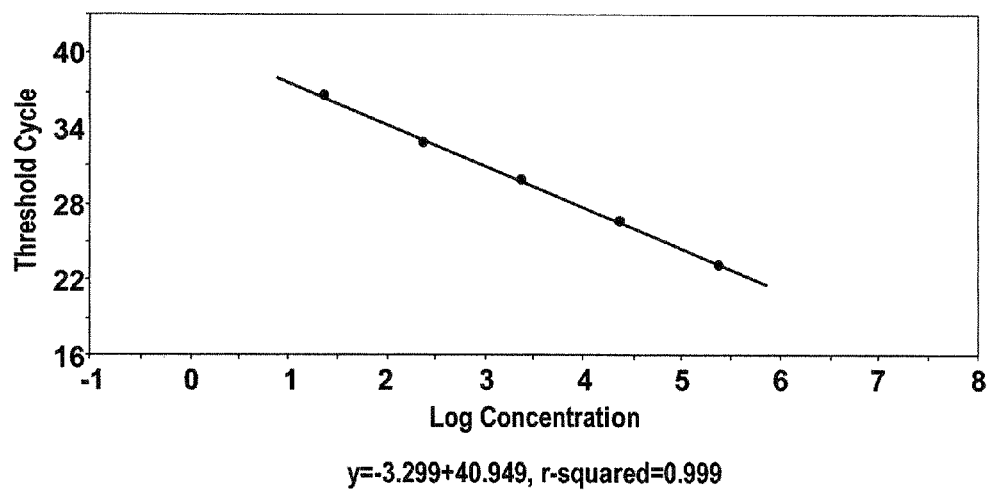
FIG. 1. GAPDH standard curve. The GAPDH standard curve was generated by testing five 10-fold serial dilutions of GAPDH standard RNA, and the theoretical limit of detection was 24 copies. The efficiency of the reaction was 101%, compared to the efficiency of 10-fold serial dilutions of GAPDH mRNA of 102% (not shown).

Table 1: siRNA for targeting mRNA.
Table 2: Primers and probes used to detect mRNA.
Table 3: siRNA for targeting FHV-1 glycoprotein D mRNA.
Table 4: Primers and probes used to detect mRNA.
Table 5 provides examples of various combinations of two or more polynucleotides that can be used in the formulation of compositions or in methods of treating FHV1 or decreasing expression of FHV-1 DNA polymerase and/or glycoprotein D in cells. The polynucleotide designations are as follows: 1=SEQ ID NO: 7 (DNA 1); 2=SEQ ID NO: 8 (DNA 2); 3=SEQ ID NO: 9 (DNA 3); 4=SEQ ID NO: 10 (DNA 4); 5=SEQ ID NO: 11 (DNA 5); 6=SEQ ID NO: 12 (gD 1); 7=SEQ ID NO: 13 (gD 2); 8=SEQ ID NO: 14 (gD 3); 9=SEQ ID NO: 15 (G1); 10=SEQ ID NO: 16 (G2); 11=SEQ ID NO: 17 (G3).

BRIEF DESCRIPTION OF THE SEQUENCES

SEQ ID NO: 1 is the sequence for the GAPDH gene as set forth in GenBank Accession No. AB038241 (hereby incorporated by reference in its entirety).

SEQ ID NO: 2 is a partial CDS sequence of the FHV-1 polymerase gene set forth in GenBank Accession No. AF079125 (hereby incorporated by reference in its entirety) and the complete FHV-1 polymerase gene sequence (SEQ ID NO: 39) is disclosed in Accession No. AJ224971 (hereby incorporated by reference in its entirety).

SEQ ID NO: 3 provides the sequence of the FHV-1 glycoprotein D gene set forth in GenBank Accession No. D30767 (hereby incorporated by reference in its entirety).

SEQ ID NOs: 4-6 provide illustrative siRNA sequences for Feline GAPDH (see Table 1).

SEQ ID NOs: 7-11 provide illustrative siRNA sequences for feline herpes virus DNA polymerase (see Table 1).

SEQ ID NOs: 12-17 are illustrative siRNA sequences for feline herpes virus (FHV) glycoprotein D (see Table 3).

SEQ ID NOs: 18-29 are primers or probes for GAPDH, 28S rRNA, interferon beta and FHV polymerase (see Table 2).

SEQ ID NOs: 30-38 are primers and probes for FHV glycoprotein D, 28S rRNA and interferon beta (see Table 4).

DETAILED DESCRIPTION OF THE INVENTION

As used herein, the term "polypeptide" refers to any polymer comprising any number of amino acids, and is interchangeable with "protein", "gene product", and "peptide".

As used herein, the term "nucleoside" refers to a molecule having a purine or pyrimidine base covalently linked to a ribose or deoxyribose sugar. Exemplary nucleosides include adenosine, guanosine, cytidine, uridine and thymidine.

The term "nucleotide" refers to a nucleoside having one or more phosphate groups joined in ester linkages to the sugar moiety. Exemplary nucleotides include nucleoside monophosphates, diphosphates and triphosphates.

The terms "polynucleotide" and "nucleic acid molecule" are used interchangeably herein and refer to a polymer of nucleotides joined together by a phosphodiester linkage between 5' and 3' carbon atoms. Polynucleotides of the subject invention include, for example, siRNA, antisense nucleic acids (antisense oligonucleotides), aptamers, ribozymes (catalytic RNA), and triplex-forming oligonucleotides (i.e., antigenes).

As used herein, the term "RNA" or "RNA molecule" or "ribonucleic acid molecule" refers generally to a polymer of ribonucleotides. The term "DNA" or "DNA molecule" or deoxyribonucleic acid molecule" refers generally to a polymer of deoxyribonucleotides. DNA and RNA molecules can be synthesized naturally (e.g., by DNA replication or transcription of DNA, respectively). RNA molecules can be post-transcriptionally modified. DNA and RNA molecules can also be chemically synthesized. DNA and RNA molecules can be single-stranded (i.e., ssRNA and ssDNA, respectively) or multi-stranded (e.g., double stranded, i.e., dsRNA and dsDNA, respectively). Based on the nature of the invention, however, the term "RNA" or "RNA molecule" or "ribonucleic acid molecule" can also refer to a polymer comprising primarily (i.e., greater than 80% or, preferably greater than 90%) ribonucleotides but optionally including at least one non-ribonucleotide molecule, for example, at least one deoxyribonucleotide and/or at least one nucleotide analog.

As used herein, the term "nucleotide analog" or "nucleic acid analog", also referred to herein as an altered nucleotide/nucleic acid or modified nucleotide/nucleic acid refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function. For example, locked nucleic acids (LNA) are a class of nucleotide analogs possessing very high affinity and excellent specificity toward complementary DNA and RNA. LNA oligonucleotides have been applied as antisense molecules both in vitro and in vivo (Jepsen J. S. et al., 2004).

As used herein, the term "RNA analog" refers to a polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. Exemplary RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, the term "operably-linked" or "operatively-linked" refers to an arrangement of flanking sequences wherein the flanking sequences so described are configured or assembled so as to perform their usual function. Thus, a flanking sequence operably-linked to a coding sequence may be capable of effecting the replication, transcription and/or translation of the coding sequence. For example, a coding sequence is operably-linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence, and the promoter sequence car still be considered "operably-linked" to the coding sequence. Each nucleotide sequence coding for an siRNA will typically have its own operably-linked promoter sequence.

The term "vector" is used to refer to any molecule (e.g., nucleic acid, plasmid, cationic lipid molecule, or virus) used to transfer coding information (e.g., a polynucleotide of the invention) to a host cell. The term "expression vector" refers to a vector that is suitable for use in a host cell (e.g., a subject's cell) and contains nucleic acid sequences which direct and/or control the expression of exogenous nucleic acid sequences. Expression includes, but is not limited to, processes such as transcription, translation, and RNA splicing, if introns are present.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference.

As used herein, a siRNA having a "sequence sufficiently complementary to a target mRNA sequence to direct target-specific RNA interference (RNAi)" means that the siRNA has a sequence sufficient to trigger the destruction of the target mRNA by the RNAi machinery or process. "mRNA" or "messenger RNA" or "transcript" is single-stranded RNA that specifies the amino acid sequence of one or more polypeptides. This information is translated during protein synthesis when ribosomes bind to the mRNA.

As used herein, the term "cleavage site" refers to the residues, e.g., nucleotides, at which RISC* cleaves the target RNA, e.g., near the center of the complementary portion of the target RNA, e.g., about 8-12 nucleotides from the 5' end of the complementary portion of the target RNA.

As used herein, the term "mismatch" refers to a basepair consisting of noncomplementary bases, e.g., not normal complementary G:C, A:T or A:U base pairs.

As used herein, the term "isolated" molecule (e.g., isolated nucleic acid molecule) refers to molecules which are substantially free of other cellular material, or culture medium when produced by recombinant techniques, or substantially free of chemical precursors or other chemicals when chemically synthesized.

As used herein, the term "in vitro" has its art recognized meaning, e.g., involving purified reagents or extracts, e.g., cell extracts. The term "in vivo" also has its art recognized meaning, e.g., involving living cells in an organism, e.g., immortalized cells, primary cells, and/or cell lines, in an organism.

A gene "involved in" or "associated with" a disorder includes a gene, the normal or aberrant expression or function of which affects or causes a disease or disorder or at least one symptom of the disease or disorder.

The methods of the invention may include further steps. In some embodiments, a subject with the relevant condition or disease (e.g., infection with a feline herpes virus) is identified or a patient at risk for acquiring feline herpes virus infection is identified. A subject may not have been diagnosed with a FHV infection or the subject may have been previously diagnosed with FHV infection and been treated. Alternatively, the subject may not have been diagnosed with a FHV infection, but is suspected of having the disease or condition based either on the subject's history or the exhibition or observation of characteristic symptoms.

As used herein, an "effective amount" of polynucleotide (e.g., an interfering RNA, an antisense nucleotide sequence or strand, and/or a ribozyme, which selectively interferes with expression of the glycoprotein D or DNA polymerase produced by feline herpes viruses is that amount effective to bring about the physiological changes desired in the cells to which the polynucleotide is administered in vitro (e.g., ex vivo) or in vivo. The term "therapeutically effective amount" as used herein, means that amount of polynucleotide (e.g., an siRNA, an antisense oligonucleotide, and/or a ribozyme, which selectively interferes with expression of the glycoprotein D and/or DNA polymerase, alone or in combination with another agent according to the particular aspect of the invention, that elicits the biological or medicinal response in cells (e.g., tissue(s)) that is being sought by a researcher, veterinarian, medical doctor or other clinician, and which includes alleviation and/or prevention of the symptoms of FHV infection.

Various methods of the present invention can include a step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing a siRNA of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

RNA Interference

RNAi is an efficient process whereby double-stranded RNA (dsRNA, also referred to herein as siRNAs or ds siRNAs, for double-stranded small interfering RNAs) induces the sequence-specific degradation of targeted mRNA in animal and plant cells (Hutvagner and Zamore, (2002); Sharp, (2001)). In mammalian cells, RNAi can be triggered by 21-nucleotide (nt) duplexes of small interfering RNA (siRNA) (Chiu et al, 2002; Elbashir et al., 2001), or by microRNAs (miRNA), functional small-hairpin RNA (shRNA), or other dsRNAs which can be expressed in vivo using DNA templates with RNA polymerase III promoters (Zeng et al., 2002; Paddison et al., 2002; Lee et al., 2002; Paul et al., 2002; Tuschl, 2002; Yu et al., 2002; McManus et al., 2002; Sui et al., 2002), each of which are incorporated herein by reference in their entirety.

Accordingly, the invention includes such interfering RNA molecules that are targeted to the mRNA molecules encoding FHV DNA polymerase molecules and/or glycoprotein D. The interfering RNA molecules are capable, when suitably introduced into or expressed within a cell that otherwise expresses these proteins, of suppressing their expression. The interfering RNA may be a double stranded siRNA. As the skilled person will appreciate, and as explained further herein, an siRNA molecule may include a short 3' DNA sequence also. Alternatively, the nucleic acid may be a DNA (usually double-stranded DNA) which, when transcribed in a cell, yields an RNA having two complementary portions joined via a spacer, such that the RNA takes the form of a hairpin when the complementary portions hybridize with each other. In a mammalian cell, the hairpin structure may be cleaved from the molecule by the enzyme DICER, to yield two distinct, but hybridized, RNA molecules.

Reduction (suppression) of expression results in a decrease of the amount of DNA polymerase and/or glycoprotein D mRNA. For example, in a given cell, the suppression of these mRNA molecules by administration of a polynucleotide (e.g., interfering RNA, antisense oligonucleotide, or ribozyme) results in a decrease in the quantity of mRNA encoding DNA polymerase and/or glycoprotein D relative to an untreated cell. Suppression may be partial. Preferred degrees of suppression are at least 50%, more preferably one of at least 60%, 70%, 80%, 85%, or 90%. A level of suppression between 90% and 100% is generally considered a "silencing" of expression.

In one embodiment, the invention provides an interfering RNA that is capable, when suitable introduced or expressed within a cell that otherwise expresses mRNA encoding DNA polymerase and/or glycoprotein D polypeptides, suppresses its expression by RNAi. In certain aspects of the invention, polynucleotides that reduce the expression of FHV-1 DNA polymerase, GAPDH or glycoprotein D polypeptides are provided. These polynucleotides include, and are not limited to, interfering RNAs, anti-sense oligonucleotides or ribozymes. Such polynucleotides can be generally targeted to: a) nucleotides 624-606, 679-661 or 785-767 of the GAPDH gene set forth in GenBank Accession No. AB038241 [SEQ ID NO: 1]; b) nucleotides 23-5, 70-52, 95-77, 121-103 or 144-126 of the FHV-1 polymerase gene set forth in GenBank Accession No. AF079125 [SEQ ID NO: 2]; and/or c) nucleotides 1076-1058, 1351-1333, 1397-1379, 1556-1538 or 1591-1573 of the FHV-1 glycoprotein D gene set forth in GenBank Accession No. D30767 [SEQ ID NO: 3]. The term "generally targeted" is intended to convey that the polynucleotide targets a sequence that overlaps with designated target sequence or target sequences discussed herein.

It is expected that perfect identity/complementarity between the interfering RNA of the invention and the target sequence, although preferred, is not essential. Accordingly, the interfering RNA may include a single mismatch compared to the mRNA of the target sequences. It is expected, however, that the presence of even a single mismatch is likely to lead to reduced efficiency, so the absence of mismatches is preferred. When present, 3' overhangs may be excluded from the consideration of the number of mismatches.

The term "complementarity" is not limited to conventional base pairing between nucleic acid consisting of naturally occurring ribo- and/or deoxyribonucleotides, but also includes base pairing between mRNA and nucleic acids of the invention that include non-natural nucleotides.

siRNA Molecules

Short interfering RNAs (siRNAs) induce the sequence-specific suppression or silencing (i.e., reducing expression which may be to the extent of partial or complete inhibition) genes by the process of RNAi. Thus, siRNA is the intermediate effector molecule of the RNAi process. The nucleic acid molecules (polynucleotides) or constructs of the invention include dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region discussed above, and the other strand is identical or substantially identical to the first strand. The dsRNA molecules of the invention can be chemically synthesized, or can be transcribed in vitro from a DNA template, or in vivo from, e.g., shRNA.

The polynucleotides of the invention can include both unmodified siRNAs and modified siRNAs as known in the art. Thus, the invention includes siRNA derivatives that include siRNA having two complementary strands of nucleic acid, such that the two strands are crosslinked. For example, a 3' OH terminus of one of the strands can be modified, or the two strands can be crosslinked and modified at the 3' OH terminus. The siRNA derivative can contain a single crosslink (e.g., a psoralen crosslink). In some embodiments, the siRNA derivative has at its 3' terminus a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying siRNA derivatives in this way can improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The nucleic acid compositions of the invention can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished by methods known in the art, e.g., using the methods of Lambert et al. 2001 (describes nucleic acids loaded to polyalkylcyanoacrylate (PACA) nanoparticles); Fattal et al. 1998 (describes nucleic acids bound to nanoparticles); Schwab et al., (1994) (describes nucleic acids linked to intercalating agents, hydrophobic groups, polycations or PACA nanoparticles); and Godard et al. 1995 (describes nucleic acids linked to nanoparticles).

The nucleic acid molecules of the present invention can also be labeled using any method known in the art; for instance, the nucleic acid compositions can be labeled with a fluorophore, e.g., Cy3, fluorescein, or rhodamine. The labeling can be carried out using a kit, e.g., the SILENCER siRNA labeling kit (AMBION). Additionally, the siRNA can be radiolabeled, e.g., using $^3$H, $^{32}$P, or other appropriate isotope.

siRNA Delivery for Longer-Term Expression

Synthetic siRNAs can be delivered into cells by methods known in the art, including cationic liposome transfection and electroporation. However, these exogenous siRNA generally show short term persistence of the silencing effect (4 to 5 days in cultured cells), which may be beneficial in certain embodiments. To obtain longer term suppression of DNA polymerase and/or glycoprotein D expression and to facilitate delivery under certain circumstances, one or more siRNA duplexes, e.g., ds siRNA, can be expressed within cells from recombinant DNA constructs. Such methods for expressing siRNA duplexes within cells from recombinant DNA constructs to allow longer-term target gene suppression in cells are known in the art, including mammalian Pol III promoter systems (e.g., H1 or U6/snRNA promoter systems (Tuschl 2002, supra) capable of expressing functional double-stranded siRNAs; (Bagella et al., 1998; Lee et al. 2002, supra; Miyagishi et al., 2002, supra; Paul et al., 2002, supra; Yu et al., 2002, supra; Sui et al., 2002, supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by an H1 or U6 snRNA promoter can be expressed in cells, and can inhibit target gene expression (Bagella et al., 1998, supra; Lee et al., 2002, supra; Miyagishi et al., 2002, supra; Paul et al., 2002, supra; Yu et al., 2002, supra; Sui et al., 2002 supra). Constructs containing siRNA sequence(s) under the control of a T7 promoter also make functional siRNAs when co-transfected into the cells with a vector expressing T7 RNA polymerase (Jacque, 2002, supra). A single construct may contain multiple sequences coding for siRNAs, such as multiple target sequences as described herein, and can be driven, for example, by separate PolIII promoter sites.

Animal cells express a range of noncoding RNAs of approximately 22 nucleotides termed micro RNA (miRNAs) which can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with miRNA sequence complementary to the target mRNA, a vector construct that expresses the novel miRNA can be used to produce siRNAs to initiate RNAi against specific mRNA targets in mammalian cells (Zeng 2002, supra). When expressed by DNA vectors containing polymerase III promoters, micro-RNA designed hairpins can silence gene expression (McManus 2002, supra). Viral-mediated delivery mechanisms can also be used to induce specific silencing of targeted genes through expression of siRNA, for example, by generating recombinant adenoviruses harboring siRNA under RNA Pol II promoter transcription control (Xia et al., 2002, supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. In an animal model, whole-embryo electroporation can efficiently deliver synthetic siRNA into post-implantation mouse embryos (Calegari et al., 2002). In adult mice, efficient delivery of siRNA can be accomplished by the "high-pressure" delivery technique, a rapid injection (within 5 seconds) of a large volume of siRNA containing solution into animal via the tail vein (Liu, 1999, supra; McCaffrey, 2002, supra; Lewis, 2002). Nanoparticles, liposomes and other cationic lipid molecules can also be used to deliver siRNA into animals. A gel-based agarose/liposome/siRNA formulation is also available (Jiamg M. et al. 2004).

Uses of Engineered RNA Precursors to Induce RNAi

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the mRNA to be targeted by the siRNA generated from the engineered RNA precursor will be depleted from the cell or organism, leading to a decrease in the concentration of any translational product encoded by that mRNA in the cell or organism. The RNA precursors are typically nucleic acid molecules that individually encode either one strand of a dsRNA or encode the entire nucleotide sequence of an RNA hairpin loop structure.

Antisense

An "antisense" nucleic acid sequence (antisense oligonucleotide) can include a nucleotide sequence that is complementary to a "sense" nucleic acid encoding a protein, e.g., complementary to the coding strand of a double-stranded cDNA molecule. Antisense nucleic acid sequences and delivery methods are well known in the art (Goodchild, 2004; Clawson et al., 2004), which are incorporated herein by reference in their entirety. The antisense nucleic acid can be complementary to an entire coding strand of a target sequence (e.g., FHV DNA polymerase and/or glycoprotein D), or to only a portion thereof. An antisense oligonucleotide can be, for example, about 7, 10, 15, 20, 25, 30, 35, 40, 45, 50, 55, 60, 65, 70, 75, 80, or more nucleotides in length and directed to one or more or the following target sequences: a) nucleotides 624-606, 679-661 or 785-767 of the GAPDH gene set forth in GenBank Accession No. AB038241 [SEQ ID NO: 1]; b) nucleotides 23-5, 70-52, 95-77, 121-103 or 144-126 of the FHV-1 polymerase gene set forth in GenBank Accession No. AF079125 [SEQ ID NO: 2]; and/or c) nucleotides 1076-1058, 1351-1333, 1397-1379, 1556-1538 or 1591-1573 of the FHV-1 glycoprotein D gene set forth in GenBank Accession No. D30767 [SEQ ID NO: 3].

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., systemically or locally by direct injection or application at a tissue site [e.g., mucosal surfaces]), or generated in situ such that they hybridize with or bind to cellular mRNA and/or genomic DNA encoding DNA polymerase and/or glycoprotein D. Alternatively, antisense nucleic acid molecules can be modified to target selected cells (such as endothelial cells and/or vascular endothelial cells) and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter can be used.

In yet another embodiment, the antisense oligonucleotide of the invention is an alpha-anomeric nucleic acid molecule. An alpha-anomeric nucleic acid molecule forms specific double-stranded hybrids with complementary RNA in which, contrary to the usual beta-units, the strands run parallel to each other (Gaultier et al., 1987). The antisense nucleic acid molecule can also comprise a 2'-o-methylribonucleotide (Inoue et al., 1987) or a chimeric RNA-DNA analogue (Inoue et al, 1987A).

Ribozymes

Ribozymes are a type of RNA that can be engineered to enzymatically cleave and inactivate other RNA targets in a specific, sequence-dependent fashion. Ribozymes and methods for their delivery are well known in the art (Hendry et al., 2004; Grassi et al., 2004; Bagheri S. et al., 2004; Kashani-Sabet, 2004), each of which are incorporated herein by reference in its entirety. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for target sequences comprising: a) nucleotides 624-606, 679-661 or 785-767 of the GAPDH gene set forth in GenBank Accession No. AB038241 [SEQ ID NO: 1]; b) nucleotides 23-5, 70-52, 95-77, 121-103 or 144-126 of the FHV-1 polymerase gene set forth in GenBank Accession No. AF079125 [SEQ ID NO: 2]; and/or c) nucleotides 1076-1058, 1351-1333, 1397-1379, 1556-1538 or 1591-1573 of the FHV-1 glycoprotein D gene set forth in GenBank Accession No. D30767 [SEQ ID NO: 3] and a sequence having known catalytic sequence responsible for mRNA cleavage (see U.S. Pat. No. 5,093,246 or Haselhoff and Gerlach, 1988) can be constructed. For example, a derivative of a Tetrahymena L-19 IVS RNA can be constructed in which the nucleotide sequence of the active site is complementary to the nucleotide sequence to be cleaved in the mRNA encoding DNA polymerase and/or glycoprotein D (see, e.g., Cech et al. U.S. Pat. No. 4,987,071; and Cech et al. U.S. Pat. No. 5,116,742).

Nucleic Acid Targets

The nucleic acid targets of the antisense, RNAi, and ribozymes as described herein may be any appropriate sequence within SEQ ID NO: 1, 2, 3 or 40. In certain embodiments, nucleic acid targets (target sequences) can be: a) nucleotides 624-606, 679-661 or 785-767 of the GAPDH gene set forth in GenBank Accession No. AB038241 [SEQ ID NO: 1]; b) nucleotides 23-5, 70-52, 95-77, 121-103 or 144-126 of the FHV-1 polymerase gene set forth in GenBank Accession No. AF079125 [SEQ ID NO: 2]; and/or c) nucleotides 1076-1058, 1351-1333, 1397-1379, 1556-1538 or 1591-1573 of the FHV-1 glycoprotein D gene set forth in GenBank Accession No. D30767 [SEQ ID NO: 3].

The term "ortholog" as used herein refers to a sequence which is substantially identical to a reference sequence. The term "substantially identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain or common functional activity. For example, amino acid or nucleotide sequences that contain a common structural domain having at least about 60%, or 65% identity, likely 75% identity, more likely 85%, 90%, 91%, 92%, 93%, 94%, 95%, 96%, 97%, 98% or 99% identity are defined herein as substantially identical.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 50%, at least 60%, at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences is determined using the Needleman and Wunsch (1970) algorithm, which has been incorporated into the GAP program in the GCG software package (available at the official Accelrys web site), using either a Blossum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (available at the official Accelrys web site), using a NWSgapdna.CMP matrix and a gap weight of 40, 50, 60, 70, or 80 and a length weight of 1, 2, 3, 4, 5, or 6. One set of parameters (and the one that can be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (1989) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other orthologs, e.g., family members or related sequences. Such searches can be performed using the NBLAST and XBLAST programs (version 2.0) of Altschul, et al. (1990). BLAST nucleotide searches can be performed with the NBLAST program, score=100, word length=12, to obtain nucleotide sequences homologous to known feline DNA polymerase and/or glycoprotein D sequences. BLAST protein searches can be performed with the XBLAST program, score=50, word length=3, to obtain amino acid sequences homologous to known polypeptide products of feline DNA polymerase and/or glycoprotein D genes. To obtain gapped alignments for comparison purposes, Gapped BLAST can be utilized as described in Altschul et al. (1997). When utilizing BLAST and Gapped BLAST programs, the default parameters of the respective programs (e.g., XBLAST and NBLAST) can be used (see the National Center for Biotechnology Information web site of the National Institutes of Health).

Orthologs can also be identified using any other routine method known in the art, such as screening a cDNA library, e.g., a human cDNA library, using a probe designed to identify sequences which are substantially identical to a reference sequence.

Pharmaceutical Compositions and Methods of Administration

The polynucleotides of the subject invention (e.g., siRNA molecules, antisense molecules, and ribozymes) can be incorporated into pharmaceutical compositions. Such compositions typically include the polynucleotide and a pharmaceutically acceptable carrier. As used herein, the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions. Formulations (compositions) are described in a number of sources that are well known and readily available to those skilled in the art. For example, *Remington's Pharmaceutical Sciences* (Martin E. W., Easton Pa., Mack Publishing Company, 19$^{th}$ ed., 1995) describes formulations which can be used in connection with the subject invention.

A pharmaceutical composition is formulated to be compatible with its intended route of administration. Examples of routes of administration include parenteral, e.g., intravenous, intradermal, subcutaneous, oral (e.g., inhalation), topical, transdermal, transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL (BASF, Parsippany, N.J.) or phosphate buffered saline (PBS). In all cases, the composition must be sterile and should be fluid to the extent that easy syringability exists. It should be stable under the conditions of manufacture and storage and be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. Isotonic agents, for example, sugars, polyalcohols such as manitol, sorbitol, sodium chloride can also be included in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polynucleotide of the invention) in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, suitable methods of preparation include vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the polynucleotides can be delivered in the form of an aerosol spray from a pressurized container or dispenser which contains a suitable propellant, e.g., a gas such as carbon dioxide, or a nebulizer. Such inhalation methods and inhalant formulations include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compound (e.g., polynucleotides of the invention) are formulated into ointments, salves, gels, or creams, as generally known in the art.

The pharmaceutical compositions can also be prepared in the form of suppositories (e.g., with conventional suppository bases such as cocoa butter and other glycerides) or retention enemas for rectal delivery.

The polynucleotides can also be administered by transfection or infection using methods known in the art, including but not limited to the methods described in McCaffrey et al. (2002) (hydrodynamic transfection); Xia et al. (2002) (viral-mediated delivery); or Putnam (1996).

The polynucleotides can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in Hamajima et al. (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the polynucleotides are prepared with carriers that will protect the polynucleotide against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. Liposomal suspensions (including liposomes targeted to antigen-presenting cells with monoclonal antibodies) can also be used as pharmaceutically acceptable carriers. These can be prepared according to methods known to those skilled in the art, for example, as described in U.S. Pat. No. 4,522,811. A strategy for the compaction of short oligonucleotides into well-defined condensates may also be used to deliver the polynucleotides of the subject invention (Sarkar et al., 2005), which is incorporated herein by reference in its entirety.

In particular, suitable techniques for cellular administration of the polynucleotides of the invention both in vitro and in vivo are disclosed in the following articles:

General Reviews: Borkhardt, A. (2002); Hannon (2002); McManus et al. (2002); Scherr et al. (2003); Shuey et al. (2002).

Systemic Delivery Using Liposomes: Lewis et al. (2002); Paul et al. (2002); Song et al. (2003); Sorensen et al. (2003).

Virus Mediated Transfer: Abbas-Terki et al. (2002); Barton et al. (2002); Devroe et al. (2002);

Lori et al. (2002); Matta et al. (2003); Qin et al. (2003); Scherr et al. (2003); Shen et al. (2003).

Peptide Delivery: Morris et al. (2000); Simeoni et al (2003).

Other technologies that may be suitable for delivery of polynucleotides of the invention such as interfering RNA to the target cells are based on nanoparticles or nanocapsules such as those described in U.S. Pat. Nos. 6,649,192B and 5,843,509B. Recent technologies that may be employed for selecting, delivering, and monitoring interfering RNA molecules include Raab, R. M. and Stephanopoulos, 2004; Huppi et al., 2005; Spagnou et al., 2004; Muratovska, A. and Eccles, M. R., 2004; Kumar, R. et al., 2003; Chen et al., 2005; Dykxhoorn et al., 2006; Rodriguez-Lebron et al., 2005; Pai et al., 2005; Raoul et al., 2005; Manfredsson et al., 2005; Downward, 2004.

Toxicity and therapeutic efficacy of compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions which exhibit high therapeutic indices can be used. While compositions that exhibit toxic side effects can be used, care should be taken to design a delivery system that targets such compounds to the site of affected tissue in order to minimize potential damage to uninfected cells and, thereby, reduce side effects.

The compositions of the invention can be administered on any appropriate schedule, e.g., from one or more times per day to one or more times per week; including once every other day, for any number of days or weeks, e.g., 1 day, 2 days, 3 days, 4 days, 5 days, 6 days, 1 week, 10 days, 2 weeks, 3 weeks, 4 weeks, 5 weeks, 6 weeks, 7 weeks, 8 weeks, 2 months, 3 months, 6 months, or more, or any variation thereon. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a polynucleotide can include a single treatment or can include a series of treatments.

The polynucleotides of the invention (e.g., interfering RNA, antisense oligonucleotide, or ribozyme) can be introduced (administered) into cells (such as mammalian cells) in vitro or in vivo using known techniques, as those described herein, to suppress gene expression. Similarly, genetic constructs (e.g., transcription vectors) containing DNA of the invention may be introduced into cells in vitro or in vivo using known techniques, as described herein, for transient or stable expression of RNA, to suppress gene expression. When administered to the cells in vivo, the polynucleotides of the invention can be administered to a subject systemically (e.g., intravenously), for example, or administered locally at the site of the cells (such as at the heart or vascular endothelium).

The polynucleotides of the invention can be inserted into genetic constructs, e.g., viral vectors, retroviral vectors, expression cassettes, or plasmid viral vectors, e.g., using methods known in the art, including but not limited to those described in Xia et al. (2002), supra. Genetic constructs can be delivered to a subject by, for example, inhalation, orally, intravenous injection, local administration (see U.S. Pat. No. 5,328,470) or by stereotactic injection (see, e.g., Chen et al. (1994). Certain embodiments of the invention contemplate delivery of the disclosed nucleic acids to mucosal surfaces of a subject (e.g., a feline). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the polynucleotide delivery system.

The polynucleotides of the invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides (Brummelkamp et al., 2002; Lee et al., 2002, supra; Miyagishi et al., 2002; Paddison et al., 2002, supra; Paul, 2002, supra; Sui, 2002, supra; Yu et al., 2002, supra).

siRNAs of the invention may be fused to other nucleotide molecules, or to polypeptides, in order to direct their delivery or to accomplish other functions. Thus, for example, fusion proteins comprising a siRNA oligonucleotide that is capable of specifically interfering with expression of the DNA polymerase and/or glycoprotein D may comprise affinity tag polypeptide sequences, which refers to polypeptides or peptides that facilitate detection and isolation of the such polypeptide via a specific affinity interaction with a ligand. The ligand may be any molecule, receptor, counter-receptor, antibody or the like with which the affinity tag may interact through a specific binding interaction as provided herein. Such peptides include, for example, poly-His or "FLAG" or the like, e.g., the antigenic identification peptides described in U.S. Pat. No. 5,011,912 and in Hopp et al. (1988), or the XPRESS epitope tag (INVITROGEN, Carlsbad, Calif.). The affinity sequence may be a hexa-histidine tag as supplied, for example, by a pBAD/His (INVITROGEN) or a pQE-9 vector to provide for purification of the mature polypeptide fused to the marker in the case of a bacterial host, or, for example, the affinity sequence may be a hemagglutinin (HA) tag when a mammalian host, e.g., COS-7 cells, is used. The HA tag corresponds to an antibody defined epitope derived from the influenza hemagglutinin protein (Wilson et al., 1984).

The present invention also relates to vectors and to constructs that include or encode polynucleotides of the present invention (e.g., siRNA), and in particular to "recombinant nucleic acid constructs". According to the present invention, a vector may comprise a recombinant nucleic acid construct containing one or more promoters for transcription of an RNA molecule, for example, the human U6 snRNA promoter (see, e.g., Miyagishi et al., 2002; Lee et al., 2002; Paul et al., 2002; Grabarek et al., 2003); see also Sui et al., 2002). Each strand of a siRNA polynucleotide may be transcribed separately each under the direction of a separate promoter and then may hybridize within the cell to form the siRNA polynucleotide duplex. Each strand may also be transcribed from separate vectors (see Lee et al., supra). Alternatively, the sense and antisense sequences specific for a target sequence may be transcribed under the control of a single promoter such that the siRNA polynucleotide forms a hairpin molecule (Paul et al., supra). In such an instance, the complementary strands of the siRNA specific sequences are separated by a spacer that comprises at least four nucleotides, but may comprise at least 5, 6, 7, 8, 9, 10, 11, 12, 14, 16, or 18 or more nucleotides as described herein. In addition, siRNAs transcribed under the control of a U6 promoter that form a hairpin may have a stretch of about four uridines at the 3' end that act as the transcription termination signal (Miyagishi et al., supra; Paul et al., supra). By way of illustration, if the target sequence is 19 nucleotides, the siRNA hairpin polynucleotide (beginning at the 5' end) has a 19-nucleotide sense sequence followed by a spacer (which as two uridine nucleotides adjacent to the 3' end of the 19-nucleotide sense sequence), and the spacer is linked to a 19 nucleotide antisense sequence followed by a 4-uridine terminator sequence, which results in an overhang. siRNA polynucleotides with such overhangs effectively interfere with expression of the target polypeptide. A recombinant construct may also be prepared using another RNA polymerase III promoter, the HI RNA promoter, that may be operatively linked to siRNA polynucleotide specific sequences, which may be used for transcription of hairpin structures comprising the siRNA specific sequences or separate transcription of each strand of a siRNA duplex polynucleotide (see, e.g., Brummelkamp et al., 2002; Paddison et al., supra). DNA vectors useful for insertion of sequences for transcription of an siRNA polynucleotide include pSUPER vector (see, e.g., Brummelkamp et al, supra); pAV vectors derived from pCWRSVN (see, e.g., Paul et al., supra); and pIND (see, e.g., Lee et al., supra), or the like.

Polynucleotides of the invention can be expressed in mammalian cells, yeast, bacteria, or other cells under the control of appropriate promoters, providing ready systems for evaluation of siRNA polynucleotides that are capable of interfering with polypeptide expression as provided herein. Appropriate cloning and expression vectors for use with prokaryotic and eukaryotic hosts are described, for example, by Sambrook et al. (2001).

The appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Ausubel et al. (1993); Sambrook et al. (2000); Maniatis et al. (1982); and elsewhere.

The DNA sequence in the expression vector is operatively linked to at least one appropriate expression control sequence (e.g., a promoter or a regulated promoter) to direct mRNA synthesis. Representative examples of such expression control sequences include LTR or SV40 promoter, the E. coli lac or trp, the phage lambda $P_L$ promoter and other promoters known to control expression of genes in prokaryotic or eukaryotic cells or their viruses. Promoter regions can be selected from any desired gene using CAT (chloramphenicol transferase) vectors or other vectors with selectable markers.

Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art, and preparation of certain particularly preferred recombinant expression constructs comprising at least one promoter or regulated promoter operably linked to a polynucleotide of the invention is described herein.

As noted above, in certain embodiments the vector may be a viral vector such as a mammalian viral vector (e.g., retrovirus, adenovirus, adeno-associated virus, lentivirus). For example, retroviruses from which the retroviral plasmid vectors may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

The viral vector includes one or more promoters. Suitable promoters which may be employed include, but are not limited to, the retroviral LTR; the SV40 promoter; and the human cytomegalovirus (CMV) promoter described in Miller (1989), or any other promoter (e.g., cellular promoters such as eukaryotic cellular promoters including, but not limited to, the histone, pol III, and beta-actin promoters). Other viral promoters that may be employed include, but are not limited to, adenovirus promoters, adeno-associated virus promoters, thymidine kinase (TK) promoters, and B19 parvovirus promoters. The selection of a suitable promoter will be apparent to those skilled in the art from the teachings contained herein, and may be from among either regulated promoters (e.g., tissue-specific or inducible promoters) or promoters as described above). A tissue-specific promoter allows preferential expression of the polynucleotide in a given target tissue, thereby avoiding expression in other tissues. For example, to express genes specifically in the heart, a number of cardiac-specific regulatory elements can be used. An example of a cardiac-specific promoter is the ventricular form of MLC-2v promoter (see, Zhu et al., 1993; Navankasattusas et al., 1992) or a variant thereof such as a 281 bp fragment of the native MLC-2v promoter (nucleotides −264 to +17, Genebank Accession No. U26708). Examples of other cardiac-specific promoters include alpha myosin heavy chain (Minamino et al., 2001) and myosin light chain-2 (Franz et al., 1993). Endothelial cell gene promoters include endoglin and ICAM-2. See Velasco et al., 2001. Liver-specific promoters include the human phenylalanine hydroxylase (PAH) gene promoters (Bristeau et al., 2001), hB1F (Zhang et al., 2001), and the human C-reactive protein (CRP) gene promoter (Ruther et al., 1993). Promoters that are kidney-specific include CLCN5 (Tanaka et al., 1999), renin (Sinn et al., 2000), androgen-regulated protein, sodium-phosphate cotransporter, renal cytochrome P-450, parathyroid hormone receptor and kidney-specific cadherin. See Am. J. Physiol. Renal Physiol., 2000. An example of a pancreas-specific promoter is the pancreas duodenum homeobox 1 (PDX-1) promoter (Samara et al., 2002). A number of brain-specific promoters may be useful in the invention and include the thy-1 antigen and gamma-enolase promoters (Vibert et al, 1989), the glial-specific glial fibrillary acidic protein (GFAP) gene promoter (Cortez et al., 2000), and the human FGF1 gene promoter (Chiu et al., 2000). The GATA family of transcription factors have promoters directing neuronal and thymocyte-specific expression (see Asnagli et al., 2002).

In another aspect, the present invention relates to host cells containing the above described recombinant constructs. Host cells are genetically engineered/modified (transduced, transformed or transfected) with the vectors and/or expression constructs of this invention that may be, for example, a cloning vector, a shuttle vector, or an expression construct. The vector or construct may be, for example, in the form of a plasmid, a viral particle, a phage, etc. The engineered host cells can be cultured in conventional nutrient media modified as appropriate for activating promoters, selecting transformants or amplifying particular genes such as genes encoding siRNA polynucleotides or fusion proteins thereof. The culture conditions for particular host cells selected for expression, such as temperature, pH and the like, will be readily apparent to the ordinarily skilled artisan.

The host cell can be a higher eukaryotic cell, such as a mammalian cell, or a lower eukaryotic cell, such as a yeast cell, or the host cell can be a prokaryotic cell, such as a bacterial cell. Representative examples of appropriate host cells according to the present invention include, but need not be limited to, bacterial cells, such as E. coli, Streptomyces, Salmonella typhimurium; fungal cells, such as yeast; insect cells, such as Drosophila S2 and Spodoptera Sf9; animal cells, such as CHO, COS or 293 cells; adenoviruses; plant cells, or any suitable cell already adapted to in vitro propagation or so established de novo.

Various mammalian cell culture systems can also be employed to produce polynucleotides of the invention from recombinant nucleic acid constructs of the present invention. The invention is therefore directed in part to a method of producing a polynucleotide, such as an siRNA, by culturing a host cell comprising a recombinant nucleic acid construct that comprises at least one promoter operably linked to a polynucleotide of the invention. In certain embodiments, the promoter may be a regulated promoter as provided herein, for example a tetracycline-repressible promoter. In certain embodiments the recombinant expression construct is a recombinant viral expression construct as provided herein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa, HEK, and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences, for example as described herein regarding the preparation of recombinant polynucleotide constructs. DNA sequences derived from the SV40 splice, and polyadenylation sites may be used to provide the required nontranscribed genetic elements. Introduction of the construct into the host cell can be effected by a variety of methods with which those skilled in the art will be familiar, including but not limited to, for example, liposomes including cationic liposomes, calcium phosphate transfection, DEAE-Dextran mediated transfection, or electroporation (Davis et al., 1986), or other suitable technique.

The expressed polynucleotides may be useful in intact host cells; in intact organelles such as cell membranes, intracellular vesicles or other cellular organelles; or in disrupted cell preparations including but not limited to cell homogenates or lysates, microsomes, uni- and multilamellar membrane vesicles or other preparations. Alternatively, expressed polynucleotides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Finally, high performance liquid chromatography (HPLC) can be employed for final purification steps.

Thus, the subject application provides the following embodiments:

1. A composition comprising a carrier and a combination of two or more polynucleotides selected from SEQ ID NOs: 7, 8, 9, 10, 11, 12, 13, 14, 15, 16 or 17.

2. The composition according to embodiment 1, wherein said combination of two or more polynucleotides are selected from those set forth in Table 5.

3. The composition according to embodiment 2, wherein said combination of two or more polynucleotides are double stranded siRNA molecules of between 16 and 30 nucletotides, said double stranded siRNA molecules comprising a first sequence comprising SEQ ID NO: 7, 8, 9, 10, 11, 12, 13, 14, 15, 16 or 17 and a second sequence that is complementary thereto, wherein said siRNA molecule contains 0, 1, 2, 3 or 4 base mismatches.

4. An isolated polynucleotide that reduces expression of feline glyceraldehyde-3-phosphate dehydrogenase (GAPDH), FHV-1 DNA polymerase, or glycoprotein D polypeptides.

5. The polynucleotide of embodiment 4, wherein said polynucleotide is an interfering RNA, anti-sense oligonucleotide, or ribozyme.

6. The polynucleotide of embodiment 4, wherein said polynucleotide is selected from an interfering RNA that targets:
  a) nucleotides 624-606, 679-661 or 785-767 of the GAPDH gene set forth in GenBank Accession No. AB038241 [SEQ ID NO: 1];
  b) nucleotides 23-5, 70-52, 95-77, 121-103 or 144-126 of the FHV-1 polymerase gene set forth in GenBank Accession No. AF079125 [SEQ ID NO: 2];
  c) nucleotides 1076-1058, 1351-1333, 1397-1379, 1556-1538 or 1591-1573 of the FHV-1 glycoprotein D gene set forth in GenBank Accession No. D30767 [SEQ ID NO: 3]; or
  d) SEQ ID NO: 39.

7. The polynucleotide of embodiment 4, wherein said polynucleotide comprises SEQ ID NO: 4, 5, 6, 7, 8, 9, 10, 11, 12, 13, 14, 15, 16 or 17.

8. The polynucleotide of embodiment 4, 5, 6 or 7, wherein said polynucleotide is an siRNA or a shRNA.

9. The polynucleotide of embodiment 4, 5, 6 or 7, wherein said polynucleotide is an shRNA.

10. A composition comprising a polynucleotide according to any one of embodiments claims 4-9 and a pharmaceutically acceptable carrier.

11. The composition of embodiment 10, wherein said polynucleotide reduces expression of FHV-1 DNA polymerase, GAPDH or glycoprotein D polypeptides.

12. The composition of embodiment 10, wherein said polynucleotide wherein said polynucleotide is an interfering RNA, anti-sense oligonucleotide, or ribozyme.

13. The composition of embodiment 10, wherein said polynucleotide is selected from an interfering RNA that targets:
  a) nucleotides 624-606, 679-661 or 785-767 of the GAPDH gene set forth in GenBank Accession No. AB038241 [SEQ ID NO: 1];
  b) nucleotides 23-5, 70-52, 95-77, 121-103 or 144-126 of the FHV-1 polymerase gene set forth in GenBank Accession No. AF079125 [SEQ ID NO: 2];
  c) nucleotides 1076-1058, 1351-1333, 1397-1379, 1556-1538 or 1591-1573 of the FHV-1 glycoprotein D gene set forth in GenBank Accession No. D30767 [SEQ ID NO: 3]; or
  d) SEQ ID NO: 39.

14. The composition of embodiment 10, wherein said polynucleotide comprises SEQ ID NO: 4, 5, 6, 7, 8, 9, 10, 11, 12, 13, 14, 15, 16 or 17.

15. The composition of embodiment 10, wherein said polynucleotide is an siRNA.

16. The composition of embodiment 11, wherein said polynucleotide is an shRNA.

17. A composition comprising a pharmaceutically acceptable carrier and a combination of two or more polynucleotides, wherein said polynucleotides are selected from an interfering RNAs that target:
  a) nucleotides 23-5, 70-52, 95-77, 121-103 or 144-126 of the FHV-1 polymerase gene set forth in GenBank Accession No. AF079125 [SEQ ID NO: 2]; or
  b) nucleotides 1076-1058, 1351-1333, 1397-1379, 1556-1538 or 1591-1573 of the FHV-1 glycoprotein D gene set forth in GenBank Accession No. D30767 [SEQ ID NO: 3].

18. A method of decreasing expression of FHV-1 DNA polymerase and/or glycoprotein D in cells, comprising administering a composition comprising an effective amount of a polynucleotide that reduces expression of FHV-1 DNA polymerase and/or glycoprotein D.

19. The method of embodiment 18, wherein said polynucleotide is an interfering RNA, anti-sense oligonucleotide, or ribozyme.

20. The method of embodiment 18 or 19, wherein said polynucleotide is selected from an interfering RNA that targets:
  a) nucleotides 23-5, 70-52, 95-77, 121-103 or 144-126 of the FHV-1 polymerase gene set forth in GenBank Accession No. AF079125 [SEQ ID NO: 2]; or
  b) nucleotides 1076-1058, 1351-1333, 1397-1379, 1556-1538 or 1591-1573 of the FHV-1 glycoprotein D gene set forth in GenBank Accession No. D30767 [SEQ ID NO: 3].

21. The method of embodiment 18, wherein said polynucleotide comprises SEQ ID NO: 7, 8, 9, 10, 11, 12, 13, 14, 15, 16 or 17.

22. The method of embodiment 18, wherein said composition comprises a combination of two or more polynucleotides is selected from SEQ ID NOs: 7, 8, 9, 10, 11, 12, 13, 14, 15, 16 or 17.

23. The method of embodiment 18, wherein said composition is administered to a mucosal surface of a feline.

24. The method of embodiment 23, wherein said composition is a composition according to claims 1-3 or 10-17

As used herein, the terms "administer", "introduce", "apply", "treat", "transplant", "implant", "deliver", and grammatical variations thereof, are used interchangeably to provide polynucleotides or vectors of the subject invention to target cells in vitro (e.g., ex vivo) or in vivo, or provide genetically modified (engineered) cells of the subject invention to a subject.

As used herein, the term "co-administration" and variations thereof refers to the administration of two or more agents simultaneously (in one or more preparations), or consecutively. For example, one or more types of genetically modified cells of the invention can be co-administered with other agents. Non-limiting examples of such agents include anti-viral agents such as trifluridine (VIROPTIC) or idoxuridine (STOXIL). Anti-viral agents, such as trifluridine and idoxuridine may be administered topically in combination with siRNA molecules disclosed herein.

As used in this specification, including the appended claims, the singular "a", "an", and "the" include plural reference unless the contact dictates otherwise. Thus, for example, a reference to "a polynucleotide" includes more than one such polynucleotide. A reference to "a nucleic acid sequence"

includes more than one such sequence. A reference to "a cell" includes more than one such cell.

The terms "comprising", "consisting of" and "consisting essentially of" are defined according to their standard meaning. The terms may be substituted for one another throughout the instant application in order to attach the specific meaning associated with each term.

Following are examples which illustrate procedures for practicing the invention. These examples should not be construed as limiting. All percentages are by weight and all solvent mixture proportions are by volume unless otherwise noted.

EXAMPLE 1

Inhibition of FHV-1 DNA Polymerase

Materials and Methods

Cells and viruses. Crandell-Reese feline kidney (CRFK) cells (American Type Culture Collection [ATCC], Manassas, Va.) were propagated and maintained in Dulbecco's minimal essential medium (DMEM) (Cambrex, Charles City, Iowa) supplemented with heat-inactivated 5% fetal bovine serum (Atlanta Biologicals, Lawrenceville, Ga.), 100 U/ml penicillin, 100 µg/ml streptomycin, and Fungizone (Cambrex) at 37° C. in a 5% $CO_2$ incubator. The prototype FHV-1 strain C-27 (ATCC) was used for the study. A calicivirus wild-type strain used in the study and 10 FHV-1 isolates from 2003-2006 were a generous gift from the Clinical Virology Laboratory, University of Tennessee, Knoxville, Tenn.

siRNAs and transfection. Five siRNAs designed to target the DNA polymerase mRNA of FHV-1 were produced by Ambion-Applied Biosystems (Austin, Tex.) (Table 1). Transfections of 100 nM siRNA per well in six well plates were performed with 5 µL of Lipofectamine 2000 (Invitrogen, Carlsbad, Calif.) per sample using Opti-MEM (Gibco-Invitrogen), according to the manufacturer's protocol. Approximately $5\times10^4$ CRFK cells were diluted in DMEM supplemented with 10% FBS and added to each well containing the transfection mixtures. Plates were incubated for 24 h prior to infection with FHV-1. Each siRNA was tested in duplicate, and functional siRNAs were retested for a total of three experiments per siRNA. A non-targeting negative control siRNA was purchased from Ambion. siRNAs targeting the feline GAPDH gene, also obtained from Ambion, were used as a positive control to verify effective siRNA transfection (Table 1). Other controls used for each experiment included uninfected/mock-transfected CRFK cells, FHV-1 infected/non-transfected cells, and a type 1 interferon control. The type 1 interferon control consisted of non-transfected CRFK cells infected with feline calicivirus, an RNA virus that activates interferon β in CRFK cells.

Virus infection and plaque assays. The FHV-1 strain C-27 (ATCC) was grown in CRFK cells until a 50% cytopathic effect was visible. Plaque-forming units were determined by plaque assay as previously described (Burleson et al., 1992). However, instead of using an agarose overlay, serum from a cat with an IFA titer of >1:2560 (a gift from the University of Tennessee Clinical Virology Lab) was used at a dilution of 1:50. Aliquots of virus were prepared and frozen at −80° C., and each aliquot was used only once for each experiment.

Transfected CRFK cells were infected with FHV-1 at a multiplicity of infection (MOI) of 0.1. One hour after incubation, the cells were washed with DMEM, and fresh DMEM supplemented with 10% FBS was added to each well. Infected cells were incubated for a total of 48 h. 500 µL of cell culture medium was removed from each well at 48 h and stored at −80° C. until plaque assays could be performed.

Flow cytometry. Forty-eight hours after infection, the cells in each test and control well were trypsinized, washed with phosphate-buffered saline (PBS) (Gibco-Invitrogen), and resuspended in 1 mL of PBS per sample. One hundred µL of each suspension was removed and placed on ice for later RNA extraction. An additional 100 µL of each suspension was removed and processed for Western blot analysis, and the rest of each sample was processed for flow cytometry.

The flow cytometry samples were washed in flow buffer (60 mL 0.5% sodium azide solution, 87 mL PBS, and 3 mL FBS), and the cells were pelleted. The cells from each sample were stained with 200 µL fluorescein isothiocyanate-labeled, cat anti-FHV polyclonal antibody (Accurate Chemical and Scientific, Westbury, N.Y.) for 1 h on ice. The cells were then washed in PBS and resuspended in 1 mL PBS per sample. Cell surface fluorescence was assessed with an Epics XL flow cytometer (Beckman Coulter, Fullerton, Calif.).

Western blot analysis. Cells were combined with SDS sample buffer and boiled for 5 min. Samples were stored at −20° C. until later assayed. Proteins were electrophoresed on 10% polyacrylamide gels and transferred to nitrocellulose membranes (Bio-Rad, Hercules, Calif.). The membranes were probed with CRFK adsorbed, cat anti-FHV-1 polyclonal antibody (Accurate Chemical and Scientific) or anti-GAPDH monoclonal antibody (Chemicon International-Millipore, Billerica, Mass.), and anti-β actin monoclonal antibody (Ambion) was used as a loading control. Samples were incubated for 1 h on a shaker at room temperature. The membranes were washed five times and probed with peroxidase-labeled, goat anti-mouse IgG (GAPDH and beta actin monoclonals) or peroxidase-labeled, goat anti-feline IgG (FHV polyclonal) secondary antibodies (KPL, Gaithersburg, Md.) for 1 h on a shaker at room temperature. Five additional washes were performed, and proteins were detected by enhanced chemiluminescence (Amersham Biosciences, Piscataway, N.J.). The density of the protein bands was determined with a visible scanning densitometer (Quick Scan 2000, Helena Laboratories, Beaumont, Tex.).

RNA extraction and real-time RT-PCR. Total RNA was extracted from 100 µL aliquots of each test and control sample with the RNeasy Mini Kit (Qiagen, Valencia, Calif.) according to the manufacturer's protocol. Two on-column DNase digestions (Qiagen) were performed for each RNA sample, and the samples were diluted 1:1000 to reduce DNA contamination. Purified RNA samples were stored at −80° C. until tested by real-time, reverse-transcription polymerase chain reaction (RT-PCR). Primers and probes for real-time RT-PCR were designed with Primer3 (Rozen et al., 2000) to detect FHV-1 DNA polymerase and interferon β mRNA (Table 2). 28S rRNA was used as a control to standardize RNA concentration (Table 2). Primers, probe, and RT-PCR cycling parameters for feline GAPDH were previously published (Nguyen et al., 2006) (Table 2). RT-PCR was performed for each transcript using the SuperScript III Platinum One-Step qRT-PCR kit (Invitrogen). Five µL of diluted RNA was used in 25 µL total volume reactions, which contained 200 nM of each probe, 300 nM of each primer, and 40U of RNaseOut recombinant ribonuclease inhibitor (Invitrogen). Amplification of FHV-1 DNA polymerase was carried out in a SmartCycler® II (Cepheid, Sunnyvale, Calif.) with the following parameters: cDNA production at 45° C. for 30 min, hot start Taq polymerase activation at 95° C. for 2 min, followed by 45 cycles of denaturation at 95° C. for 15 s, annealing at 55° C. for 60 s, and extension at 72° C. for 30 s. The parameters for interferon β and 28S rRNA were as follows:

cDNA production at 42° C. (interferon) or 50° C. (28S) for 30 min, 95° C. for 2 min, followed by 45 cycles of 95° C. for 15 s, 60° C. (interferon) or 62° C. (28S) for 60 s, and 72° C. for 30 s. Extensive DNA contamination was ruled out by RTase negative controls, which were run with Platinum taq (Invitrogen) instead of SuperScript III. Each set of samples was run with three mRNA standard dilutions, generating curves for mRNA quantitation.

mRNA standards and standard curve production. mRNA standards were produced for FHV-1 DNA polymerase and feline GAPDH by ligating each PCR product into a pCR2.1 plasmid vector, and the recombinants were transduced into *Escherichia coli* (TA Cloning Kit, Invitrogen). The plasmids were isolated (SNAP MiniPrep Kit, Invitrogen), and the identity and orientation of the cloned products were determined by sequencing (Molecular Biology Resources Service, University of Tennessee, Knoxville, Tenn.). The plasmids were linearized (Hind III, Fisher Scientific) and used for in vitro transcription (AmpliCap T7 High Yield Message Maker Kit, Epicentre Biotechnologies, Madison, Wis.). Following treatment with DNase (Qiagen), the mRNA transcripts were purified (RNeasy Mini Kit, Qiagen). These standards were used to produce standard curves for absolute quantitation of FHV-1 DNA polymerase and feline GAPDH mRNA transcripts isolated from the samples. The RNA concentration and purity of the standards were determined by spectrophotometrical analysis at OD 260/280 (BioPhotometer 6131 spectrophotometer, Eppendorf, Westbury, N.Y.). The number of RNA copies in the sample was estimated based on the molecular weight of the RNA standards and the RNA concentration. Ten fold serial dilutions of the RNA stock were prepared, and aliquots were made and frozen immediately at −80° C. Each aliquot was used only once for real-time RT-PCR.

A standard curve was generated by testing 10-fold serial dilutions of the standard RNA by real-time RT-PCR and by using SmartCycler® II software (Cepheid). The intra-assay and inter-assay coefficients of reaction variations were determined using dilutions of the standard RNA as previously described (Stelzl et al., 2004). To ensure the standard RNA and the target RNA were amplified with similar efficiencies according to the calculation: Efficiency=$[10^{(-1/slope)}]-1$ (Wong et al., 2005), four 10-fold serial dilutions of RNA extracted from a CRFK control well and an FHV-infected control well were also prepared and tested in quadruplicate by real-time RT-PCR.

Statistical analysis. The results for the DNA polymerase-specific siRNA test and control groups were compared by using univariate ANOVA (SPSS software) because all assumptions were met, based on the Levene's test for equality of variances and the Shapiro-Wilk test for normality. Because the results lacked a normal distribution, the real-time RT-PCR results for GAPDH-specific siRNA control groups were compared using the Mann-Whitney Test. Due to unequal variances between treatment groups, univariate ANOVA and a Post Hoc Dunnett T3 test were used to compare controls with GAPDH-specific siRNA treatment groups.

Results

Figure 2:
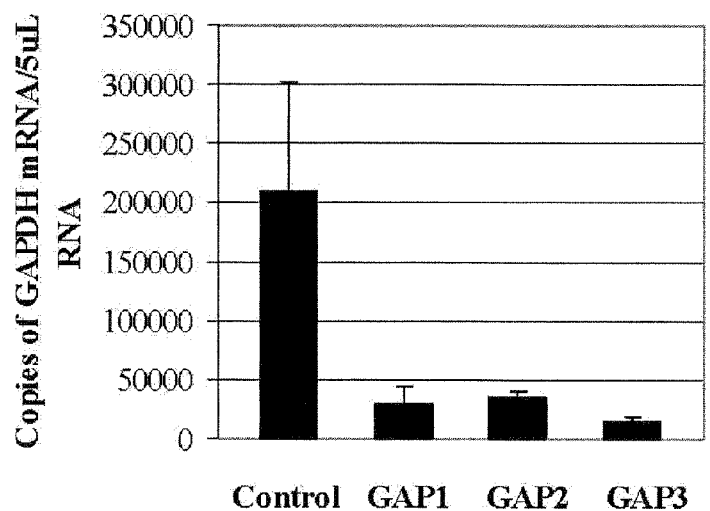
FIG. 2. Knockdown of feline GAPDH mRNA by siRNAs. CRFK cells were transfected with feline GAPDH-specific siRNAs (GAP1, GAP2, GAP3) or negative control siRNA. Following 48 h incubation, total RNA was extracted from cells and tested by real-time RT-PCR with primers specific for GAPDH mRNA or 28S rRNA. The samples were normalized with 28S rRNA, and copies of GAPDH mRNA were estimated from a standard curve generated by 10-fold serial dilutions of a GAPDH RNA standard. Three independent experiments were performed, and the results show the means of the experiments; error bars represent standard deviation from the mean. GAP1 (P=0.026), GAP2 (P=0.029), and GAP3 (P=0.019) are significantly different from the control, based on statistical analysis. Control=average of results from mock-transfected and negative control, siRNA-transfected CRFK cells (not statistically different, P=1).

RNAi of feline GAPDH. In order to determine if RNAi could be performed in CRFK cells with siRNAs transfected with Lipofectamine 2000, an endogenous gene, feline GAPDH, was chosen as a target. CRFK cells were transfected with each GAPDH-specific siRNA separately and compared to negative control siRNA-transfected cells and mock-transfected cells. Forty-eight hours following transfection, knockdown of GAPDH mRNA was assessed by quantitative real-time RT-PCR. RNA was standardized by 28S rRNA, which had a reaction efficiency of 102% (data not shown). GAPDH mRNA copy numbers were calculated from the standard curve, which was linear over five orders of magnitude (slope=−3.299) and resulted in a theoretical limit of detection of 24 copies (FIG. 1). The intra-assay variation within the portion of the curve used for mRNA copy calculations was 10-35% based on copy numbers (0.58-1.95% based on Ct values), and the inter-assay variation was 18-43% based on copy numbers (1.15-2.26% based on Ct values). The GAPDH-specific siRNA, GAP1, GAP2, and GAP3, resulted in decreased GAPDH mRNA by 86%, 83%, and 93%, respectively, compared to the control, which consisted of an average of the results from the negative control siRNA-transfected and mock-transfected CRFK cells (FIG. 2). The knockdown of GAPDH mRNA was independent of type 1 interferon production, determined by insignificant interferon β mRNA production in siRNA treated cells (similar to the amount detected in mock-transfected cells) compared to the control, CRFK cells infected with feline calicivirus, an interferon β activator (data not shown).

Figure 3:
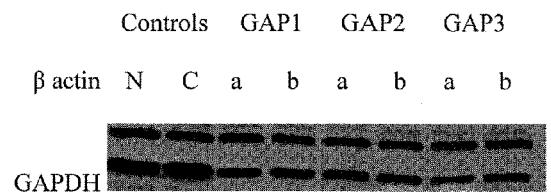
FIG. 3. Reduction of GAPDH protein expression by siRNAs. CRFK cells were transfected with 100 nM each of feline GAPDH-specific siRNAs (GAP1-3), and total cellular material was harvested after 48 h incubation. Western blot analysis was performed with anti-GAPDH and anti-beta actin monoclonal antibodies. Each siRNA was run in duplicate (a,b) with a CRFK control transfected with negative control siRNA (N) and a CRFK mock-transfected control (C). Beta-actin was used as a loading control to normalize protein concentrations, and the density of the protein bands was determined with a visible scanning densitometer. The results of a representative experiment are shown.

GAPDH mRNA knockdown also resulted in reduced GAPDH protein expression. GAPDH protein was reduced by 43%, 24%, and 64%, by GAP1, GAP2, and GAP3, respectively, compared to non-treated and negative siRNA treated controls (FIG. 3).

Figure 4:
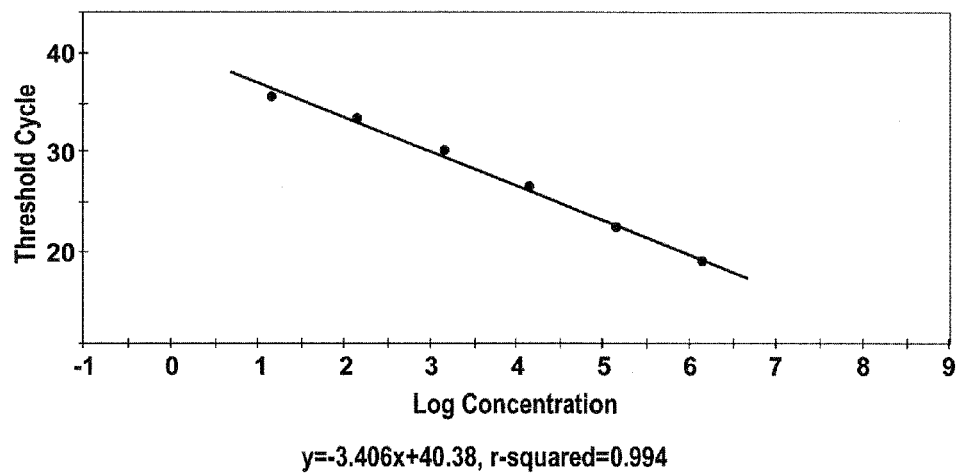
FIG. 4. DNA polymerase standard curve. The FHV-1 DNA polymerase standard curve was generated by testing six 10-fold serial dilutions of DNA polymerase standard RNA, and the theoretical limit of detection is 15 copies. The efficiency of the reaction was 97-100%, compared to the efficiency of 10-fold serial dilutions of DNA polymerase mRNA of 105% (not shown). Therefore, this standard curve was suitable for estimation of copy numbers of DNA polymerase mRNA.
Figure 5:
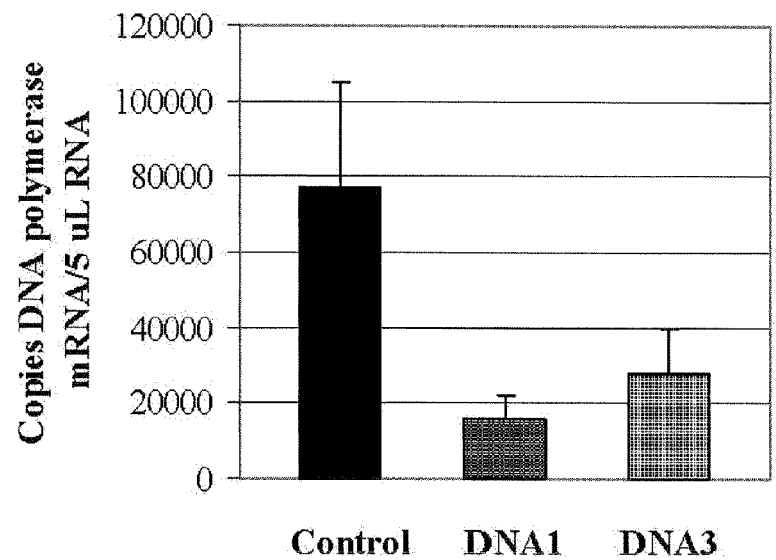
FIG. 5. Knockdown of FHV-1 DNA polymerase mRNA by siRNAs. CRFK cells were transfected with FHV-1 DNA polymerase specific siRNAs (DNA1 and DNA3) or negative control siRNA 24 h prior to infection with FHV-1 (MOI=0.1). Following 48 h incubation, total RNA was extracted from cells and tested by real-time RT-PCR with primers specific for DNA polymerase or 28S rRNA. The samples were normalized with 28S rRNA, and copies of DNA polymerase mRNA were estimated from a DNA polymerase standard curve generated by 10-fold serial dilutions of a DNA polymerase RNA standard. The results of three independent experiments show the means; error bars represent standard deviation from the mean. DNA1 (P=0.006) and DNA3 (P=0.015) are statistically different from the control based on univariate ANOVA analysis. Control=average of the results from non-treated and negative control siRNA-treated FHV-1 infected cells (not statistically different, P=0.33)
Figure 6:
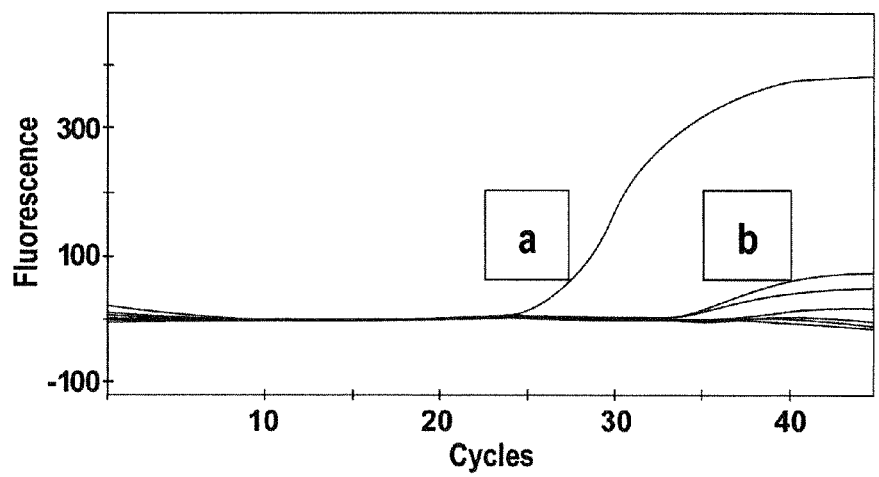
FIG. 6. Interferon β real-time RT-PCR. Knockdown of FHV-1 DNA polymerase mRNA is siRNA specific and not the result of type 1 interferon induction. Interferon β mRNA copy numbers in samples treated with DNA1/DNA3 (b) are similar to the copy numbers detected in the untreated samples (b) and are much lower than the copy numbers detected in cells infected with calicivirus (a), an interferon β inducer.

Knockdown of DNA polymerase mRNA by RNAi. Following the successful knockdown of GAPDH in CRFK cells by RNAi, we next evaluated RNAi directed against the DNA polymerase gene of FHV-1 in CRFK cells. CRFK cells were transfected separately with each of the five siRNAs designed to target the FHV-1 DNA polymerase mRNA or with negative control siRNA in six well plates 24 h prior to infection with FHV-1, and these samples were compared to a non-transfected, FHV-1 infected control. Forty-eight hours following infection, total RNA was extracted and tested for FHV-1 DNA polymerase mRNA by quantitative real-time RT-PCR. The RNA in each sample was normalized with 28S rRNA. Copies of mRNA were calculated from the standard linear curve (slope=−3.406), spanning six orders of magnitude, and resulted in a theoretical detection limit of 15 copies (FIG. 4). The results were reproducible, with intra-assays of variation of 6-15% based on copy numbers (0.33-0.91% based on Ct values) and inter-assays of variation of 14-21% based on copy numbers (0.73-1.44% based on Ct values) within the portion of the curve used to calculate DNA polymerase mRNA copies. Two of the five siRNAs tested produced significant reduction in DNA polymerase mRNA compared to the control, resulting in 83% reduction by DNA1 and 69% reduction by DNA3 (FIG. 5). RNAi knockdown of the DNA polymerase mRNA was independent of type 1 interferon production (FIG. 6).

Figure 7:
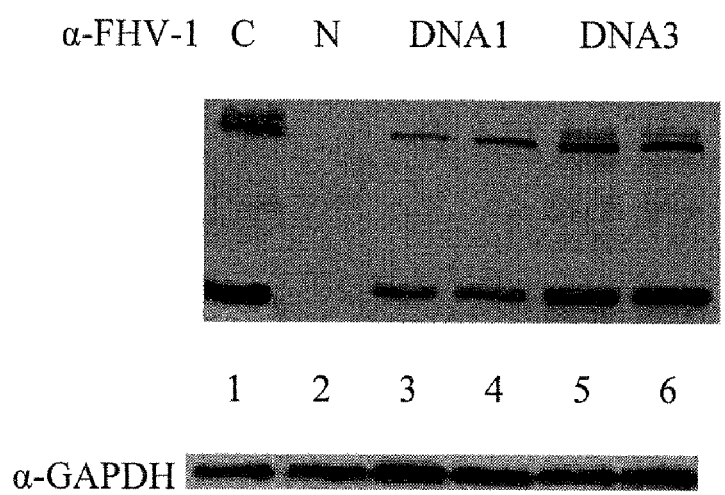
FIG. 7. FHV-1 DNA polymerase-specific siRNAs knockdown FHV-1 protein expression. Negative control siRNA (C) or FHV-1 DNA polymerase-specific siRNAs (DNA1/DNA3) were transfected into CRFK cells 24 h prior to infection with FHV-1 (MOI=0.1). Forty-eight hours following FHV-1 infection, total cellular material was electrophoresed on 10% SDS polyacrylamide gels. Proteins were transferred to nitrocellulose membranes, and membranes were probed with anti-FHV-1 polyclonal antibodies or an anti-GAPDH monoclonal antibody, as indicated (1—Negative control siRNA-treated, FHV-1 infected cells (N); 2—non-treated, non-infected cells (C); 3 & 4—duplicates of DNA1-treated, FHV-1 infected cells; 5 & 6—duplicates of DNA3 -treated, FHV-1 infected cells).
Figure 8A:
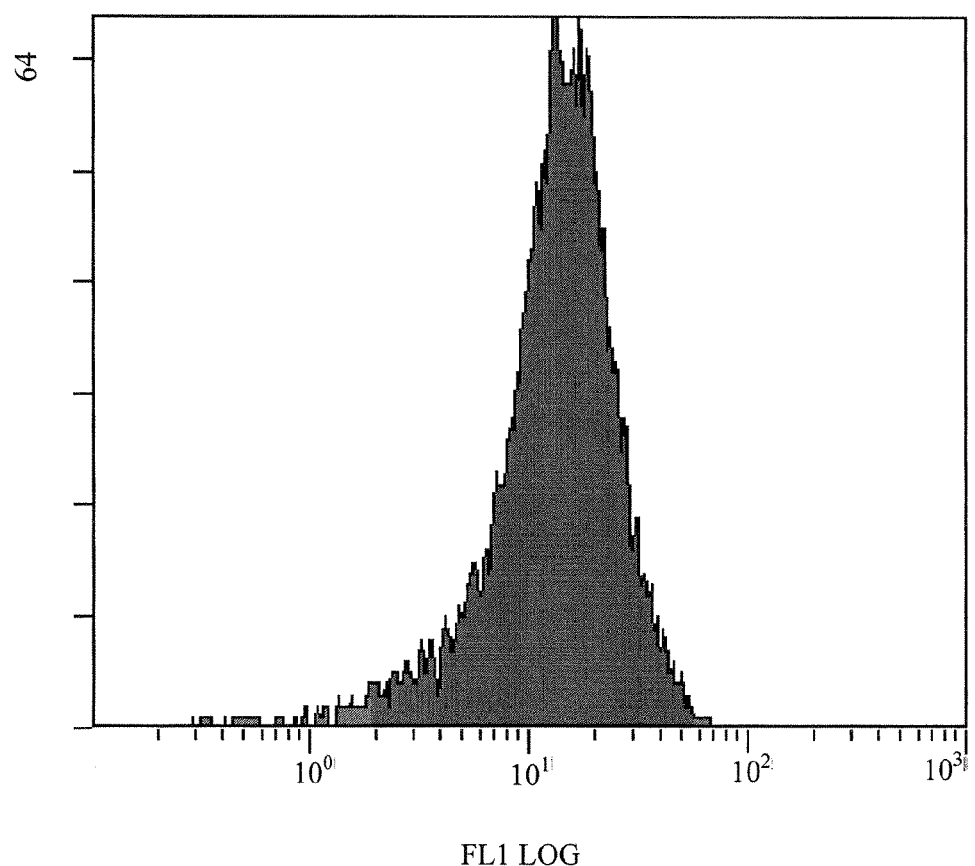
FIGS. 8A-D. FHV-1 DNA polymerase-specific siRNAs decrease expression of FHV-1 proteins on the surface of infected CRFK cells. Cells were transfected with negative control siRNA (FIG. 8A) or FHV-1 DNA polymerase-specific siRNA, DNA1 (FIG. 8B) or DNA3 (FIG. 8C), 24 h prior to FHV-1 infection (MOI=0.1). Forty-eight hours following infection, cells were incubated with anti-FHV-1 polyclonal antibodies. Fluorescence intensity increases from left to right, and $10^4$ cells/sample were analyzed. The data are representative of three independent experiments. Uninfected/non-transfected CRFK cells (FIG. 8D).
Figure 8B:
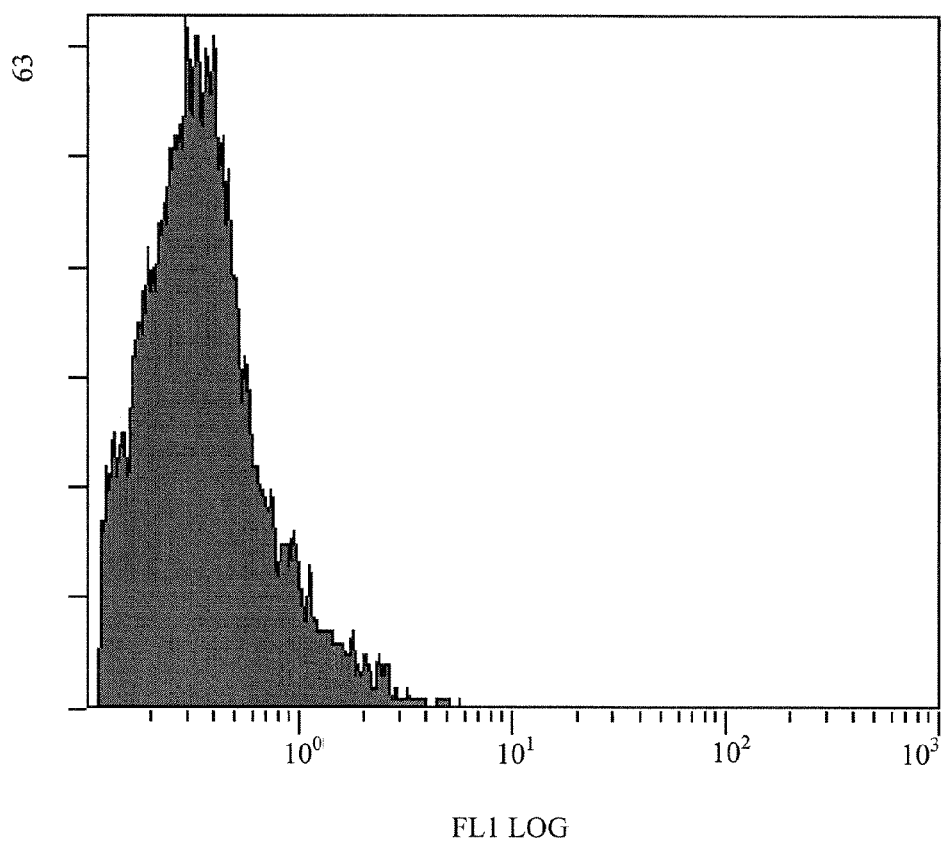
Figure 8C:
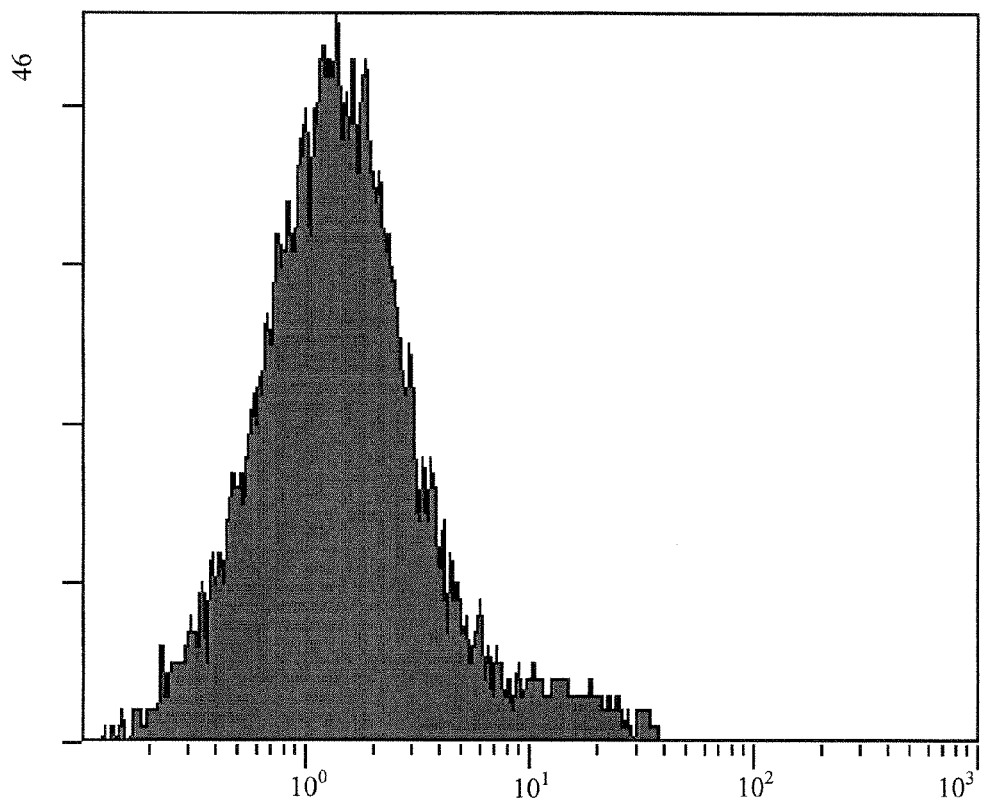
Figure 8D:
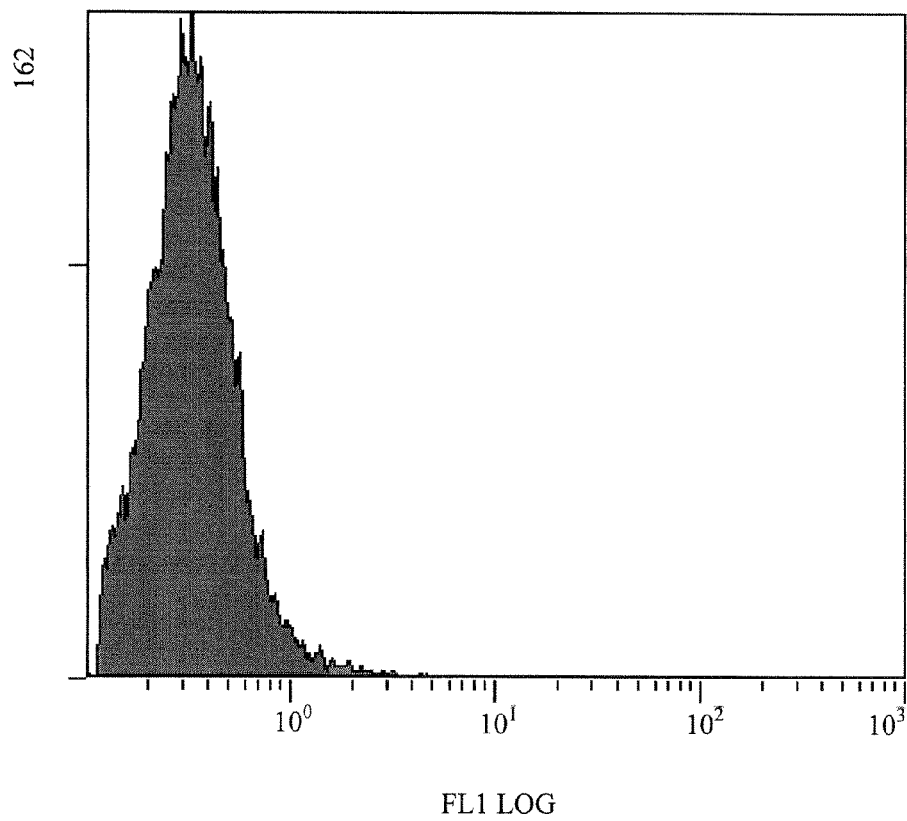

Reduction in FHV-1 protein expression by RNAi. Knockdown of FHV-1 DNA polymerase by DNA1 and DNA3 also resulted in decreased expression of FHV-1 proteins in treated cells compared to negative siRNA control treated cells and untreated, FHV-1 infected cells. Total protein was isolated from the infected cells and tested by Western blot (FIG. 7); cells were also tested by flow cytometry to determine the amount of FHV-1 proteins on the surface of FHV-1 infected, DNA polymerase-specific siRNA-treated cells versus FHV-1 infected, negative siRNA control-treated cells (FIG. 8). DNA1 reduced cell surface FHV-1 glycoproteins on infected cells by 71%, and DNA3 reduced cell surface FHV-1 glycoproteins by 29%, compared to the negative control siRNA-treated cells.

Figure 9:
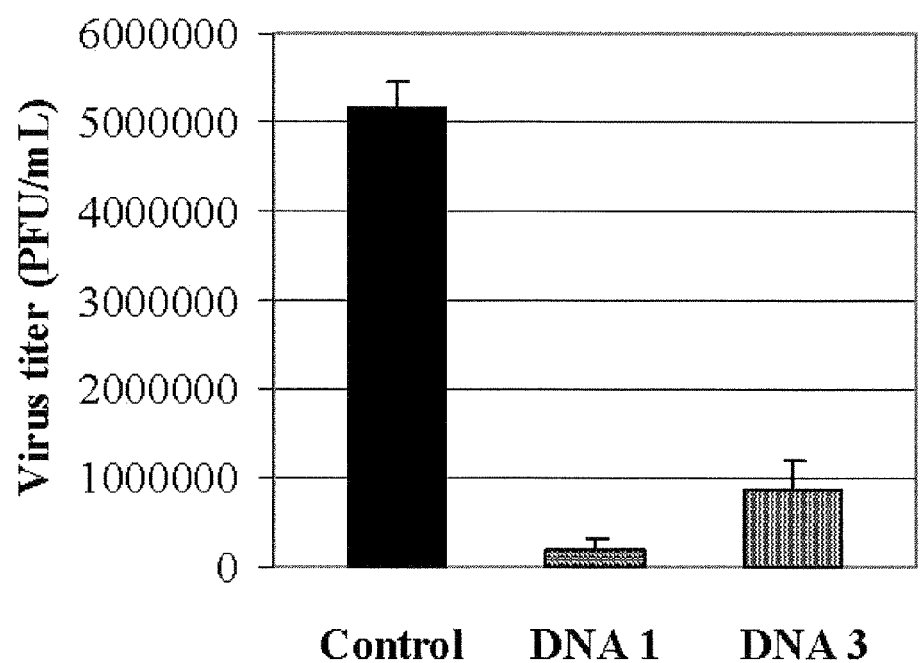
FIG. 9. FHV-1 DNA polymerase-specific siRNAs inhibit FHV-1 replication in CRFK cells. Cells were transfected with negative control siRNA or DNA polymerase-specific siRNA (DNA1/DNA3), 24 h prior to FHV-1 infection (MOI=0.1). Forty-eight hours following infection, cell culture supernatant was collected and tested in duplicate by plaque assay. The experiment was repeated three times, and the results are shown as averages from the three experiments, with error bars representing standard deviation from the mean. The titers from the DNA1- and DNA3-treated samples are statistically different from the titers for the untreated and negative siRNA-treated control samples (Control), with P values of <0.001 (univariate ANOVA).
Figure 10:
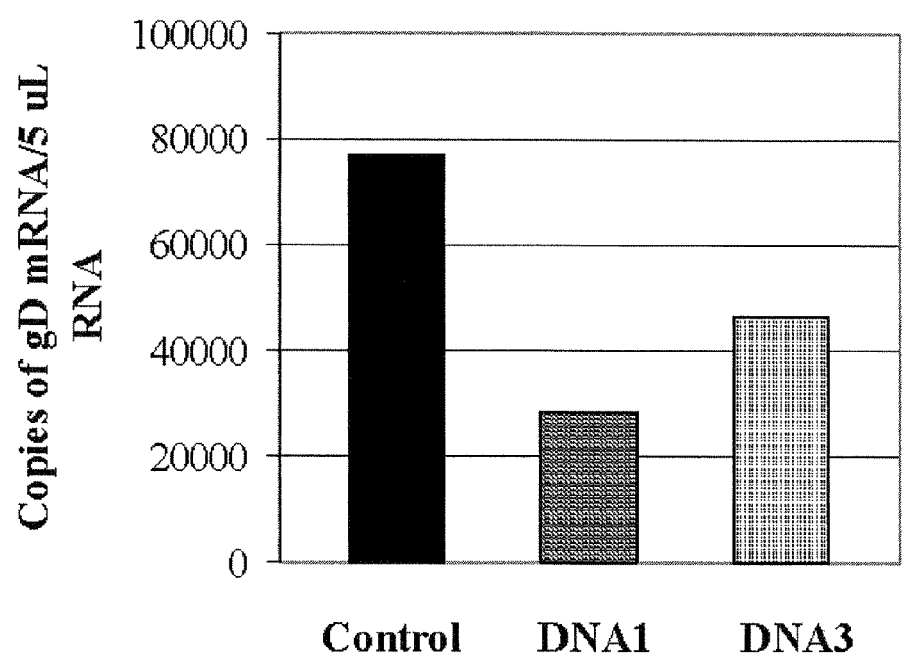
FIG. 10. Decreased FHV-1 glycoprotein D mRNA by DNA polymerase-specific siRNA treatment. CRFK cells were transfected with FHV-1 DNA polymerase-specific siRNAs (DNA1 or DNA3) or negative control siRNA 24 h prior to infection with FHV-1 (MOI=0.1). Following 48 h incubation, total RNA was extracted from cells and tested by real-time RT-PCR with primers specific for FHV-1 glycoprotein D mRNA (manuscript submitted). These results are from a single representative experiment.

FHV-1 DNA polymerase-specific siRNAs inhibit FHV-1 replication in vitro. As expected and suggested by the decreased viral protein expression in DNA1- and DNA3- treated cells, RNAi directed against FHV-1 DNA polymerase mRNA inhibited replication of the virus in CRFKs. Infectious FHV-1 was detected in the cell culture supernatants of siRNA-treated cells and controls by plaque assay. DNA1 siRNA inhibited FHV-1 replication by 96% and DNA3 by 83%, compared to the control (FIG. 9). Inhibition of replication was also evident by the indirect knockdown of the untargeted viral mRNA coding for glycoprotein D (FIG. 10).

Discussion

We used RNAi to target the DNA polymerase gene of FHV-1 and demonstrated significant suppression of viral replication by knockdown of the DNA polymerase mRNA. The virus, in the vast majority of cases, produces a localized respiratory infection (Crandell et al., 1961). Therefore, no systemic administration of siRNAs is necessary, eliminating the challenge of targeted delivery (although systemic delivery could also be used to deliver the siRNAs).

A potential benefit of using RNAi therapy for treatment of chronic FHV-1 ocular infections is the relatively long-term silencing obtained with RNAi. In this study, we showed knockdown that lasted at least 72 h after a single transfection. Therefore, unlike the current herpesvirus antiviral treatments which must be applied 4-6 times per day to be effective (Stiles, 1995), siRNAs could be used much less frequently. Silencing can be enhanced by consecutive applications of siRNAs into virus infected cells; however, this can lead to selection of mutants that have changes in the target region (Wilson et al., 2005), especially in chronic infections with RNA viruses that produce quasispecies populations (Kusov et al., 2006). However, due to lower mutation frequencies of DNA viruses like FHV-1, escape mutation is not expected to be a significant problem (Gitlin et al., 2003) and FHV-1 appears to have a low rate of genetic variability between isolates (Grail et al., 1991).

EXAMPLE 2

SIRNA Inhibition of FHV-1 Glycoprotein D

Materials and Methods

Cells and viruses. Crandell-Reese feline kidney (CRFK) cells (ATCC, Manassas, Va.) were propagated and maintained in Dulbecco's minimal essential medium (DMEM) (Cambrex, Charles City, Iowa) supplemented with 5% heat-inactivated fetal bovine serum (Atlanta Biologicals, Lawrenceville, Ga.) and standard concentrations of penicillin, streptomycin and Fungizone (Cambrex) at 37° C. in a 5% $CO_2$ incubator. The FHV-1 strain used was the prototype strain C-27 (ATCC). A calicivirus wild-type strain used in the study was a generous gift from the Clinical Virology Laboratory, University of Tennessee College of Veterinary Medicine.

siRNAs and transfection. Both 21-mer (Ambion-Applied Biosystems, Austin, Tex.) and 27-mer (IDT, Coralville, Iowa) siRNAs were used to target the glycoprotein D gene of FHV-1 (Table 3). The 21-mers and the 27-mers were compared with known sequences in the GenBank database to decrease off-target effects by avoiding similar sequences in the feline genome. Negative control 21-mer and 27-mer siRNAs were purchased from Ambion and IDT, respectively. A Cy-5-labeled control siRNA (IDT) was used as a transfection control. Transfections were performed with Lipofectamine 2000 (Invitrogen, Carlsbad, Calif.) in Opti-MEM (Gibco-Invitrogen), according to the manufacturer's protocol. Five µL of Lipofectamine 2000 was used to transfect 100 nM 21-mer siRNAs per well and 50 nM 27-mer siRNAs per well in six well plates. Approximately $5 \times 10^4$ CRFK cells diluted in DMEM, supplemented with 10% FBS, were added to each well containing the transfection mixtures. Plates were incubated for 24 h prior to infection with FHV-1. Each siRNA was tested in duplicate, and functional siRNAs were retested for a total of three experiments per siRNA. Additional controls used for each experiment included uninfected/non-transfected CRFK cells, infected/non-transfected cells, and an interferon β control, which consisted of non-transfected CRFK cells infected with feline calicivirus, an RNA virus that activates interferon β in CRFK cells.

Plaque assays. FHV-1 strain C-27 was grown in CRFK cells until a 50% cytopathic effect was produced. The titer of the virus was determined by plaque assay as previously described (Burleson et al., 1992), with the exception of using an agarose overlay. Instead, serum from a cat with an IFA titer of >1:2560 (a gift from the University of Tennessee Clinical Virology Lab) was used at a dilution of 1:50.

Transfected CRFK cells were infected with FHV-1 at a multiplicity of infection (MOI) of 0.1. One hour after incubation, the cells were washed with DMEM, and fresh DMEM supplemented with 10% FBS was added to each well. Infected cells were incubated for a total of 48 h, after which 500 µL of cell culture medium was removed from each well and stored at −80° C. for plaque assay. Infective virus titers (PFU) were determined for each well by plaque assay.

Flow cytometry. Prior to infection with FHV-1, (24 h after transfection) the transfection control well was tested to determine transfection efficiency. The cells were trypsinized, washed in phosphate buffered saline (PBS) (Gibco-Invitrogen) and flow buffer (60 mL 0.5% sodium azide solution, 87 mL PBS, and 3 mL FBS), and resuspended in 1 mL PBS. Transfection efficiency was determined by analyzing intracellular Cy-5 fluorescence with a Beckman Coulter Epics XL flow cytometer (Fullerton, Calif.). Following FHV-1 infection and 48 h incubation, the cells in each test and control well were trypsinized, washed with PBS, and resuspended in 1 mL of PBS per sample. 100 µL of each suspension was removed and placed on ice for RNA extraction, and the rest of each sample was processed for flow cytometry. The flow cytometry samples were washed in flow buffer, divided in half, and the cells were pelleted. Half of each sample was stained with 200 µL fluorescein isothiocyanate-labeled, anti-FHV-1 polyclonal antibody (Accurate Chemical and Scientific Corp., Westbury, N.Y.), and the remainder was stained with the primary monoclonal antibody FHV 7-5, a generous gift from Dr. Chris Grant (Custom Monoclonals International, Sacramento, Calif.) at a dilution of 1:50 in PBS for 1 h on ice. The cells were then washed, and the cells treated previously with the primary antibody were treated with 2 µL of the secondary antibody, fluorescein isothiocyanate-labeled F(ab')$_2$ rabbit anti-mouse immunoglobulin G (Southern Biotech, Birmingham, Ala.) for 1 h on ice. The cells treated with the polyclonal antibody were resuspended in 1 mL PBS per sample and stored at 4° C. until analyzed. After a final wash for the remaining cells, they were resuspended in 1 mL PBS per sample, and all the samples were analyzed by flow cytometry.

RNA extraction and real-time RT-PCR. Total RNA was extracted from 100 µL aliquots of each test and control sample with the RNeasy Mini Kit (Qiagen, Valencia, Calif.) according to the manufacturer's protocol. The RNA samples were treated with two on-column DNase digestions (Qiagen) and diluted 1:1000 to reduce DNA contamination. Purified RNA samples were stored at −80° C. until tested by real-time reverse-transcription polymerase chain reaction (RT-PCR). Primers and probes for real-time RT-PCR were developed with Primer3 (Rozen et al., 2000) to detect FHV-1 glycoprotein D and interferon β mRNA (Table 4). 28S rRNA was used as a control to standardize RNA concentration (Table 4). Real-time RT-PCR was performed for each transcript using the SuperScript III Platinum One-Step qRT-PCR kit (Invitrogen) in a SmartCycler® II (Cepheid, Sunnyvale, Calif.). Five μL of diluted RNA was used in 25 μL total volume reactions, which contained 200 nM of each probe and 300 nM of each primer. The reaction conditions for glycoprotein D and interferon β were reverse transcription at 42° C. for 30 min, an initial heat step of 95° C. for 2 min to activate the hot start Taq polymerase, followed by 45 cycles of 95° C. for 15 s, 50° C. (glycoprotein D) or 60° C. (interferon β) for 60 s, and 72° C. for 30 s. The reaction conditions for 28S rRNA were reverse transcription at 50° C. for 30 min, 95° C. for 2 min, and 45 cycles of 95° C. for 15 s, 62° C. for 60 s, and 72° C. for 30 s. RTase negative controls were run using Platinum Taq (Invitrogen), replacing SuperScript III, to rule out excessive DNA contamination. Each set of samples was run with mRNA standard dilutions to validate mRNA quantitation.

mRNA standards and standard curve production. mRNA standards were produced for glycoprotein D and interferon β by cloning the PCR products into plasmid vectors and transducing *Escherichia coli* (TA Cloning Kit, Invitrogen). Recombinant plasmids were isolated (SNAP MiniPrep Kit, Invitrogen), sequenced (Molecular Biology Resources Service, University of Tennessee, Knoxville, Tenn.), linearized (Hind III, Fisher Scientific), and used for in vitro transcription (AmpliCap T7 High Yield Message Maker Kit, Epicentre Biotechnologies, Madison, Wis.). mRNA transcripts were treated with DNase (Qiagen) and purified (RNeasy Mini Kit, Qiagen). These standards were used to produce standard curves for absolute quantitation of glycoprotein D and interferon β mRNA transcripts isolated from the samples. The RNA concentration and purity of the mRNA standards was determined with a BioPhotometer 6131 spectrophotometer (Eppendorf, Westbury, N.Y.). The numbers of RNA copies were estimated based on the molecular weights of the RNA standards and the RNA concentrations. Ten-fold serial dilutions were prepared, and aliquots of each dilution were stored at −80° C. and used only once.

Standard curves were generated by testing dilutions of the standard RNAs by real-time RT-PCR, by using SmartCycler® II software (Cepheid). The intra-assay and inter-assay coefficients of variation of the reactions were determined using dilutions of the standard RNAs as previously described (Stelzl et al., 2004). To ensure the standard RNAs and the target RNAs were amplified with similar efficiencies (based on the calculation: Efficiency=$[10^{-1/slope}]-1$) (Wong et al., 2005), four 10-fold serial dilutions of RNA extracted from an FHV-infected control well and RNA extracted from a Calici-infected interferon β control well were also prepared and tested by real-time RT-PCR.

Results

FHV-1 glycoprotein D specific-siRNA inhibits glycoprotein D mRNA and protein expression. To examine whether glycoprotein D expression could be knocked down by RNA interference, three 27-mer and three 21-mer siRNAs were designed to target five different areas of glycoprotein D mRNA. The siRNAs were transfected into cells prior to infection with FHV-1. CRFK cells were effectively transfected with Lipofectamie 2000, with efficiencies of 95% and greater, based on results from a transfection control siRNA (data not shown).

Figure 11:
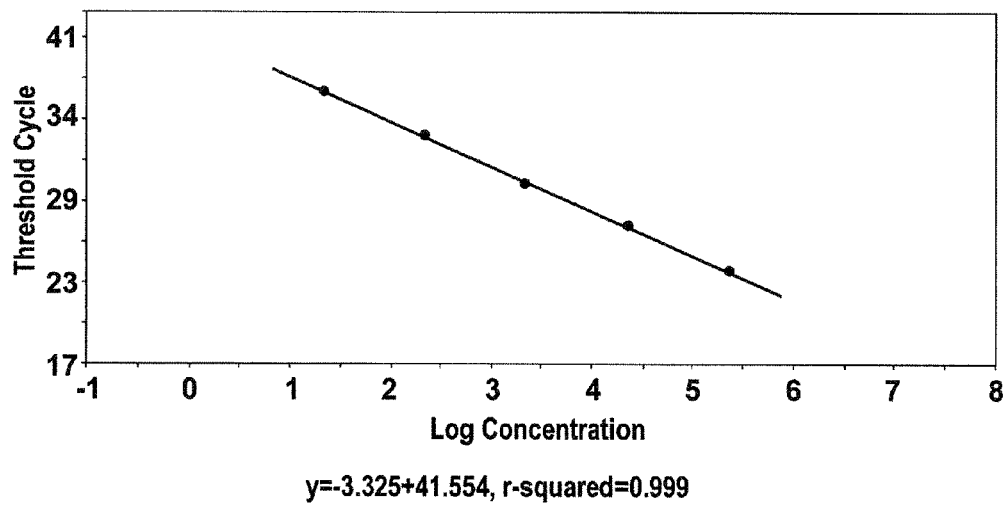
FIG. 11. FHV-1 glycoprotein D standard curve. The curve was generated by testing five 10-fold serial dilutions of glycoprotein D standard RNA. The efficiency of the reaction was 100%, compared to the efficiency of 10-fold serial dilutions of glycoprotein D mRNA of 101% (not shown). Therefore, this standard curve is suitable for estimation of copy numbers of glycoprotein D mRNA.

Quantitative real time RT-PCR was used to determine glycoprotein D mRNA knockdown 48 h after infection. mRNA copy numbers for each sample were estimated from a standard curve generated by dilutions of standard glycoprotein D RNA. The standard curve spanned five orders of magnitude, and the curve showed linearity over the entire range used for quantitation of mRNA (FIG. 11). The results were reproducible, with an intra-assay coefficient of variation based on copy numbers of 10-21% (0.5-1.24% based on Ct values) and an inter-assay coefficient of variation of 34-52% based on copy numbers (1.33-3.40% based on Ct values). The theoretical limit of detection was 20 copies of glycoprotein D mRNA.

Figure 12:
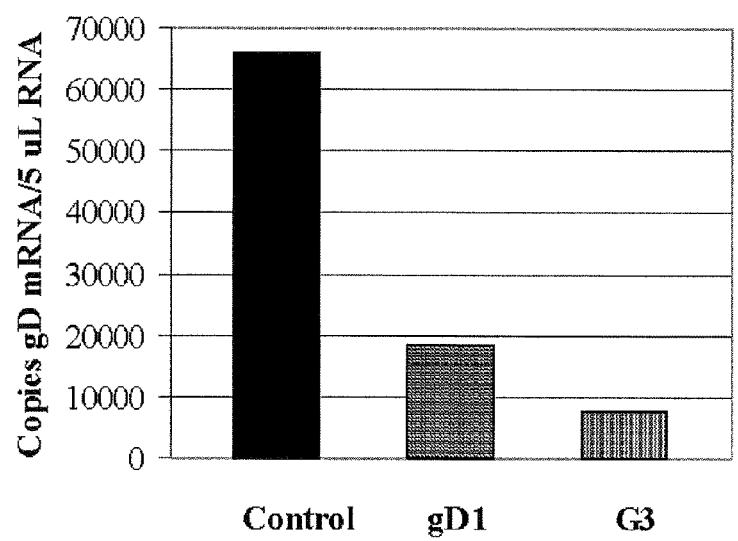
FIG. 12. Knockdown of FHV-1 glycoprotein D mRNA by siRNAs. CRFK cells were transfected with negative control siRNA, gD1 siRNA, or G3 siRNA 24 h prior to infection with FHV-1 (MOI=0.1). Following 48 h incubation, total RNA was extracted from cells and tested by real-time RT-PCR with primers specific for glycoprotein D or 28S rRNA. The samples were normalized with 28S rRNA, and copies of glycoprotein D were estimated from the glycoprotein D standard curve. The figure shows the results from a single representative experiment. Three independent experiments were performed with similar results. Control averaged results from 21-mer and 27-mer negative control siRNA treated FHV-1 infected cells (not statistically different, P=0.26 univariant ANOVA), gD1/G3=FHV-1 glycoprotein D-specific siRNAs FIG. 13. Detection of FHV-1 glycoprotein D with FHV 7-5 monoclonal antibody. Proteins from FHV-1 infected cells were treated with SDS sample buffer, electrophoresed on a 10% polyacrylamide gel and transferred to a nitrocellulose membrane (Bio-Rad, Hercules, Calif.). The membrane was blocked overnight in 5% milk at 4° C. and then probed with FHV 7-5 monoclonal antibody for 1 h on a shaker at room temperature. The membrane was washed five times with PBS containing 0.05% Tween 20 and probed with peroxidase-labeled goat anti-mouse IgG (KPL, Gaithersburg, Md.) for 1 h on a shaker at room temperature. Five additional washes were performed, and the protein was detected by enhanced chemiluminescence (Amersham Biosciences, Piscataway, N.J.).

Of the siRNAs tested, one of the 27-mers (gD1) and one of the 21-mers (G3) were shown to be highly effective, with knockdown of glycoprotein D mRNA by 77% (gD1) and 87% (G3), whereas the rest of the siRNAs were shown to have minimal to moderate effects compared to control samples transfected with negative control siRNAs (FIG. 12 and data not shown). The least functional siRNAs, producing approximately 30% knockdown each, were the 27-mer gD2 and the 21-mer G1, which both targeted the same region of the coding sequence (data not shown). gD1 and G3 siRNAs were also tested in cells infected with FHV-1 (MOI=1) 24 h following transfection and tested for mRNA knockdown 24 h following infection. G3 was effective under these reaction conditions. The 27mer gD1 was less effective (data not shown) than G3 and also reduced glycoprotein D mRNA levels.

Figure 13:
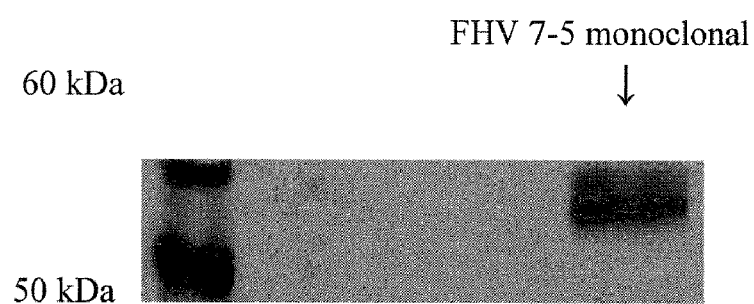
Figure 14:
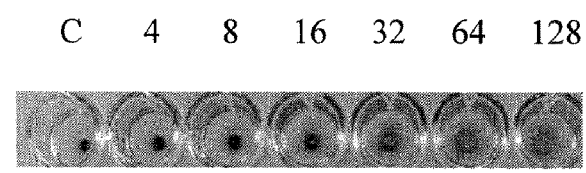
FIG. 14. Inhibition of FHV-1 hemagglutination by FHV 7-5. A hemagglutination inhibition test was performed with monoclonal FHV 7-5 and treated FHV-1-infected CRFK cells by using 0.5% (v/v) feline red blood cells as previously described (Maggs et al., 1999). C represents the control well, which lacked FHV-1, and the numbers represent the inverse of two-fold serial dilutions of antibody.
Figure 15A:
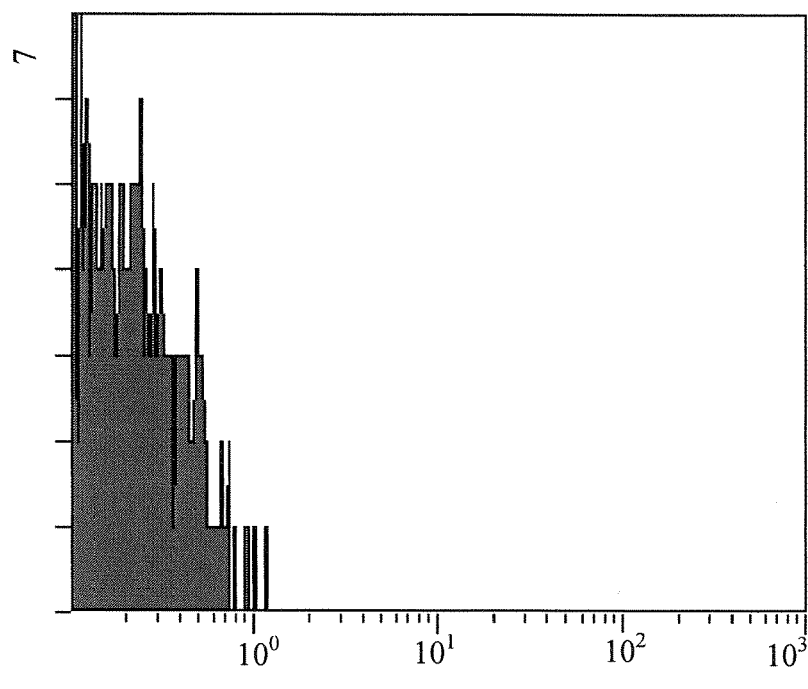
FIGS. 15A-15F. FHV-1 glycoprotein D specific siRNAs knockdown expression of gD protein on the surface of infected CRFK cells. Cells were transfected with G3 (FIG. 15B), gD1 (FIG. 15E), or negative control siRNA (FIGS. 15C and 15F) 24 h prior to FHV-1 infection (MOI=0.1). Forty-eight hours following infection, cells were incubated with FHV 7-5 monoclonal antibody (gD specific monoclonal) and FITC-labeled (ab')$_2$ rabbit anti-mouse immunoglobulin G. Fluorescence intensity increases from left to right, and $10^4$ cells were analyzed per sample. This experiment was repeated three times with similar results.
Figure 15B:
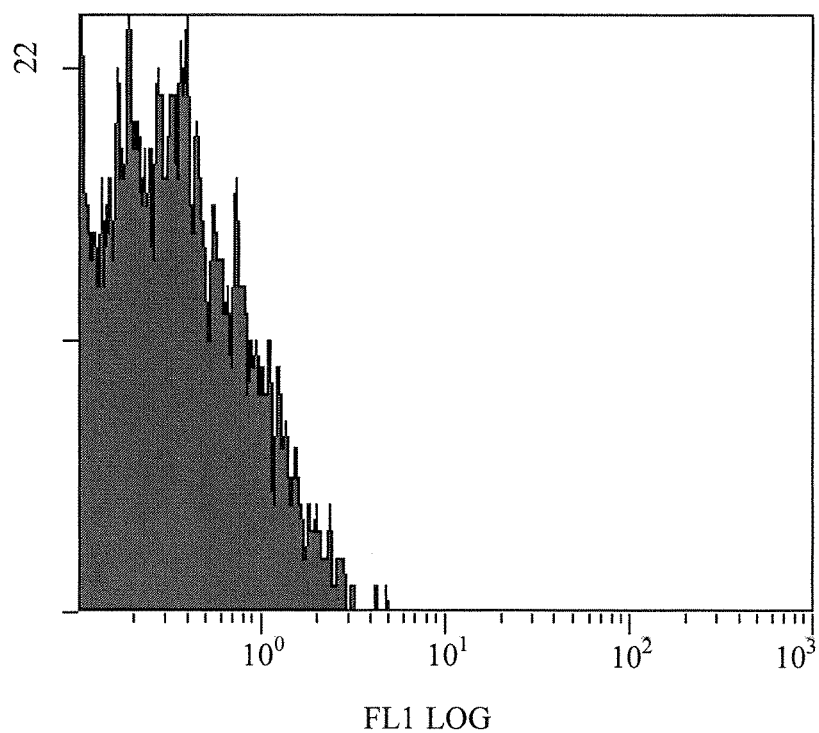
Figure 15C:
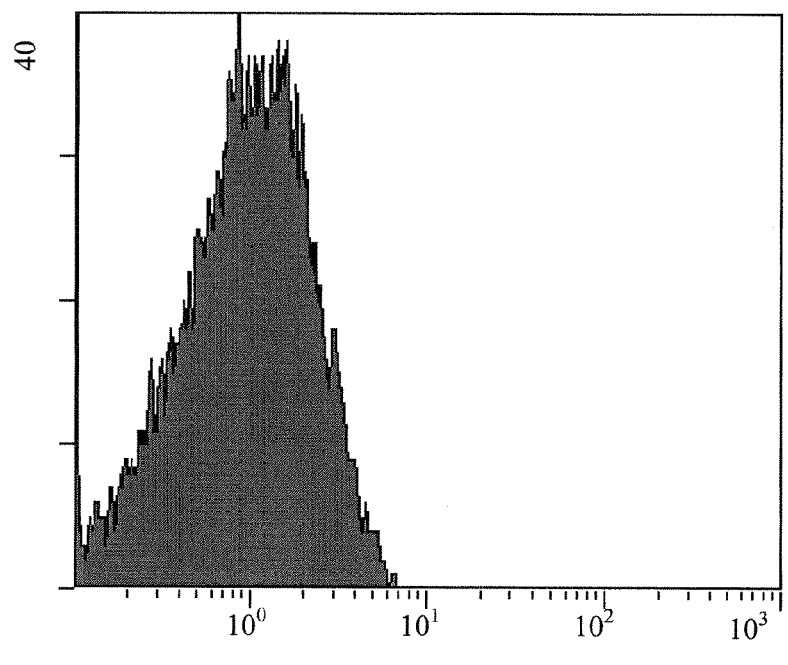
Figure 15D:
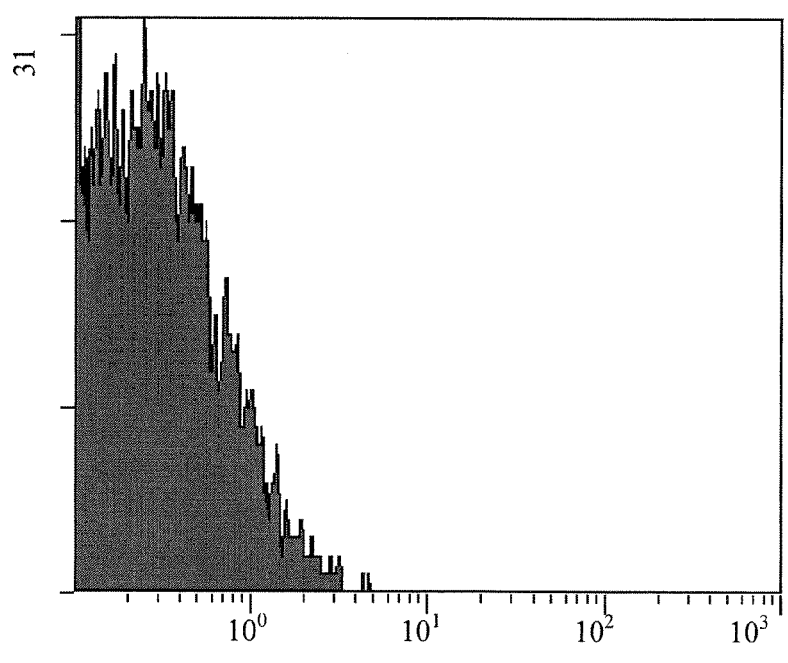
Figure 15E:
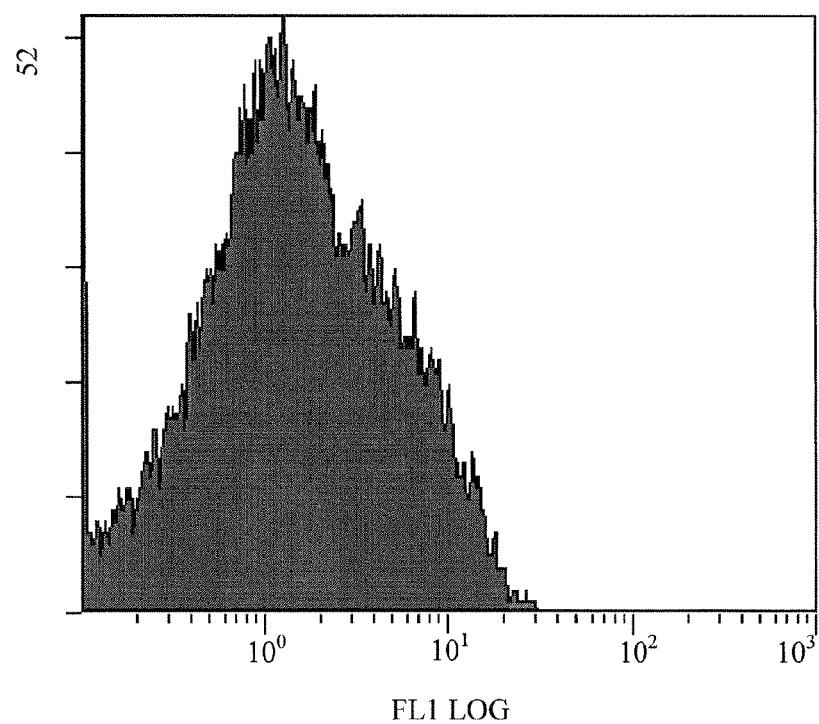
Figure 15F:
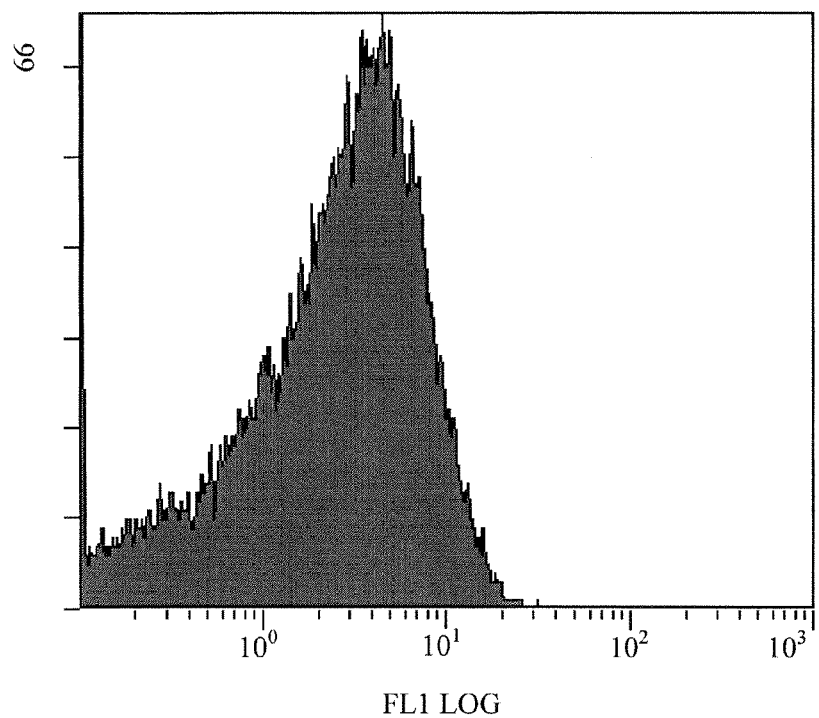

Glycoprotein D protein synthesis was assessed in glycoprotein D-specific siRNA-treated cells versus negative siRNA-treated cells by flow cytometry. For this test, FHV-1 monoclonal antibodies, donated by Dr. Chris Grant (Custom Monoclonals International), were characterized by Western blot analysis, flow cytometry, virus neutralization, and hemagglutination inhibition assays. One monoclonal antibody (FHV 7-5) was shown to react with an antigen that is approximately 50-60 kDa in size (FIG. 13), found on the surface of infected cells by flow cytometry, and inhibited hemagglutination of feline cells (FIG. 14). These results suggested this monoclonal antibody detects FHV-1 glycoprotein D (Maeda et al., 1998; Maeda et al., 1994). However, FHV 7-5 did not neutralize virus infectivity in the absence of complement as expected, but this is a variable characteristic based on epitope (Maeda et al., 1994). Therefore, FHV 7-5 was used to assess the amount of glycoprotein D present on the surface of FHV-1 infected cells transfected with negative control siRNA or with glycoprotein D-specific siRNAs. Knockdown of glycoprotein D by gD1 and G3 siRNAs decreased glycoprotein D protein expression by 27% and 43%, respectively, compared to the negative siRNA transfected control (FIG. 15).

Figure 16:
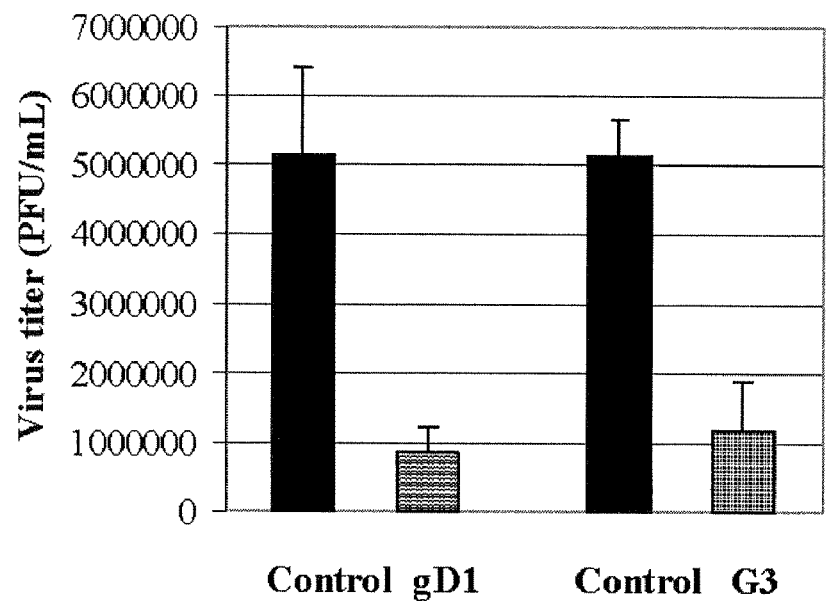
FIG. 16. FHV-1 glycoprotein D-specific siRNAs inhibit FHV-1 replication in CRFK cells. Cells were transfected with negative control siRNA, gD1, or G3 24 h prior to FHV-1 infection (MOI=0.1). Forty-eight hours following infection, cell culture supernatant was collected and tested in duplicate by plaque assay. The experiment was repeated three times, and the results shown are averages from the three experiments, with error bars representing standard deviation from the mean. The titers from the gD1- and G3-treated samples are statistically different from the titers for the negative siRNA-treated and untransfected control samples (Control), with P values of 0.005 and 0.003, respectively (univariant ANOVA).

FHV-1 glycoprotein D-specific siRNAs inhibit virus replication. To determine whether knockdown of glycoprotein D mRNA affects virus replication, plaque assays were performed to quantify the amount of infective virus released into cell culture supernatants. gD1 was shown to inhibit viral replication by 84%, and G3 inhibited viral replication by 77%, compared to non-transfected and negative control siRNA-transfected, FHV-1 infected cells (FIG. 16)

Figure 17:
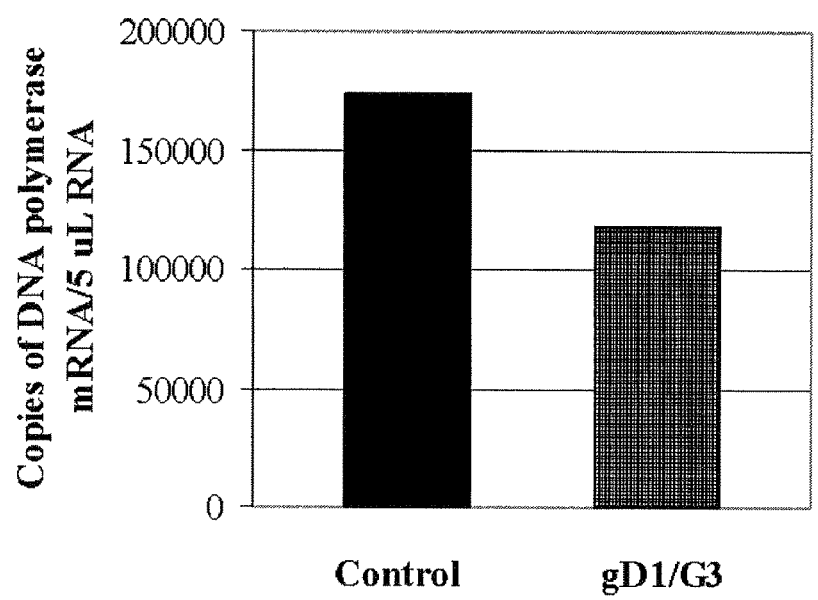
FIG. 17. Indirect decrease of FHV-1 DNA polymerase mRNA by glycoprotein D-specific siRNAs. CRFK cells were transfected with FHV-1 glycoprotein D specific siRNAs (25 nM gD1 siRNA and 75 nM G3 siRNA) or negative control siRNAs (25 nM 27-mer control, 75 nM 21-mer control) 24 h prior to infection with FHV-1 (MOI=0.1). Following 48 h incubation, total RNA was extracted from cells and tested by real-time RT-PCR with primers specific for DNA polymerase mRNA (see Part 2) or 28S rRNA. The samples were normalized with 28S rRNA, and copies of DNA polymerase mRNA were estimated from a DNA polymerase standard curve generated from 10-fold serial dilutions of DNA polymerase standard RNA (manuscript submitted).
Figure 18A:
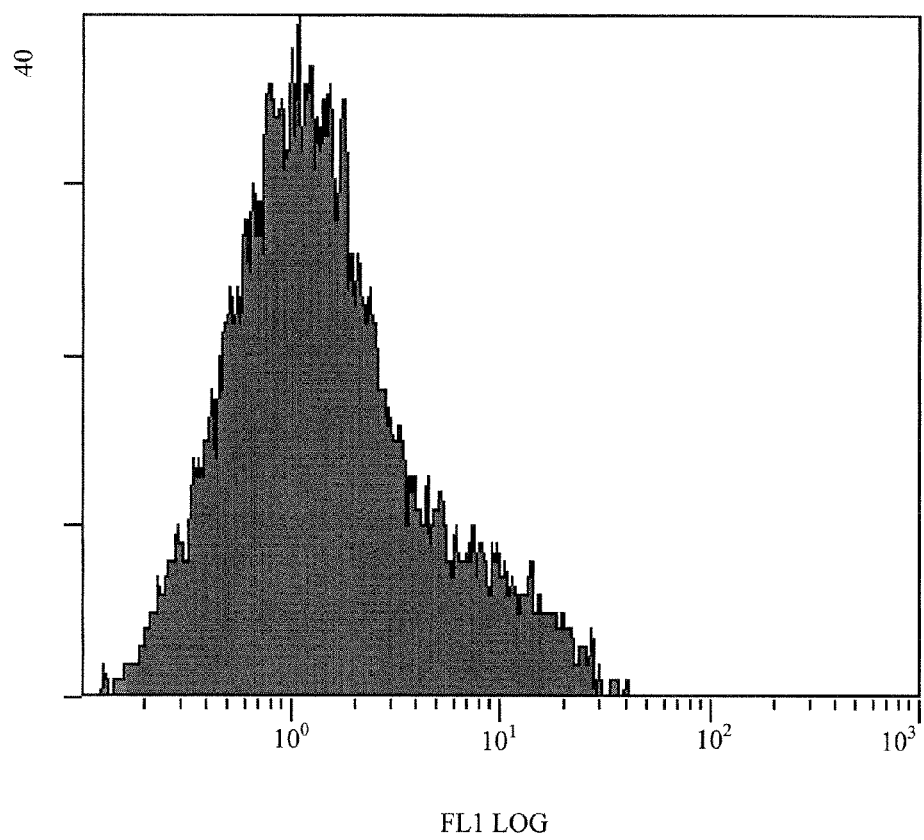
FIGS. 18A-18C. FHV-1 glycoprotein D-specific siRNAs knockdown FHV-1 proteins on the surface of infected CRFK cells. CRFK cells were transfected with FHV-1 glycoprotein D-specific siRNAs (FIG. 18A) (25 nM gD1 siRNA and 75 nM G3 siRNA) or negative control siRNAs (FIG. 18B) (25 nM 27-mer control and 75 nM 21-mer control) 24 h prior to infection with FHV-1 (MOI=0.1). Following 48 h incubation, cells were incubated with fluorescein isothiocyanate-labeled, anti-FHV-1 polyclonal antibody (Accurate Chemical and Scientific Corp., Westbury, N.Y.). Uninfected CRFK cells (FIG. 18C).
Figure 18B:
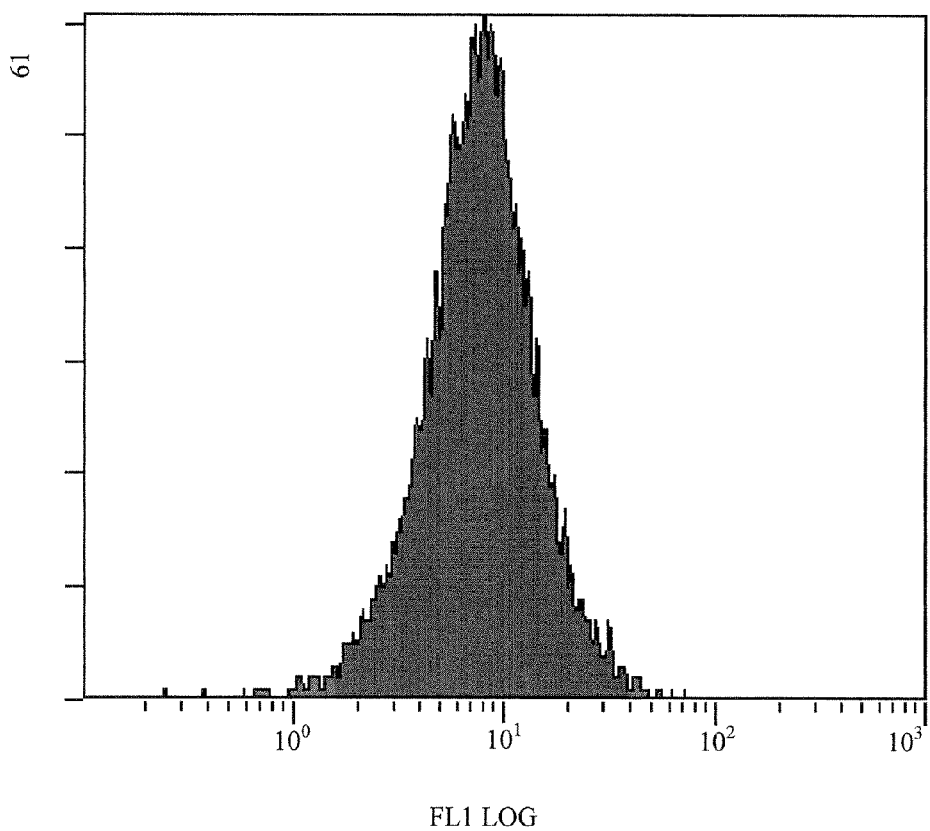
Figure 18C:
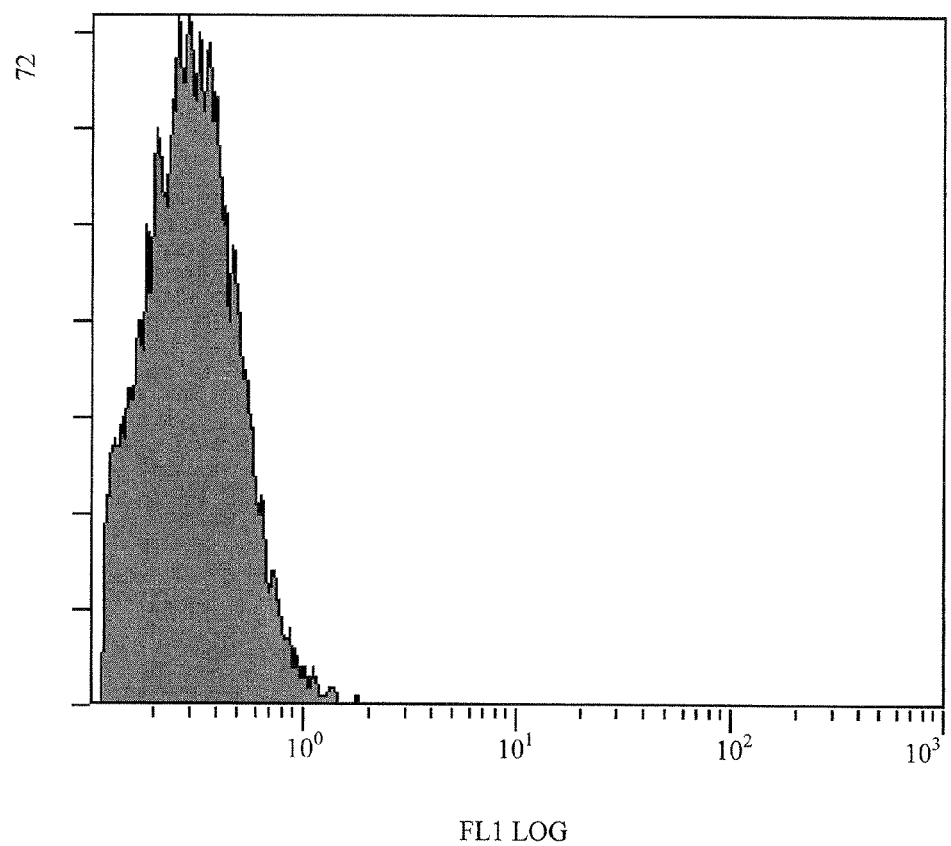
Figure 19:
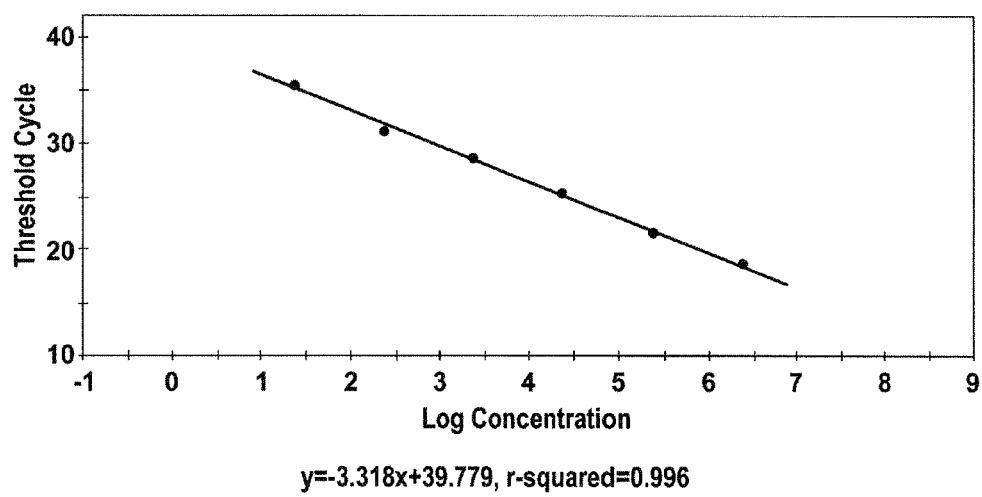
FIG. 19. Interferon β standard curve. The curve was generated by testing six 10-fold serial dilutions of interferon β standard RNA. The efficiency of the reaction was 100%, compared to the efficiency of 10-fold serial dilutions of interferon β mRNA of 96% (not shown). This standard curve was used for estimation of copy numbers of interferon β mRNA, with a theoretical detection limit of 25 copies of RNA.
Figure 20A:
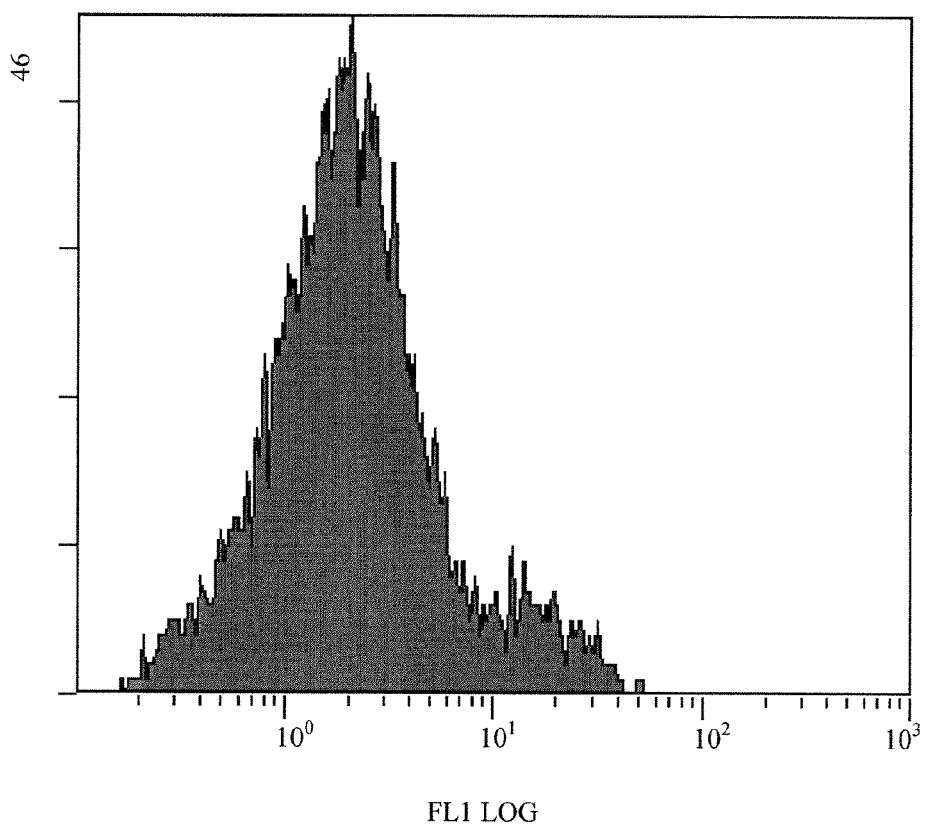
FIGS. 20A-D. Combinations of siRNAs targeting essential genes of FHV-1 decrease expression of FHV-1 proteins on the surface of infected cells. Pre-plated cells were transfected with negative control siRNA (FIG. 20A) or combinations of siRNAs, including DNA1/gD1 (FIG. 20B) and DNA1/DNA3 (FIG. 20C), 24 hours prior to FHV-1 infection (MOI=0.1). Forty-eight hours following infection, cells were incubated with anti-FHV-1 polyclonal antibodies. Fluorescence intensity increases from left to right, and $10^4$ cells/sample were analyzed. The data are representative of two independent experiments. Uninfected/non-transfected CRFK cells (FIG. 20D).
Figure 20B:
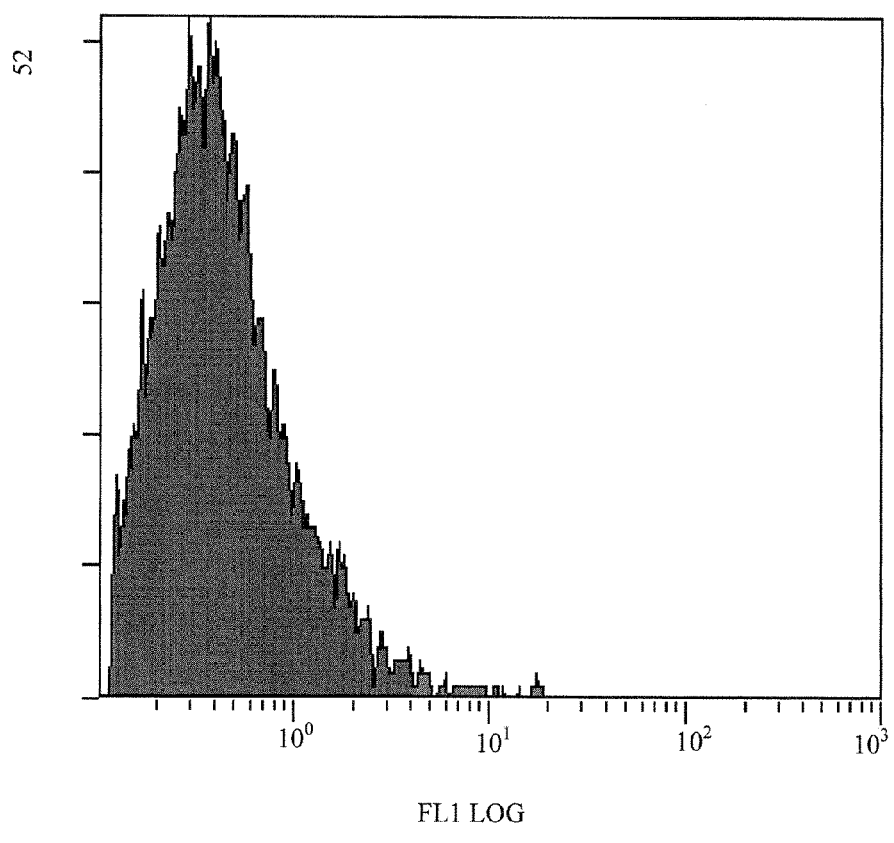
Figure 20C:
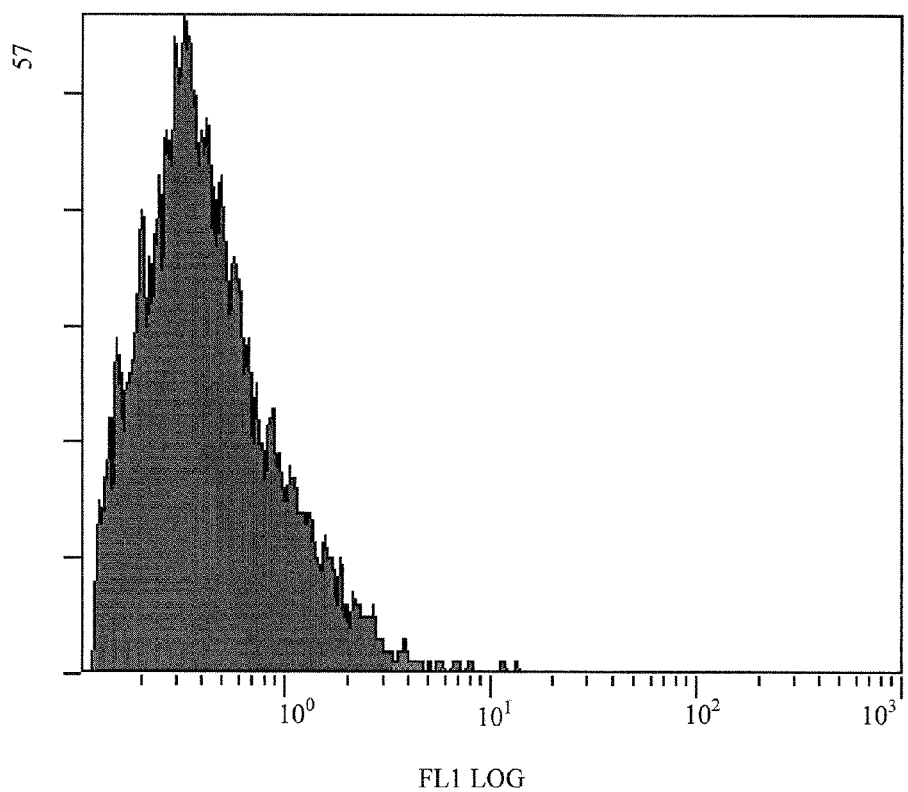
Figure 20D:
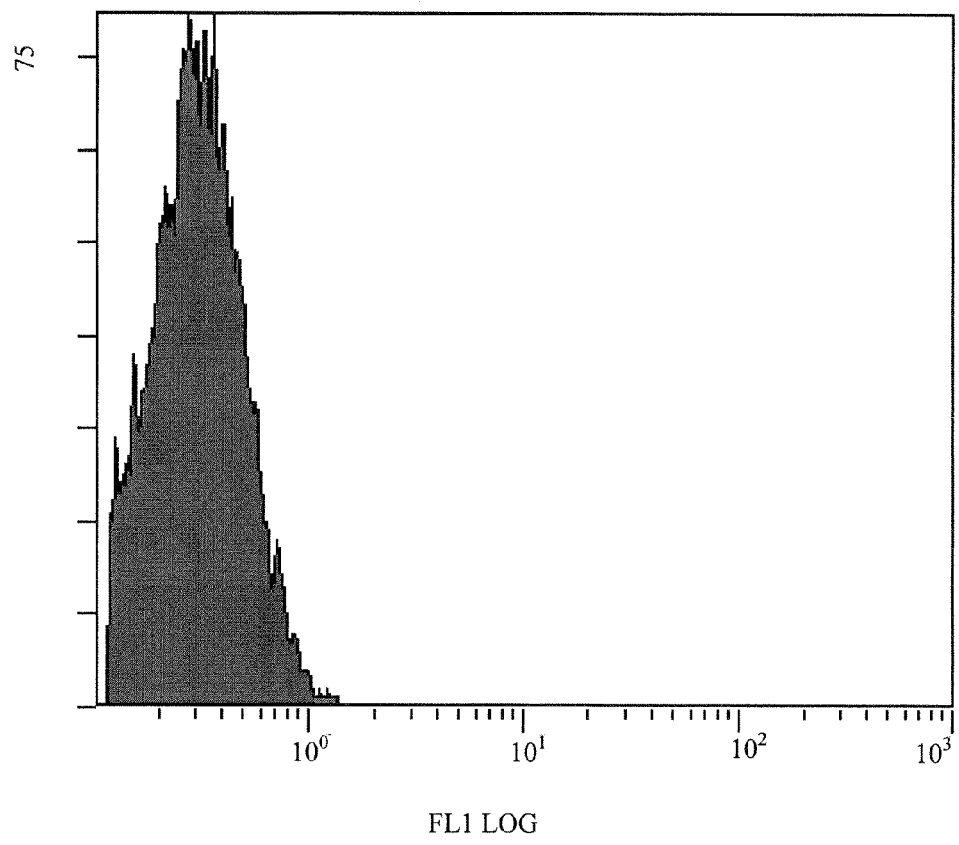
Figure 21:
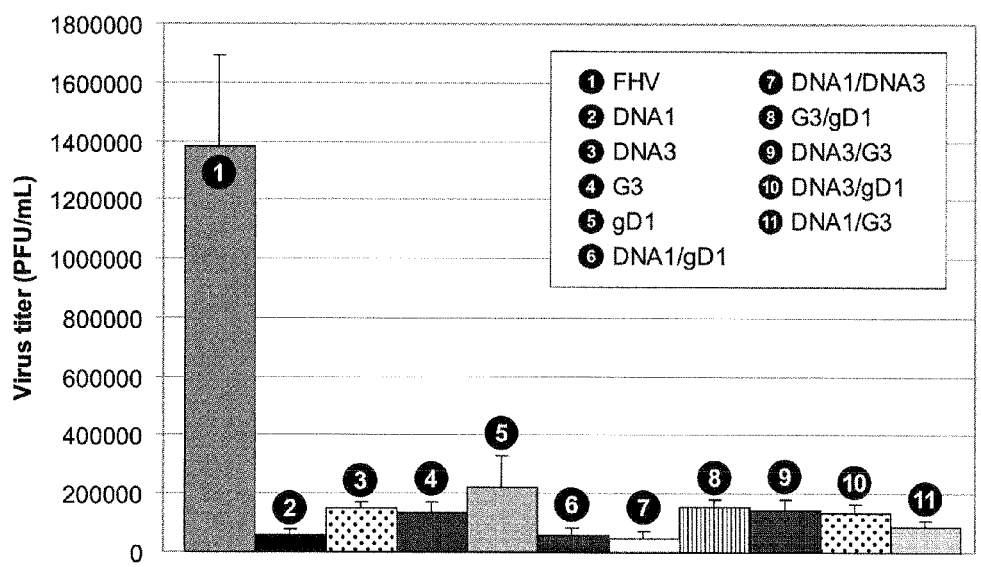
FIG. 21. Combinations of siRNAs targeting FHV-1 DNA polymerase and glycoprotein D inhibit viral replication in CRFK cells. Pre-plated cells were transfected with combinations of siRNAs targeting FHV-1 DNA polymerase and/or glycoprotein D 24 hours prior to FHV-1 infection (MOI=0.1). Combinations of two siRNAs (50 nM each) were used per well. Each combination was tested in duplicate. Forty-eight hours following infection, cell culture supernatant was collected and tested by plaque assay. The experiment was repeated twice, and the results are shown as averages from the experiments, with error bars representing one standard deviation from the mean. Each treatment was statistically different from the non treated control, with DNA1, DNA1/DNA3, and DNA1/gD1 producing the best reduction in viral replication. These three treatments are not statistically different from each other, based on paired post hoc tests to compare between treatment groups, with alpha held to a simultaneous value of 0.05.

Glycoprotein D specific siRNAs inhibit FHV-1 DNA polymerase mRNA. Based on the results from the replication study, we expected that interference of glycoprotein D mRNA should also result in an indirect decrease in all viral mRNAs due to replication inhibition. So, the effect of gD1 and G3 treatment on FHV-1 DNA polymerase mRNA copy numbers was determined. The RNA extracted from the cells was tested for FHV-1 DNA polymerase mRNA by real-time RT-PCR with primers specific for FHV-1 DNA polymerase mRNA (manuscript submitted). Though no significant decline in the DNA polymerase mRNA was detected from samples treated individually with gD1 or G3, when the siRNAs were used together (25 nM gD1, 75 nM G3) to transfect cells 24 h prior to FHV-1 infection (MOI=0.1), a decrease in the DNA polymerase mRNA was detected (FIG. 17 and data not shown).

Glycoprotein D-specific siRNAs inhibit expression of additional cell surface proteins. Knockdown of additional FHV-1 proteins by glycoprotein D-specific siRNAs was also evaluated. Known glycoproteins on the surface of FHV-1 infected cells in addition to glycoprotein D include glycoproteins B, C, and G, and the complex formed by glycoproteins E and I. Polyclonal antibodies of feline origin were used to evaluate the potential knockdown of additional glycoproteins in flow cytometry experiments. gD1 and G3, when used independently, did not display much effect on the other glycoproteins; however, when used in combination (25 nM gD1, 75 nM G3), they produced significant knockdown in surface FHV-1 glycoproteins on infected cells compared to negative control siRNA-transfected, FHV-1 infected cells (FIG. 18 and data not shown).

The siRNA effect produced by glycoprotein D-specific siRNAs is specific. The effect of virus replication suppression by knockdown of the glycoprotein D mRNA in this study had to be distinguished from non-sequence-specific destruction of all viral mRNA transcripts as a result of induction of the type 1 interferon pathway (Kim et al, 2004). Interferon induction has been ruled out in previous studies in epithelial cells by interferon β detection methods (Bhuyan et al., 2004; de los Santos et al., 2005). A quantitative real-time RT-PCR assay for detection of interferon β mRNA in feline cells was designed and used to estimate copy numbers based on a standard curve produced from an RNA standard. The standard curve generated by dilutions of the interferon β standard RNA spanned six orders of magnitude, and the curve showed linearity over the entire range used for quantitation of mRNA (FIG. 19). The results were reproducible, with 7-43% intra-assay variation based on copy numbers (0.38-2.88%, based on Ct values) and 16-41% inter-assay variation based on copy numbers (0.67-2.87% based on Ct values). The theoretical limit of detection was 25 copies of interferon β mRNA. Results from this study showed that the interferon β detected in siRNA treated cells was negligible compared to the control sample (calicivirus infected cells) and similar to the background level detected in infected cells, not transfected with siRNAs (data not shown). Therefore, the suppression of viral replication was the result of the knockdown of glycoprotein D mRNA and not due to type 1 interferon production.

Discussion

We have shown that RNAi can be effectively used in CRFK cells to knockdown FHV-1 glycoprotein D mRNA when transfected prior to infection. Knockdown of FHV-1 glycoprotein D mRNA resulted in a decrease in the amount of glycoprotein D and other FHV-1 glycoproteins detected on the surface of infected cells, as well as an indirect decrease of FHV-1 DNA polymerase mRNA, independent of the production of type 1 interferon. FHV-1 glycoprotein D, like its counterpart in herpes simplex virus type 1, is essential for producing infectious virions in vitro.

Knockdown of this protein on the viral envelope appears to impair entry of the virus into cells, resulting in a reduction in the amount of infectious virus compared to control samples. However, the amount of other viral mRNAs and proteins was not necessarily affected (except when knockdown is enhanced by using a combination of two highly functional siRNAs).

Both 21-mer and 27-mer synthetic siRNAs were used in this study. The 27-mers have been shown to be more potent inducers of RNAi compared to 21-mers and are also potentially functional at sites refractive to RNAi by 21-mer siRNAs (Kim et al., 2005).

Also of interest, the 27-mer siRNA (gD1) was not functional in knockdown of glycoprotein D mRNA 24 h after infection of cells with an MOI of 1, but the 21-mer (G3) was functional. We attribute this to the fact that unlike the 21-mer, the 27-mer has to be processed by Dicer. RNA silencing is generally maximal at approximately 24 h post-transfection (Jackson et al., 2003). However, in an RNAi study in rotavirus, the highest suppression was found to occur with infection of cells with rotavirus 72 h after transfection with siRNAs, suggesting some of the elements of RNAi could be induced or activated by the presence of siRNAs, increasing their effective concentration inside the cell (Arias et al., 2004).

We also discovered the 27-mer siRNAs were toxic to cells in a concentration dependent manner, likely resulting from off-target effects with increased concentrations of siRNA leading to a stress response within the cell (Persengiev et al., 2004). Therefore, the 27-mer siRNA (gD1) was determined to be less toxic and functional at a concentration lower than what was used for the 21-mer siRNA (G3).

EXAMPLE 3

SIRNA Combination Experiments

Materials and Methods:

Combination siRNA experiments, including FHV-1 glycoprotein D and DNA polymerase targeting siRNAs, were performed in six-well plates with 6 μL siPORT Amine per well, according to manufacture's instructions. Combinations of two siRNAs per mixture were used in 100 nM total concentration per well (50 nM of each siRNA) to transfect pre-plated cells with approximately 80% confluency. Each combination was tested in duplicate and each experiment was repeated twice.

Combinations of siRNAs were tested by flow cytometry and plaque assay, as described for previous experiments.

Results:

Combinations of siRNAs reduced FHV-1 glycoproteins on the surface of infected cells. Two combinations were as effective as DNA1, including DNA1/DNA3 (72%+/−7%) and DNA1/gD1 (71%+/−6%) (FIG. 20).

Combinations of siRNAs Produce Inhibition of FHV-1 Replication In Vitro

Several combinations of siRNAs were evaluated for their ability to reduce virus replication (FIG. 21). Each combination was statistically different from the non treated control, and two combinations, DNA1/gD1 and DNA1/DNA3, were determined to produce a 96-97% reduction in virus titer compared to the control.

All patents, patent applications, provisional applications, accession numbers, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

TABLE 1 siRNA for targeting mRNA.

| siRNA | Antisense sequence (5'→3') | Location targeted |
|---|---|---|
| Feline GAPDH | Based on GenBank accession AB038241 | |
| GAP 1 (SEQ ID NO: 4) | UGCUUCACCACCUUCUUGAtg[a] | 785-767 |
| GAP 2 (SEQ ID NO: 5) | UGAGCUUCCCAUUCAGCUCtg | 679-661 |
| GAP 3 (SEQ ID NO: 6) | AGAAGCAGGGAUGAUGUUCtg | 624-606 |
| FHV DNA Polymerase | Based on GenBank accession AF079125 (Hargis et al., 1999) | |
| DNA 1 (SEQ ID NO: 7) | UGAGUAGCAUAUCUCUUCCta | 70-52 |
| DNA 2 (SEQ ID NO: 8) | GGUCAUAGCUUCUGGAAAAtc | 144-126 |
| DNA 3 (SEQ ID NO: 9) | UUUCGACUCCUUCUCUAGUtg | 121-103 |
| DNA 4 (SEQ ID NO: 10) | CUAGACUCCACGUAAUGUUta | 95-77 |
| DNA 5 (SEQ ID NO: 11) | AGACAUGGGAGAAGACCAUta | 23-5 |

[a]Upper case letters represent guide sequence; lower case letters represent 3' overhangs

TABLE 2

Primers and probes used to detect mRNA.

| Primer/Probe | Sequence (5'→3') | Location |
|---|---|---|
| FHV DNA polymerase | Based on GenBank accession AJ224971 (Willoughby, 1996) | |
| Forward (SEQ ID NO: 18) | CGGAGGGAAAATGCTTATGA | 3328-3347 |
| Reverse (SEQ ID NO: 19) | ATCCATTCTCTGGGATGCAC | 3486-3467 |
| Probe (SEQ ID NO: 20) | TCAATACATACGCTCGCCGATTAGTGGATA | 3387-3416 |
| Interferon beta | Based on GenBank accession AB021707 | |
| Forward (SEQ ID NO: 21) | ATTGCCTCAAGGACAGGATG | 237-256 |
| Reverse (SEQ ID NO: 22) | CAGGATCGTTTCCAGGTGTT | 454-435 |
| Probe (SEQ ID NO: 23) | TTTTCAGTAGAAGCACCTCTAGCACGGGAT | 354-383 |
| 28S rRNA | Based on GenBank accession AF353617 (Helps et al., 2003) | |
| Forward (Helps et al., 2003) (SEQ ID NO: 24) | CGCTAATAGGGAATGTGAGCTAGG | 663-686 |
| Reverse (Helps et al., 2003) (SEQ ID NO: 25) | TGTCTGAACCTCCAGTTTCTCTGG | 783-760 |
| Probe[a] (SEQ ID NO: 26) | AGACCGTCGTGAGACAGGTTAGTTTTACCC | 690-719 |
| GAPDH (Nguyen et al., 2007) | Based on GenBank accession AB038241 | |
| Forward (SEQ ID NO: 27) | GCTGCCCAGAACATCATCC | 598-616 |
| Reverse (SEQ ID NO: 28) | GTCAGATCCACGACGGACAC | 731-712 |
| Probe (SEQ ID NO: 29) | TCACTGGCATGGCCTTCCGT | 677-696 |

[a]Probe designed from sequence obtained from real-time RT-PCR product from CRFK cells

TABLE 3 siRNA for targeting FHV-1 glycoprotein D mRNA.

| siRNA | Antisense sequence (5'→3') | Location targeted |
|---|---|---|
| FHV glycoprotein D | Based on GenBank accession D30767 (Maeda et al., 1994) | |
| gD 1 (SEQ ID NO: 12) | UGGUUAUAACUCUUCGAUAUUGUCCuu[a] | 1397-1379 |
| gD 2 (SEQ ID NO: 13) | CAUCAUAAUCAAACCCAGUUCAUCGuc | 1351-1333 |
| gD 3 (SEQ ID NO: 14) | UUGAUGUUACAUAACGUACUUCAGCug | 1076-1058 |
| G1 (SEQ ID NO: 15) | AAUCAAACCCAGUUCAUCGtc[b] | 1351-1333 |
| G2 (SEQ ID NO: 16) | AAUAGUGGUAAUCACGAGCtc | 1556-1538 |
| G3 (SEQ ID NO: 17) | UUUAUGGUGAGGUUGUGGGtt | 1591-1573 |

[a]Bold letters represent guide sequence subsequent to processing by Dicer; lower case letters represent 3' overhangs
[b]Upper case letters represent guide sequence; lower case letters represent 3' overhangs

TABLE 4

Primers and probes used to detect mRNA.

| Primer/Probe | Sequence (5'→3') | Location |
|---|---|---|
| Glycoprotein D | Based on GenBank accession D30767 (Maeda et al., 1994) | |
| Forward (SEQ ID NO: 30) | CCTTGATGGAGCTCGTGATT | 1528-1547 |
| Reverse (SEQ ID NO: 31) | TCGAATCCTCACTCCCAGAC | 1564-1573 |
| Probe (SEQ ID NO: 32) | ACCCTATAACCCACAACCTCACCATAAAGC | 1700-1681 |

TABLE 4-continued

Primers and probes used to detect mRNA.

| Primer/Probe | Sequence (5'→3') | Location |
|---|---|---|
| Interferon β | Based on GenBank accession AB021707 | |
| Forward (SEQ ID NO: 33) | ATTGCCTCAAGGACAGGATG | 237-256 |
| Reverse (SEQ ID NO: 34) | CAGGATCGTTTCCAGGTGTT | 454-435 |
| Probe (SEQ ID NO: 35) | TTTTCAGTAGAAGCACCTCTAGCACGGGAT | 354-383 |
| 28S rRNA | Based on GenBank accession AF353617 (Helps et al., 2003) | |
| Forward (Helps et al., 2003) (SEQ ID NO: 36) | CGCTAATAGGGAATGTGAGCTAGG | 663-686 |
| Reverse (Helps et al., 2003) (SEQ ID NO: 37) | TGTCTGAACCTCCAGTTTCTCTGG | 783-760 |
| Probe[a] (SEQ ID NO: 38) | AGACCGTCGTGAGACAGGTTAGTTTTACCC | 690-719 |

[a]Probe designed from sequence obtained from real-time RT-PCR product from CRFK cells

TABLE 5

Nucleotide Sequence Combinations 1, 2
1, 3
1, 4
1, 5
1, 6
1, 7
1, 8
1, 9
1, 10
1, 11
2, 3
2, 4
2, 5
2, 6
2, 7
2, 8
2, 9
2, 10
2, 11
3, 4
3, 5
3, 6
3, 7
3, 8
3, 9
3, 10
3, 11
4, 5
4, 6
4, 7
4, 8
4, 9
4, 10
4, 11
5, 6
5, 7
5, 8
5, 9
5, 10
5, 11

TABLE 5-continued

Nucleotide Sequence Combinations 6, 7
6, 8
6, 9
6, 10
6, 11
7, 8
7, 9
7, 10
7, 11
8, 9
8, 10
8, 11
9, 10
9, 11
10, 11
1, 2, 3
1, 2, 4
1, 2, 5
1, 2, 6
1, 2, 7
1, 2, 8
1, 2, 9
1, 2, 10
1, 2, 11
1, 3, 4
1, 3, 5
1, 3, 6
1, 3, 7
1, 3, 8
1, 3, 9
1, 3, 10
1, 3, 11
1, 4, 5
1, 4, 6
1, 4, 7
1, 4, 8
1, 4, 9
1, 4, 10
1, 4, 11
1, 5, 6
1, 5, 7
1, 5, 8
1, 5, 9
1, 5, 10
1, 5, 11
1, 6, 7
1, 6, 8
1, 6, 9
1, 6, 10
1, 6, 11
1, 7, 8
1, 7, 9
1, 7, 10
1, 7, 11
1, 8, 9
1, 8, 10
1, 8, 11
1, 9, 10
1, 9, 11
1, 10, 11
2, 3, 4
2, 3, 5
2, 3, 6
2, 3, 7
2, 3, 8
2, 3, 9
2, 3, 10
2, 3, 11
2, 4, 5
2, 4, 6
2, 4, 7
2, 4, 8
2, 4, 9
2, 4, 10
2, 4, 11
2, 5, 6
2, 5, 7
2, 5, 8

TABLE 5-continued

| Nucleotide Sequence Combinations |
|---|
| 2, 5, 9 |
| 2, 5, 10 |
| 2, 5, 11 |
| 2, 6, 7 |
| 2, 6, 8 |
| 2, 6, 9 |
| 2, 6, 10 |
| 2, 6, 11 |
| 2, 7, 8 |
| 2, 7, 9 |
| 2, 7, 10 |
| 2, 7, 11 |
| 2, 8, 9 |
| 2, 8, 10 |
| 2, 8, 11 |
| 2, 9, 10 |
| 2, 9, 11 |
| 2, 10, 11 |
| 3, 4, 5 |
| 3, 4, 6 |
| 3, 4, 7 |
| 3, 4, 8 |
| 3, 4, 9 |
| 3, 4, 10 |
| 3, 4, 11 |
| 3, 5, 6 |
| 3, 5, 7 |
| 3, 5, 8 |
| 3, 5, 9 |
| 3, 5, 10 |
| 3, 5, 11 |
| 3, 6, 7 |
| 3, 6, 8 |
| 3, 6, 9 |
| 3, 6, 10 |
| 3, 6, 11 |
| 3, 7, 8 |
| 3, 7, 9 |
| 3, 7, 10 |
| 3, 7, 11 |
| 3, 8, 9 |
| 3, 8, 10 |
| 3, 8, 11 |
| 3, 9, 10 |
| 3, 9, 11 |
| 3, 10, 11 |
| 4, 5, 6 |
| 4, 5, 7 |
| 4, 5, 8 |
| 4, 5, 9 |
| 4, 5, 10 |
| 4, 5, 11 |
| 4, 6, 7 |
| 4, 6, 8 |
| 4, 6, 9 |
| 4, 6, 10 |
| 4, 6, 11 |
| 4, 7, 8 |
| 4, 7, 9 |
| 4, 7, 10 |
| 4, 7, 11 |
| 4, 8, 9 |
| 4, 8, 10 |
| 4, 8, 11 |
| 4, 9, 10 |
| 4, 9, 11 |
| 4, 10, 11 |
| 5, 6, 7 |
| 5, 6, 8 |
| 5, 6, 9 |
| 5, 6, 10 |
| 5, 6, 11 |
| 5, 7, 8 |
| 5, 7, 9 |
| 5, 7, 10 |
| 5, 7, 11 |
| 5, 8, 9 |
| 5, 8, 10 |
| 5, 8, 11 |
| 5, 9, 10 |
| 5, 9, 11 |
| 5, 10, 11 |
| 6, 7, 8 |
| 6, 7, 9 |
| 6, 7, 10 |
| 6, 7, 11 |
| 6, 8, 9 |
| 6, 8, 10 |
| 6, 8, 11 |
| 6, 9, 10 |
| 6, 9, 11 |
| 6, 10, 11 |
| 7, 8, 9 |
| 7, 8, 10 |
| 7, 8, 11 |
| 7, 9, 10 |
| 7, 9, 11 |
| 7, 10, 11 |
| 8, 9, 10 |
| 8, 9, 11 |
| 8, 10, 11 |
| 9, 10, 11 |
| 1, 2, 3, 4 |
| 1, 2, 3, 5 |
| 1, 2, 3, 6 |
| 1, 2, 3, 7 |
| 1, 2, 3, 8 |
| 1, 2, 3, 9 |
| 1, 2, 3, 10 |
| 1, 2, 3, 11 |
| 1, 2, 4, 5 |
| 1, 2, 4, 6 |
| 1, 2, 4, 7 |
| 1, 2, 4, 8 |
| 1, 2, 4, 9 |
| 1, 2, 4, 10 |
| 1, 2, 4, 11 |
| 1, 2, 5, 6 |
| 1, 2, 5, 7 |
| 1, 2, 5, 8 |
| 1, 2, 5, 9 |
| 1, 2, 5, 10 |
| 1, 2, 5, 11 |
| 1, 2, 6, 7 |
| 1, 2, 6, 8 |
| 1, 2, 6, 9 |
| 1, 2, 6, 10 |
| 1, 2, 6, 11 |
| 1, 2, 7, 8 |
| 1, 2, 7, 9 |
| 1, 2, 7, 10 |
| 1, 2, 7, 11 |
| 1, 2, 8, 9 |
| 1, 2, 8, 10 |
| 1, 2, 8, 11 |
| 1, 2, 9, 10 |
| 1, 2, 9, 11 |
| 1, 2, 10, 11 |
| 1, 3, 4, 5 |
| 1, 3, 4, 6 |
| 1, 3, 4, 7 |
| 1, 3, 4, 8 |
| 1, 3, 4, 9 |
| 1, 3, 4, 10 |
| 1, 3, 4, 11 |
| 1, 3, 5, 6 |
| 1, 3, 5, 7 |
| 1, 3, 5, 8 |
| 1, 3, 5, 9 |
| 1, 3, 5, 10 |
| 1, 3, 5, 11 |
| 1, 3, 6, 7 |
| 1, 3, 6, 8 |
| 1, 3, 6, 9 |
| 1, 3, 6, 10 |
| 1, 3, 6, 11 |

TABLE 5-continued

| Nucleotide Sequence Combinations |
|---|
| 1, 3, 7, 8 |
| 1, 3, 7, 9 |
| 1, 3, 7, 10 |
| 1, 3, 7, 11 |
| 1, 3, 8, 9 |
| 1, 3, 8, 10 |
| 1, 3, 8, 11 |
| 1, 3, 9, 10 |
| 1, 3, 9, 11 |
| 1, 3, 10, 11 |
| 1, 4, 5, 6 |
| 1, 4, 5, 7 |
| 1, 4, 5, 8 |
| 1, 4, 5, 9 |
| 1, 4, 5, 10 |
| 1, 4, 5, 11 |
| 1, 4, 6, 7 |
| 1, 4, 6, 8 |
| 1, 4, 6, 9 |
| 1, 4, 6, 10 |
| 1, 4, 6, 11 |
| 1, 4, 7, 8 |
| 1, 4, 7, 9 |
| 1, 4, 7, 10 |
| 1, 4, 7, 11 |
| 1, 4, 8, 9 |
| 1, 4, 8, 10 |
| 1, 4, 8, 11 |
| 1, 4, 9, 10 |
| 1, 4, 9, 11 |
| 1, 4, 10, 11 |
| 1, 5, 6, 7 |
| 1, 5, 6, 8 |
| 1, 5, 6, 9 |
| 1, 5, 6, 10 |
| 1, 5, 6, 11 |
| 1, 5, 7, 8 |
| 1, 5, 7, 9 |
| 1, 5, 7, 10 |
| 1, 5, 7, 11 |
| 1, 5, 8, 9 |
| 1, 5, 8, 10 |
| 1, 5, 8, 11 |
| 1, 5, 9, 10 |
| 1, 5, 9, 11 |
| 1, 5, 10, 11 |
| 1, 6, 7, 8 |
| 1, 6, 7, 9 |
| 1, 6, 7, 10 |
| 1, 6, 7, 11 |
| 1, 6, 8, 9 |
| 1, 6, 8, 10 |
| 1, 6, 8, 11 |
| 1, 6, 9, 10 |
| 1, 6, 9, 11 |
| 1, 6, 10, 11 |
| 1, 7, 8, 9 |
| 1, 7, 8, 10 |
| 1, 7, 8, 11 |
| 1, 7, 9, 10 |
| 1, 7, 9, 11 |
| 1, 7, 10, 11 |
| 1, 8, 9, 10 |
| 1, 8, 9, 11 |
| 1, 8, 10, 11 |
| 1, 9, 10, 11 |
| 2, 3, 4, 5 |
| 2, 3, 4, 6 |
| 2, 3, 4, 7 |
| 2, 3, 4, 8 |
| 2, 3, 4, 9 |
| 2, 3, 4, 10 |
| 2, 3, 4, 11 |
| 2, 3, 5, 6 |
| 2, 3, 5, 7 |
| 2, 3, 5, 8 |
| 2, 3, 5, 9 |
| 2, 3, 5, 10 |
| 2, 3, 5, 11 |
| 2, 3, 6, 7 |
| 2, 3, 6, 8 |
| 2, 3, 6, 9 |
| 2, 3, 6, 10 |
| 2, 3, 6, 11 |
| 2, 3, 7, 8 |
| 2, 3, 7, 9 |
| 2, 3, 7, 10 |
| 2, 3, 7, 11 |
| 2, 3, 8, 9 |
| 2, 3, 8, 10 |
| 2, 3, 8, 11 |
| 2, 3, 9, 10 |
| 2, 3, 9, 11 |
| 2, 3, 10, 11 |
| 2, 4, 5, 6 |
| 2, 4, 5, 7 |
| 2, 4, 5, 8 |
| 2, 4, 5, 9 |
| 2, 4, 5, 10 |
| 2, 4, 5, 11 |
| 2, 4, 6, 7 |
| 2, 4, 6, 8 |
| 2, 4, 6, 9 |
| 2, 4, 6, 10 |
| 2, 4, 6, 11 |
| 2, 4, 7, 8 |
| 2, 4, 7, 9 |
| 2, 4, 7, 10 |
| 2, 4, 7, 11 |
| 2, 4, 8, 9 |
| 2, 4, 8, 10 |
| 2, 4, 8, 11 |
| 2, 4, 9, 10 |
| 2, 4, 9, 11 |
| 2, 4, 10, 11 |
| 2, 5, 6, 7 |
| 2, 5, 6, 8 |
| 2, 5, 6, 9 |
| 2, 5, 6, 10 |
| 2, 5, 6, 11 |
| 2, 5, 7, 8 |
| 2, 5, 7, 9 |
| 2, 5, 7, 10 |
| 2, 5, 7, 11 |
| 2, 5, 8, 9 |
| 2, 5, 8, 10 |
| 2, 5, 8, 11 |
| 2, 5, 9, 10 |
| 2, 5, 9, 11 |
| 2, 5, 10, 11 |
| 2, 6, 7, 8 |
| 2, 6, 7, 9 |
| 2, 6, 7, 10 |
| 2, 6, 7, 11 |
| 2, 6, 8, 9 |
| 2, 6, 8, 10 |
| 2, 6, 8, 11 |
| 2, 6, 9, 10 |
| 2, 6, 9, 11 |
| 2, 6, 10, 11 |
| 2, 7, 8, 9 |
| 2, 7, 8, 10 |
| 2, 7, 8, 11 |
| 2, 7, 9, 10 |
| 2, 7, 9, 11 |
| 2, 7, 10, 11 |
| 2, 8, 9, 10 |
| 2, 8, 9, 11 |
| 2, 8, 10, 11 |
| 2, 9, 10, 11 |
| 3, 4, 5, 6 |
| 3, 4, 5, 7 |
| 3, 4, 5, 8 |
| 3, 4, 5, 9 |
| 3, 4, 5, 10 |
| 3, 4, 5, 11 |

TABLE 5-continued

| Nucleotide Sequence Combinations |
|---|
| 3, 4, 6, 7 |
| 3, 4, 6, 8 |
| 3, 4, 6, 9 |
| 3, 4, 6, 10 |
| 3, 4, 6, 11 |
| 3, 4, 7, 8 |
| 3, 4, 7, 9 |
| 3, 4, 7, 10 |
| 3, 4, 7, 11 |
| 3, 4, 8, 9 |
| 3, 4, 8, 10 |
| 3, 4, 8, 11 |
| 3, 4, 9, 10 |
| 3, 4, 9, 11 |
| 3, 4, 10, 11 |
| 3, 5, 6, 7 |
| 3, 5, 6, 8 |
| 3, 5, 6, 9 |
| 3, 5, 6, 10 |
| 3, 5, 6, 11 |
| 3, 5, 7, 8 |
| 3, 5, 7, 9 |
| 3, 5, 7, 10 |
| 3, 5, 7, 11 |
| 3, 5, 8, 9 |
| 3, 5, 8, 10 |
| 3, 5, 8, 11 |
| 3, 5, 9, 10 |
| 3, 5, 9, 11 |
| 3, 5, 10, 11 |
| 3, 6, 7, 8 |
| 3, 6, 7, 9 |
| 3, 6, 7, 10 |
| 3, 6, 7, 11 |
| 3, 6, 8, 9 |
| 3, 6, 8, 10 |
| 3, 6, 8, 11 |
| 3, 6, 9, 10 |
| 3, 6, 9, 11 |
| 3, 6, 10, 11 |
| 3, 7, 8, 9 |
| 3, 7, 8, 10 |
| 3, 7, 8, 11 |
| 3, 7, 9, 10 |
| 3, 7, 9, 11 |
| 3, 7, 10, 11 |
| 3, 8, 9, 10 |
| 3, 8, 9, 11 |
| 3, 8, 10, 11 |
| 3, 9, 10, 11 |
| 4, 5, 6, 7 |
| 4, 5, 6, 8 |
| 4, 5, 6, 9 |
| 4, 5, 6, 10 |
| 4, 5, 6, 11 |
| 4, 5, 7, 8 |
| 4, 5, 7, 9 |
| 4, 5, 7, 10 |
| 4, 5, 7, 11 |
| 4, 5, 8, 9 |
| 4, 5, 8, 10 |
| 4, 5, 8, 11 |
| 4, 5, 9, 10 |
| 4, 5, 9, 11 |
| 4, 5, 10, 11 |
| 4, 6, 7, 8 |
| 4, 6, 7, 9 |
| 4, 6, 7, 10 |
| 4, 6, 7, 11 |
| 4, 6, 8, 9 |
| 4, 6, 8, 10 |
| 4, 6, 8, 11 |
| 4, 6, 9, 10 |
| 4, 6, 9, 11 |
| 4, 6, 10, 11 |
| 4, 7, 8, 9 |
| 4, 7, 8, 10 |
| 4, 7, 8, 11 |
| 4, 7, 9, 10 |
| 4, 7, 9, 11 |
| 4, 7, 10, 11 |
| 4, 8, 9, 10 |
| 4, 8, 9, 11 |
| 4, 8, 10, 11 |
| 4, 9, 10, 11 |
| 5, 6, 7, 8 |
| 5, 6, 7, 9 |
| 5, 6, 7, 10 |
| 5, 6, 7, 11 |
| 5, 6, 8, 9 |
| 5, 6, 8, 10 |
| 5, 6, 8, 11 |
| 5, 6, 9, 10 |
| 5, 6, 9, 11 |
| 5, 6, 10, 11 |
| 5, 7, 8, 9 |
| 5, 7, 8, 10 |
| 5, 7, 8, 11 |
| 5, 7, 9, 10 |
| 5, 7, 9, 11 |
| 5, 7, 10, 11 |
| 5, 8, 9, 10 |
| 5, 8, 9, 11 |
| 5, 8, 10, 11 |
| 5, 9, 10, 11 |
| 6, 7, 8, 9 |
| 6, 7, 8, 10 |
| 6, 7, 8, 11 |
| 6, 7, 9, 10 |
| 6, 7, 9, 11 |
| 6, 7, 10, 11 |
| 6, 8, 9, 10 |
| 6, 8, 9, 11 |
| 6, 8, 10, 11 |
| 6, 9, 10, 11 |
| 7, 8, 9, 10 |
| 7, 8, 9, 11 |
| 7, 8, 10, 11 |
| 7, 9, 10, 11 |
| 8, 9, 10, 11 |
| 1, 2, 3, 4, 5 |
| 1, 2, 3, 4, 6 |
| 1, 2, 3, 4, 7 |
| 1, 2, 3, 4, 8 |
| 1, 2, 3, 4, 9 |
| 1, 2, 3, 4, 10 |
| 1, 2, 3, 4, 11 |
| 1, 2, 3, 5, 6 |
| 1, 2, 3, 5, 7 |
| 1, 2, 3, 5, 8 |
| 1, 2, 3, 5, 9 |
| 1, 2, 3, 5, 10 |
| 1, 2, 3, 5, 11 |
| 1, 2, 3, 6, 7 |
| 1, 2, 3, 6, 8 |
| 1, 2, 3, 6, 9 |
| 1, 2, 3, 6, 10 |
| 1, 2, 3, 6, 11 |
| 1, 2, 3, 7, 8 |
| 1, 2, 3, 7, 9 |
| 1, 2, 3, 7, 10 |
| 1, 2, 3, 7, 11 |
| 1, 2, 3, 8, 9 |
| 1, 2, 3, 8, 10 |
| 1, 2, 3, 8, 11 |
| 1, 2, 3, 9, 10 |
| 1, 2, 3, 9, 11 |
| 1, 2, 3, 10, 11 |
| 1, 2, 4, 5, 6 |
| 1, 2, 4, 5, 7 |
| 1, 2, 4, 5, 8 |
| 1, 2, 4, 5, 9 |
| 1, 2, 4, 5, 10 |
| 1, 2, 4, 5, 11 |
| 1, 2, 4, 6, 7 |
| 1, 2, 4, 6, 8 |

TABLE 5-continued

Nucleotide Sequence Combinations 1, 2, 4, 6, 9
1, 2, 4, 6, 10
1, 2, 4, 6, 11
1, 2, 4, 7, 8
1, 2, 4, 7, 9
1, 2, 4, 7, 10
1, 2, 4, 7, 11
1, 2, 4, 8, 9
1, 2, 4, 8, 10
1, 2, 4, 8, 11
1, 2, 4, 9, 10
1, 2, 4, 9, 11
1, 2, 4, 10, 11
1, 2, 5, 6, 7
1, 2, 5, 6, 8
1, 2, 5, 6, 9
1, 2, 5, 6, 10
1, 2, 5, 6, 11
1, 2, 5, 7, 8
1, 2, 5, 7, 9
1, 2, 5, 7, 10
1, 2, 5, 7, 11
1, 2, 5, 8, 9
1, 2, 5, 8, 10
1, 2, 5, 8, 11
1, 2, 5, 9, 10
1, 2, 5, 9, 11
1, 2, 5, 10, 11
1, 2, 6, 7, 8
1, 2, 6, 7, 9
1, 2, 6, 7, 10
1, 2, 6, 7, 11
1, 2, 6, 8, 9
1, 2, 6, 8, 10
1, 2, 6, 8, 11
1, 2, 6, 9, 10
1, 2, 6, 9, 11
1, 2, 6, 10, 11
1, 2, 7, 8, 9
1, 2, 7, 8, 10
1, 2, 7, 8, 11
1, 2, 7, 9, 10
1, 2, 7, 9, 11
1, 2, 7, 10, 11
1, 2, 8, 9, 10
1, 2, 8, 9, 11
1, 2, 8, 10, 11
1, 2, 9, 10, 11
1, 3, 4, 5, 6
1, 3, 4, 5, 7
1, 3, 4, 5, 8
1, 3, 4, 5, 9
1, 3, 4, 5, 10
1, 3, 4, 5, 11
1, 3, 4, 6, 7
1, 3, 4, 6, 8
1, 3, 4, 6, 9
1, 3, 4, 6, 10
1, 3, 4, 6, 11
1, 3, 4, 7, 8
1, 3, 4, 7, 9
1, 3, 4, 7, 10
1, 3, 4, 7, 11
1, 3, 4, 8, 9
1, 3, 4, 8, 10
1, 3, 4, 8, 11
1, 3, 4, 9, 10
1, 3, 4, 9, 11
1, 3, 4, 10, 11
1, 3, 5, 6, 7
1, 3, 5, 6, 8
1, 3, 5, 6, 9
1, 3, 5, 6, 10
1, 3, 5, 6, 11
1, 3, 5, 7, 8
1, 3, 5, 7, 9
1, 3, 5, 7, 10
1, 3, 5, 7, 11
1, 3, 5, 8, 9
1, 3, 5, 8, 10
1, 3, 5, 8, 11
1, 3, 5, 9, 10
1, 3, 5, 9, 11
1, 3, 5, 10, 11
1, 3, 6, 7, 8
1, 3, 6, 7, 9
1, 3, 6, 7, 10
1, 3, 6, 7, 11
1, 3, 6, 8, 9
1, 3, 6, 8, 10
1, 3, 6, 8, 11
1, 3, 6, 9, 10
1, 3, 6, 9, 11
1, 3, 6, 10, 11
1, 3, 7, 8, 9
1, 3, 7, 8, 10
1, 3, 7, 8, 11
1, 3, 7, 9, 10
1, 3, 7, 9, 11
1, 3, 7, 10, 11
1, 3, 8, 9, 10
1, 3, 8, 9, 11
1, 3, 8, 10, 11
1, 3, 9, 10, 11
1, 4, 5, 6, 7
1, 4, 5, 6, 8
1, 4, 5, 6, 9
1, 4, 5, 6, 10
1, 4, 5, 6, 11
1, 4, 5, 7, 8
1, 4, 5, 7, 9
1, 4, 5, 7, 10
1, 4, 5, 7, 11
1, 4, 5, 8, 9
1, 4, 5, 8, 10
1, 4, 5, 8, 11
1, 4, 5, 9, 10
1, 4, 5, 9, 11
1, 4, 5, 10, 11
1, 4, 6, 7, 8
1, 4, 6, 7, 9
1, 4, 6, 7, 10
1, 4, 6, 7, 11
1, 4, 6, 8, 9
1, 4, 6, 8, 10
1, 4, 6, 8, 11
1, 4, 6, 9, 10
1, 4, 6, 9, 11
1, 4, 6, 10, 11
1, 4, 7, 8, 9
1, 4, 7, 8, 10
1, 4, 7, 8, 11
1, 4, 7, 9, 10
1, 4, 7, 9, 11
1, 4, 7, 10, 11
1, 4, 8, 9, 10
1, 4, 8, 9, 11
1, 4, 8, 10, 11
1, 4, 9, 10, 11
1, 5, 6, 7, 8
1, 5, 6, 7, 9
1, 5, 6, 7, 10
1, 5, 6, 7, 11
1, 5, 6, 8, 9
1, 5, 6, 8, 10
1, 5, 6, 8, 11
1, 5, 6, 9, 10
1, 5, 6, 9, 11
1, 5, 6, 10, 11
1, 5, 7, 8, 9
1, 5, 7, 8, 10
1, 5, 7, 8, 11
1, 5, 7, 9, 10
1, 5, 7, 9, 11
1, 5, 7, 10, 11
1, 5, 8, 9, 10

TABLE 5-continued

Nucleotide Sequence Combinations 1, 5, 8, 9, 11
1, 5, 8, 10, 11
1, 5, 9, 10, 11
1, 6, 7, 8, 9
1, 6, 7, 8, 10
1, 6, 7, 8, 11
1, 6, 7, 9, 10
1, 6, 7, 9, 11
1, 6, 7, 10, 11
1, 6, 8, 9, 10
1, 6, 8, 9, 11
1, 6, 8, 10, 11
1, 6, 9, 10, 11
1, 7, 8, 9, 10
1, 7, 8, 9, 11
1, 7, 8, 10, 11
1, 7, 9, 10, 11
1, 8, 9, 10, 11
2, 3, 4, 5, 6
2, 3, 4, 5, 7
2, 3, 4, 5, 8
2, 3, 4, 5, 9
2, 3, 4, 5, 10
2, 3, 4, 5, 11
2, 3, 4, 6, 7
2, 3, 4, 6, 8
2, 3, 4, 6, 9
2, 3, 4, 6, 10
2, 3, 4, 6, 11
2, 3, 4, 7, 8
2, 3, 4, 7, 9
2, 3, 4, 7, 10
2, 3, 4, 7, 11
2, 3, 4, 8, 9
2, 3, 4, 8, 10
2, 3, 4, 8, 11
2, 3, 4, 9, 10
2, 3, 4, 9, 11
2, 3, 4, 10, 11
2, 3, 5, 6, 7
2, 3, 5, 6, 8
2, 3, 5, 6, 9
2, 3, 5, 6, 10
2, 3, 5, 6, 11
2, 3, 5, 7, 8
2, 3, 5, 7, 9
2, 3, 5, 7, 10
2, 3, 5, 7, 11
2, 3, 5, 8, 9
2, 3, 5, 8, 10
2, 3, 5, 8, 11
2, 3, 5, 9, 10
2, 3, 5, 9, 11
2, 3, 5, 10, 11
2, 3, 6, 7, 8
2, 3, 6, 7, 9
2, 3, 6, 7, 10
2, 3, 6, 7, 11
2, 3, 6, 8, 9
2, 3, 6, 8, 10
2, 3, 6, 8, 11
2, 3, 6, 9, 10
2, 3, 6, 9, 11
2, 3, 6, 10, 11
2, 3, 7, 8, 9
2, 3, 7, 8, 10
2, 3, 7, 8, 11
2, 3, 7, 9, 10
2, 3, 7, 9, 11
2, 3, 7, 10, 11
2, 3, 8, 9, 10
2, 3, 8, 9, 11
2, 3, 8, 10, 11
2, 3, 9, 10, 11
2, 4, 5, 6, 7
2, 4, 5, 6, 8
2, 4, 5, 6, 9
2, 4, 5, 6, 10

TABLE 5-continued

Nucleotide Sequence Combinations 2, 4, 5, 6, 11
2, 4, 5, 7, 8
2, 4, 5, 7, 9
2, 4, 5, 7, 10
2, 4, 5, 7, 11
2, 4, 5, 8, 9
2, 4, 5, 8, 10
2, 4, 5, 8, 11
2, 4, 5, 9, 10
2, 4, 5, 9, 11
2, 4, 5, 10, 11
2, 4, 6, 7, 8
2, 4, 6, 7, 9
2, 4, 6, 7, 10
2, 4, 6, 7, 11
2, 4, 6, 8, 9
2, 4, 6, 8, 10
2, 4, 6, 8, 11
2, 4, 6, 9, 10
2, 4, 6, 9, 11
2, 4, 6, 10, 11
2, 4, 7, 8, 9
2, 4, 7, 8, 10
2, 4, 7, 8, 11
2, 4, 7, 9, 10
2, 4, 7, 9, 11
2, 4, 7, 10, 11
2, 4, 8, 9, 10
2, 4, 8, 9, 11
2, 4, 8, 10, 11
2, 4, 9, 10, 11
2, 5, 6, 7, 8
2, 5, 6, 7, 9
2, 5, 6, 7, 10
2, 5, 6, 7, 11
2, 5, 6, 8, 9
2, 5, 6, 8, 10
2, 5, 6, 8, 11
2, 5, 6, 9, 10
2, 5, 6, 9, 11
2, 5, 6, 10, 11
2, 5, 7, 8, 9
2, 5, 7, 8, 10
2, 5, 7, 8, 11
2, 5, 7, 9, 10
2, 5, 7, 9, 11
2, 5, 7, 10, 11
2, 5, 8, 9, 10
2, 5, 8, 9, 11
2, 5, 8, 10, 11
2, 5, 9, 10, 11
2, 6, 7, 8, 9
2, 6, 7, 8, 10
2, 6, 7, 8, 11
2, 6, 7, 9, 10
2, 6, 7, 9, 11
2, 6, 7, 10, 11
2, 6, 8, 9, 10
2, 6, 8, 9, 11
2, 6, 8, 10, 11
2, 6, 9, 10, 11
2, 7, 8, 9, 10
2, 7, 8, 9, 11
2, 7, 8, 10, 11
2, 7, 9, 10, 11
2, 8, 9, 10, 11
3, 4, 5, 6, 7
3, 4, 5, 6, 8
3, 4, 5, 6, 9
3, 4, 5, 6, 10
3, 4, 5, 6, 11
3, 4, 5, 7, 8
3, 4, 5, 7, 9
3, 4, 5, 7, 10
3, 4, 5, 7, 11
3, 4, 5, 8, 9
3, 4, 5, 8, 10
3, 4, 5, 8, 11

TABLE 5-continued

Nucleotide Sequence Combinations 3, 4, 5, 9, 10
3, 4, 5, 9, 11
3, 4, 5, 10, 11
3, 4, 6, 7, 8
3, 4, 6, 7, 9
3, 4, 6, 7, 10
3, 4, 6, 7, 11
3, 4, 6, 8, 9
3, 4, 6, 8, 10
3, 4, 6, 8, 11
3, 4, 6, 9, 10
3, 4, 6, 9, 11
3, 4, 6, 10, 11
3, 4, 7, 8, 9
3, 4, 7, 8, 10
3, 4, 7, 8, 11
3, 4, 7, 9, 10
3, 4, 7, 9, 11
3, 4, 7, 10, 11
3, 4, 8, 9, 10
3, 4, 8, 9, 11
3, 4, 8, 10, 11
3, 4, 9, 10, 11
3, 5, 6, 7, 8
3, 5, 6, 7, 9
3, 5, 6, 7, 10
3, 5, 6, 7, 11
3, 5, 6, 8, 9
3, 5, 6, 8, 10
3, 5, 6, 8, 11
3, 5, 6, 9, 10
3, 5, 6, 9, 11
3, 5, 6, 10, 11
3, 5, 7, 8, 9
3, 5, 7, 8, 10
3, 5, 7, 8, 11
3, 5, 7, 9, 10
3, 5, 7, 9, 11
3, 5, 7, 10, 11
3, 5, 8, 9, 10
3, 5, 8, 9, 11
3, 5, 8, 10, 11
3, 5, 9, 10, 11
3, 6, 7, 8, 9
3, 6, 7, 8, 10
3, 6, 7, 8, 11
3, 6, 7, 9, 10
3, 6, 7, 9, 11
3, 6, 7, 10, 11
3, 6, 8, 9, 10
3, 6, 8, 9, 11
3, 6, 8, 10, 11
3, 6, 9, 10, 11
3, 7, 8, 9, 10
3, 7, 8, 9, 11
3, 7, 8, 10, 11
3, 7, 9, 10, 11
3, 8, 9, 10, 11
4, 5, 6, 7, 8
4, 5, 6, 7, 9
4, 5, 6, 7, 10
4, 5, 6, 7, 11
4, 5, 6, 8, 9
4, 5, 6, 8, 10
4, 5, 6, 8, 11
4, 5, 6, 9, 10
4, 5, 6, 9, 11
4, 5, 6, 10, 11
4, 5, 7, 8, 9
4, 5, 7, 8, 10
4, 5, 7, 8, 11
4, 5, 7, 9, 10
4, 5, 7, 9, 11
4, 5, 7, 10, 11
4, 5, 8, 9, 10
4, 5, 8, 9, 11
4, 5, 8, 10, 11
4, 5, 9, 10, 11
4, 6, 7, 8, 9
4, 6, 7, 8, 10
4, 6, 7, 8, 11
4, 6, 7, 9, 10
4, 6, 7, 9, 11
4, 6, 7, 10, 11
4, 6, 8, 9, 10
4, 6, 8, 9, 11
4, 6, 8, 10, 11
4, 6, 9, 10, 11
4, 7, 8, 9, 10
4, 7, 8, 9, 11
4, 7, 8, 10, 11
4, 7, 9, 10, 11
4, 8, 9, 10, 11
5, 6, 7, 8, 9
5, 6, 7, 8, 10
5, 6, 7, 8, 11
5, 6, 7, 9, 10
5, 6, 7, 9, 11
5, 6, 7, 10, 11
5, 6, 8, 9, 10
5, 6, 8, 9, 11
5, 6, 8, 10, 11
5, 6, 9, 10, 11
5, 7, 8, 9, 10
5, 7, 8, 9, 11
5, 7, 8, 10, 11
5, 7, 9, 10, 11
5, 8, 9, 10, 11
6, 7, 8, 9, 10
6, 7, 8, 9, 11
6, 7, 8, 10, 11
6, 7, 9, 10, 11
6, 8, 9, 10, 11
7, 8, 9, 10, 11
1, 2, 3, 4, 5, 6
1, 2, 3, 4, 5, 7
1, 2, 3, 4, 5, 8
1, 2, 3, 4, 5, 9
1, 2, 3, 4, 5, 10
1, 2, 3, 4, 5, 11
1, 2, 3, 4, 6, 7
1, 2, 3, 4, 6, 8
1, 2, 3, 4, 6, 9
1, 2, 3, 4, 6, 10
1, 2, 3, 4, 6, 11
1, 2, 3, 4, 7, 8
1, 2, 3, 4, 7, 9
1, 2, 3, 4, 7, 10
1, 2, 3, 4, 7, 11
1, 2, 3, 4, 8, 9
1, 2, 3, 4, 8, 10
1, 2, 3, 4, 8, 11
1, 2, 3, 4, 9, 10
1, 2, 3, 4, 9, 11
1, 2, 3, 4, 10, 11
1, 2, 3, 5, 6, 7
1, 2, 3, 5, 6, 8
1, 2, 3, 5, 6, 9
1, 2, 3, 5, 6, 10
1, 2, 3, 5, 6, 11
1, 2, 3, 5, 7, 8
1, 2, 3, 5, 7, 9
1, 2, 3, 5, 7, 10
1, 2, 3, 5, 7, 11
1, 2, 3, 5, 8, 9
1, 2, 3, 5, 8, 10
1, 2, 3, 5, 8, 11
1, 2, 3, 5, 9, 10
1, 2, 3, 5, 9, 11
1, 2, 3, 5, 10, 11
1, 2, 3, 6, 7, 8
1, 2, 3, 6, 7, 9
1, 2, 3, 6, 7, 10
1, 2, 3, 6, 7, 11
1, 2, 3, 6, 8, 9
1, 2, 3, 6, 8, 10

TABLE 5-continued

Nucleotide Sequence Combinations 1, 2, 3, 6, 8, 11
1, 2, 3, 6, 9, 10
1, 2, 3, 6, 9, 11
1, 2, 3, 6, 10, 11
1, 2, 3, 7, 8, 9
1, 2, 3, 7, 8, 10
1, 2, 3, 7, 8, 11
1, 2, 3, 7, 9, 10
1, 2, 3, 7, 9, 11
1, 2, 3, 7, 10, 11
1, 2, 3, 8, 9, 10
1, 2, 3, 8, 9, 11
1, 2, 3, 8, 10, 11
1, 2, 3, 9, 10, 11
1, 2, 4, 5, 6, 7
1, 2, 4, 5, 6, 8
1, 2, 4, 5, 6, 9
1, 2, 4, 5, 6, 10
1, 2, 4, 5, 6, 11
1, 2, 4, 5, 7, 8
1, 2, 4, 5, 7, 9
1, 2, 4, 5, 7, 10
1, 2, 4, 5, 7, 11
1, 2, 4, 5, 8, 9
1, 2, 4, 5, 8, 10
1, 2, 4, 5, 8, 11
1, 2, 4, 5, 9, 10
1, 2, 4, 5, 9, 11
1, 2, 4, 5, 10, 11
1, 2, 4, 6, 7, 8
1, 2, 4, 6, 7, 9
1, 2, 4, 6, 7, 10
1, 2, 4, 6, 7, 11
1, 2, 4, 6, 8, 9
1, 2, 4, 6, 8, 10
1, 2, 4, 6, 8, 11
1, 2, 4, 6, 9, 10
1, 2, 4, 6, 9, 11
1, 2, 4, 6, 10, 11
1, 2, 4, 7, 8, 9
1, 2, 4, 7, 8, 10
1, 2, 4, 7, 8, 11
1, 2, 4, 7, 9, 10
1, 2, 4, 7, 9, 11
1, 2, 4, 7, 10, 11
1, 2, 4, 8, 9, 10
1, 2, 4, 8, 9, 11
1, 2, 4, 8, 10, 11
1, 2, 4, 9, 10, 11
1, 2, 5, 6, 7, 8
1, 2, 5, 6, 7, 9
1, 2, 5, 6, 7, 10
1, 2, 5, 6, 7, 11
1, 2, 5, 6, 8, 9
1, 2, 5, 6, 8, 10
1, 2, 5, 6, 8, 11
1, 2, 5, 6, 9, 10
1, 2, 5, 6, 9, 11
1, 2, 5, 6, 10, 11
1, 2, 5, 7, 8, 9
1, 2, 5, 7, 8, 10
1, 2, 5, 7, 8, 11
1, 2, 5, 7, 9, 10
1, 2, 5, 7, 9, 11
1, 2, 5, 7, 10, 11
1, 2, 5, 8, 9, 10
1, 2, 5, 8, 9, 11
1, 2, 5, 8, 10, 11
1, 2, 5, 9, 10, 11
1, 2, 6, 7, 8, 9
1, 2, 6, 7, 8, 10
1, 2, 6, 7, 8, 11
1, 2, 6, 7, 9, 10
1, 2, 6, 7, 9, 11
1, 2, 6, 7, 10, 11
1, 2, 6, 8, 9, 10
1, 2, 6, 8, 9, 11
1, 2, 6, 8, 10, 11
1, 2, 6, 9, 10, 11
1, 2, 7, 8, 9, 10
1, 2, 7, 8, 9, 11
1, 2, 7, 8, 10, 11
1, 2, 7, 9, 10, 11
1, 2, 8, 9, 10, 11
1, 3, 4, 5, 6, 7
1, 3, 4, 5, 6, 8
1, 3, 4, 5, 6, 9
1, 3, 4, 5, 6, 10
1, 3, 4, 5, 6, 11
1, 3, 4, 5, 7, 8
1, 3, 4, 5, 7, 9
1, 3, 4, 5, 7, 10
1, 3, 4, 5, 7, 11
1, 3, 4, 5, 8, 9
1, 3, 4, 5, 8, 10
1, 3, 4, 5, 8, 11
1, 3, 4, 5, 9, 10
1, 3, 4, 5, 9, 11
1, 3, 4, 5, 10, 11
1, 3, 4, 6, 7, 8
1, 3, 4, 6, 7, 9
1, 3, 4, 6, 7, 10
1, 3, 4, 6, 7, 11
1, 3, 4, 6, 8, 9
1, 3, 4, 6, 8, 10
1, 3, 4, 6, 8, 11
1, 3, 4, 6, 9, 10
1, 3, 4, 6, 9, 11
1, 3, 4, 6, 10, 11
1, 3, 4, 7, 8, 9
1, 3, 4, 7, 8, 10
1, 3, 4, 7, 8, 11
1, 3, 4, 7, 9, 10
1, 3, 4, 7, 9, 11
1, 3, 4, 7, 10, 11
1, 3, 4, 8, 9, 10
1, 3, 4, 8, 9, 11
1, 3, 4, 8, 10, 11
1, 3, 4, 9, 10, 11
1, 3, 5, 6, 7, 8
1, 3, 5, 6, 7, 9
1, 3, 5, 6, 7, 10
1, 3, 5, 6, 7, 11
1, 3, 5, 6, 8, 9
1, 3, 5, 6, 8, 10
1, 3, 5, 6, 8, 11
1, 3, 5, 6, 9, 10
1, 3, 5, 6, 9, 11
1, 3, 5, 6, 10, 11
1, 3, 5, 7, 8, 9
1, 3, 5, 7, 8, 10
1, 3, 5, 7, 8, 11
1, 3, 5, 7, 9, 10
1, 3, 5, 7, 9, 11
1, 3, 5, 7, 10, 11
1, 3, 5, 8, 9, 10
1, 3, 5, 8, 9, 11
1, 3, 5, 8, 10, 11
1, 3, 5, 9, 10, 11
1, 3, 6, 7, 8, 9
1, 3, 6, 7, 8, 10
1, 3, 6, 7, 8, 11
1, 3, 6, 7, 9, 10
1, 3, 6, 7, 9, 11
1, 3, 6, 7, 10, 11
1, 3, 6, 8, 9, 10
1, 3, 6, 8, 9, 11
1, 3, 6, 8, 10, 11
1, 3, 6, 9, 10, 11
1, 3, 7, 8, 9, 10
1, 3, 7, 8, 9, 11
1, 3, 7, 8, 10, 11
1, 3, 7, 9, 10, 11
1, 3, 8, 9, 10, 11
1, 4, 5, 6, 7, 8
1, 4, 5, 6, 7, 9

TABLE 5-continued

| Nucleotide Sequence Combinations |
|---|
| 1, 4, 5, 6, 7, 10 |
| 1, 4, 5, 6, 7, 11 |
| 1, 4, 5, 6, 8, 9 |
| 1, 4, 5, 6, 8, 10 |
| 1, 4, 5, 6, 8, 11 |
| 1, 4, 5, 6, 9, 10 |
| 1, 4, 5, 6, 9, 11 |
| 1, 4, 5, 6, 10, 11 |
| 1, 4, 5, 7, 8, 9 |
| 1, 4, 5, 7, 8, 10 |
| 1, 4, 5, 7, 8, 11 |
| 1, 4, 5, 7, 9, 10 |
| 1, 4, 5, 7, 9, 11 |
| 1, 4, 5, 7, 10, 11 |
| 1, 4, 5, 8, 9, 10 |
| 1, 4, 5, 8, 9, 11 |
| 1, 4, 5, 8, 10, 11 |
| 1, 4, 5, 9, 10, 11 |
| 1, 4, 6, 7, 8, 9 |
| 1, 4, 6, 7, 8, 10 |
| 1, 4, 6, 7, 8, 11 |
| 1, 4, 6, 7, 9, 10 |
| 1, 4, 6, 7, 9, 11 |
| 1, 4, 6, 7, 10, 11 |
| 1, 4, 6, 8, 9, 10 |
| 1, 4, 6, 8, 9, 11 |
| 1, 4, 6, 8, 10, 11 |
| 1, 4, 6, 9, 10, 11 |
| 1, 4, 7, 8, 9, 10 |
| 1, 4, 7, 8, 9, 11 |
| 1, 4, 7, 8, 10, 11 |
| 1, 4, 7, 9, 10, 11 |
| 1, 4, 8, 9, 10, 11 |
| 1, 5, 6, 7, 8, 9 |
| 1, 5, 6, 7, 8, 10 |
| 1, 5, 6, 7, 8, 11 |
| 1, 5, 6, 7, 9, 10 |
| 1, 5, 6, 7, 9, 11 |
| 1, 5, 6, 7, 10, 11 |
| 1, 5, 6, 8, 9, 10 |
| 1, 5, 6, 8, 9, 11 |
| 1, 5, 6, 8, 10, 11 |
| 1, 5, 6, 9, 10, 11 |
| 1, 5, 7, 8, 9, 10 |
| 1, 5, 7, 8, 9, 11 |
| 1, 5, 7, 8, 10, 11 |
| 1, 5, 7, 9, 10, 11 |
| 1, 5, 8, 9, 10, 11 |
| 1, 6, 7, 8, 9, 10 |
| 1, 6, 7, 8, 9, 11 |
| 1, 6, 7, 8, 10, 11 |
| 1, 6, 7, 9, 10, 11 |
| 1, 6, 8, 9, 10, 11 |
| 1, 7, 8, 9, 10, 11 |
| 2, 3, 4, 5, 6, 7 |
| 2, 3, 4, 5, 6, 8 |
| 2, 3, 4, 5, 6, 9 |
| 2, 3, 4, 5, 6, 10 |
| 2, 3, 4, 5, 6, 11 |
| 2, 3, 4, 5, 7, 8 |
| 2, 3, 4, 5, 7, 9 |
| 2, 3, 4, 5, 7, 10 |
| 2, 3, 4, 5, 7, 11 |
| 2, 3, 4, 5, 8, 9 |
| 2, 3, 4, 5, 8, 10 |
| 2, 3, 4, 5, 8, 11 |
| 2, 3, 4, 5, 9, 10 |
| 2, 3, 4, 5, 9, 11 |
| 2, 3, 4, 5, 10, 11 |
| 2, 3, 4, 6, 7, 8 |
| 2, 3, 4, 6, 7, 9 |
| 2, 3, 4, 6, 7, 10 |
| 2, 3, 4, 6, 7, 11 |
| 2, 3, 4, 6, 8, 9 |
| 2, 3, 4, 6, 8, 10 |
| 2, 3, 4, 6, 8, 11 |
| 2, 3, 4, 6, 9, 10 |
| 2, 3, 4, 6, 9, 11 |
| 2, 3, 4, 6, 10, 11 |
| 2, 3, 4, 7, 8, 9 |
| 2, 3, 4, 7, 8, 10 |
| 2, 3, 4, 7, 8, 11 |
| 2, 3, 4, 7, 9, 10 |
| 2, 3, 4, 7, 9, 11 |
| 2, 3, 4, 7, 10, 11 |
| 2, 3, 4, 8, 9, 10 |
| 2, 3, 4, 8, 9, 11 |
| 2, 3, 4, 8, 10, 11 |
| 2, 3, 4, 9, 10, 11 |
| 2, 3, 5, 6, 7, 8 |
| 2, 3, 5, 6, 7, 9 |
| 2, 3, 5, 6, 7, 10 |
| 2, 3, 5, 6, 7, 11 |
| 2, 3, 5, 6, 8, 9 |
| 2, 3, 5, 6, 8, 10 |
| 2, 3, 5, 6, 8, 11 |
| 2, 3, 5, 6, 9, 10 |
| 2, 3, 5, 6, 9, 11 |
| 2, 3, 5, 6, 10, 11 |
| 2, 3, 5, 7, 8, 9 |
| 2, 3, 5, 7, 8, 10 |
| 2, 3, 5, 7, 8, 11 |
| 2, 3, 5, 7, 9, 10 |
| 2, 3, 5, 7, 9, 11 |
| 2, 3, 5, 7, 10, 11 |
| 2, 3, 5, 8, 9, 10 |
| 2, 3, 5, 8, 9, 11 |
| 2, 3, 5, 8, 10, 11 |
| 2, 3, 5, 9, 10, 11 |
| 2, 3, 6, 7, 8, 9 |
| 2, 3, 6, 7, 8, 10 |
| 2, 3, 6, 7, 8, 11 |
| 2, 3, 6, 7, 9, 10 |
| 2, 3, 6, 7, 9, 11 |
| 2, 3, 6, 7, 10, 11 |
| 2, 3, 6, 8, 9, 10 |
| 2, 3, 6, 8, 9, 11 |
| 2, 3, 6, 8, 10, 11 |
| 2, 3, 6, 9, 10, 11 |
| 2, 3, 7, 8, 9, 10 |
| 2, 3, 7, 8, 9, 11 |
| 2, 3, 7, 8, 10, 11 |
| 2, 3, 7, 9, 10, 11 |
| 2, 3, 8, 9, 10, 11 |
| 2, 4, 5, 6, 7, 8 |
| 2, 4, 5, 6, 7, 9 |
| 2, 4, 5, 6, 7, 10 |
| 2, 4, 5, 6, 7, 11 |
| 2, 4, 5, 6, 8, 9 |
| 2, 4, 5, 6, 8, 10 |
| 2, 4, 5, 6, 8, 11 |
| 2, 4, 5, 6, 9, 10 |
| 2, 4, 5, 6, 9, 11 |
| 2, 4, 5, 6, 10, 11 |
| 2, 4, 5, 7, 8, 9 |
| 2, 4, 5, 7, 8, 10 |
| 2, 4, 5, 7, 8, 11 |
| 2, 4, 5, 7, 9, 10 |
| 2, 4, 5, 7, 9, 11 |
| 2, 4, 5, 7, 10, 11 |
| 2, 4, 5, 8, 9, 10 |
| 2, 4, 5, 8, 9, 11 |
| 2, 4, 5, 8, 10, 11 |
| 2, 4, 5, 9, 10, 11 |
| 2, 4, 6, 7, 8, 9 |
| 2, 4, 6, 7, 8, 10 |
| 2, 4, 6, 7, 8, 11 |
| 2, 4, 6, 7, 9, 10 |
| 2, 4, 6, 7, 9, 11 |
| 2, 4, 6, 7, 10, 11 |
| 2, 4, 6, 8, 9, 10 |
| 2, 4, 6, 8, 9, 11 |
| 2, 4, 6, 8, 10, 11 |
| 2, 4, 6, 9, 10, 11 |
| 2, 4, 7, 8, 9, 10 |
| 2, 4, 7, 8, 9, 11 |

TABLE 5-continued

Nucleotide Sequence Combinations 2, 4, 7, 8, 10, 11
2, 4, 7, 9, 10, 11
2, 4, 8, 9, 10, 11
2, 5, 6, 7, 8, 9
2, 5, 6, 7, 8, 10
2, 5, 6, 7, 8, 11
2, 5, 6, 7, 9, 10
2, 5, 6, 7, 9, 11
2, 5, 6, 7, 10, 11
2, 5, 6, 8, 9, 10
2, 5, 6, 8, 9, 11
2, 5, 6, 8, 10, 11
2, 5, 6, 9, 10, 11
2, 5, 7, 8, 9, 10
2, 5, 7, 8, 9, 11
2, 5, 7, 8, 10, 11
2, 5, 7, 9, 10, 11
2, 5, 8, 9, 10, 11
2, 6, 7, 8, 9, 10
2, 6, 7, 8, 9, 11
2, 6, 7, 8, 10, 11
2, 6, 7, 9, 10, 11
2, 6, 8, 9, 10, 11
2, 7, 8, 9, 10, 11
3, 4, 5, 6, 7, 8
3, 4, 5, 6, 7, 9
3, 4, 5, 6, 7, 10
3, 4, 5, 6, 7, 11
3, 4, 5, 6, 8, 9
3, 4, 5, 6, 8, 10
3, 4, 5, 6, 8, 11
3, 4, 5, 6, 9, 10
3, 4, 5, 6, 9, 11
3, 4, 5, 6, 10, 11
3, 4, 5, 7, 8, 9
3, 4, 5, 7, 8, 10
3, 4, 5, 7, 8, 11
3, 4, 5, 7, 9, 10
3, 4, 5, 7, 9, 11
3, 4, 5, 7, 10, 11
3, 4, 5, 8, 9, 10
3, 4, 5, 8, 9, 11
3, 4, 5, 8, 10, 11
3, 4, 5, 9, 10, 11
3, 4, 6, 7, 8, 9
3, 4, 6, 7, 8, 10
3, 4, 6, 7, 8, 11
3, 4, 6, 7, 9, 10
3, 4, 6, 7, 9, 11
3, 4, 6, 7, 10, 11
3, 4, 6, 8, 9, 10
3, 4, 6, 8, 9, 11
3, 4, 6, 8, 10, 11
3, 4, 6, 9, 10, 11
3, 4, 7, 8, 9, 10
3, 4, 7, 8, 9, 11
3, 4, 7, 8, 10, 11
3, 4, 7, 9, 10, 11
3, 4, 8, 9, 10, 11
3, 5, 6, 7, 8, 9
3, 5, 6, 7, 8, 10
3, 5, 6, 7, 8, 11
3, 5, 6, 7, 9, 10
3, 5, 6, 7, 9, 11
3, 5, 6, 7, 10, 11
3, 5, 6, 8, 9, 10
3, 5, 6, 8, 9, 11
3, 5, 6, 8, 10, 11
3, 5, 6, 9, 10, 11
3, 5, 7, 8, 9, 10
3, 5, 7, 8, 9, 11
3, 5, 7, 8, 10, 11
3, 5, 7, 9, 10, 11
3, 5, 8, 9, 10, 11
3, 6, 7, 8, 9, 10
3, 6, 7, 8, 9, 11
3, 6, 7, 8, 10, 11
3, 6, 7, 9, 10, 11
3, 6, 8, 9, 10, 11
3, 7, 8, 9, 10, 11
4, 5, 6, 7, 8, 9
4, 5, 6, 7, 8, 10
4, 5, 6, 7, 8, 11
4, 5, 6, 7, 9, 10
4, 5, 6, 7, 9, 11
4, 5, 6, 7, 10, 11
4, 5, 6, 8, 9, 10
4, 5, 6, 8, 9, 11
4, 5, 6, 8, 10, 11
4, 5, 6, 9, 10, 11
4, 5, 7, 8, 9, 10
4, 5, 7, 8, 9, 11
4, 5, 7, 8, 10, 11
4, 5, 7, 9, 10, 11
4, 5, 8, 9, 10, 11
4, 6, 7, 8, 9, 10
4, 6, 7, 8, 9, 11
4, 6, 7, 8, 10, 11
4, 6, 7, 9, 10, 11
4, 6, 8, 9, 10, 11
4, 7, 8, 9, 10, 11
5, 6, 7, 8, 9, 10
5, 6, 7, 8, 9, 11
5, 6, 7, 8, 10, 11
5, 6, 7, 9, 10, 11
5, 6, 8, 9, 10, 11
5, 7, 8, 9, 10, 11
6, 7, 8, 9, 10, 11
1, 2, 3, 4, 5, 6, 7
1, 2, 3, 4, 5, 6, 8
1, 2, 3, 4, 5, 6, 9
1, 2, 3, 4, 5, 6, 10
1, 2, 3, 4, 5, 6, 11
1, 2, 3, 4, 5, 7, 8
1, 2, 3, 4, 5, 7, 9
1, 2, 3, 4, 5, 7, 10
1, 2, 3, 4, 5, 7, 11
1, 2, 3, 4, 5, 8, 9
1, 2, 3, 4, 5, 8, 10
1, 2, 3, 4, 5, 8, 11
1, 2, 3, 4, 5, 9, 10
1, 2, 3, 4, 5, 9, 11
1, 2, 3, 4, 5, 10, 11
1, 2, 3, 4, 6, 7, 8
1, 2, 3, 4, 6, 7, 9
1, 2, 3, 4, 6, 7, 10
1, 2, 3, 4, 6, 7, 11
1, 2, 3, 4, 6, 8, 9
1, 2, 3, 4, 6, 8, 10
1, 2, 3, 4, 6, 8, 11
1, 2, 3, 4, 6, 9, 10
1, 2, 3, 4, 6, 9, 11
1, 2, 3, 4, 6, 10, 11
1, 2, 3, 4, 7, 8, 9
1, 2, 3, 4, 7, 8, 10
1, 2, 3, 4, 7, 8, 11
1, 2, 3, 4, 7, 9, 10
1, 2, 3, 4, 7, 9, 11
1, 2, 3, 4, 7, 10, 11
1, 2, 3, 4, 8, 9, 10
1, 2, 3, 4, 8, 9, 11
1, 2, 3, 4, 8, 10, 11
1, 2, 3, 4, 9, 10, 11
1, 2, 3, 5, 6, 7, 8
1, 2, 3, 5, 6, 7, 9
1, 2, 3, 5, 6, 7, 10
1, 2, 3, 5, 6, 7, 11
1, 2, 3, 5, 6, 8, 9
1, 2, 3, 5, 6, 8, 10
1, 2, 3, 5, 6, 8, 11
1, 2, 3, 5, 6, 9, 10
1, 2, 3, 5, 6, 9, 11
1, 2, 3, 5, 6, 10, 11
1, 2, 3, 5, 7, 8, 9
1, 2, 3, 5, 7, 8, 10
1, 2, 3, 5, 7, 8, 11

TABLE 5-continued

Nucleotide Sequence Combinations 1, 2, 3, 5, 7, 9, 10
1, 2, 3, 5, 7, 9, 11
1, 2, 3, 5, 7, 10, 11
1, 2, 3, 5, 8, 9, 10
1, 2, 3, 5, 8, 9, 11
1, 2, 3, 5, 8, 10, 11
1, 2, 3, 5, 9, 10, 11
1, 2, 3, 6, 7, 8, 9
1, 2, 3, 6, 7, 8, 10
1, 2, 3, 6, 7, 8, 11
1, 2, 3, 6, 7, 9, 10
1, 2, 3, 6, 7, 9, 11
1, 2, 3, 6, 7, 10, 11
1, 2, 3, 6, 8, 9, 10
1, 2, 3, 6, 8, 9, 11
1, 2, 3, 6, 8, 10, 11
1, 2, 3, 6, 9, 10, 11
1, 2, 3, 7, 8, 9, 10
1, 2, 3, 7, 8, 9, 11
1, 2, 3, 7, 8, 10, 11
1, 2, 3, 7, 9, 10, 11
1, 2, 3, 8, 9, 10, 11
1, 2, 4, 5, 6, 7, 8
1, 2, 4, 5, 6, 7, 9
1, 2, 4, 5, 6, 7, 10
1, 2, 4, 5, 6, 7, 11
1, 2, 4, 5, 6, 8, 9
1, 2, 4, 5, 6, 8, 10
1, 2, 4, 5, 6, 8, 11
1, 2, 4, 5, 6, 9, 10
1, 2, 4, 5, 6, 9, 11
1, 2, 4, 5, 6, 10, 11
1, 2, 4, 5, 7, 8, 9
1, 2, 4, 5, 7, 8, 10
1, 2, 4, 5, 7, 8, 11
1, 2, 4, 5, 7, 9, 10
1, 2, 4, 5, 7, 9, 11
1, 2, 4, 5, 7, 10, 11
1, 2, 4, 5, 8, 9, 10
1, 2, 4, 5, 8, 9, 11
1, 2, 4, 5, 8, 10, 11
1, 2, 4, 5, 9, 10, 11
1, 2, 4, 6, 7, 8, 9
1, 2, 4, 6, 7, 8, 10
1, 2, 4, 6, 7, 8, 11
1, 2, 4, 6, 7, 9, 10
1, 2, 4, 6, 7, 9, 11
1, 2, 4, 6, 7, 10, 11
1, 2, 4, 6, 8, 9, 10
1, 2, 4, 6, 8, 9, 11
1, 2, 4, 6, 8, 10, 11
1, 2, 4, 6, 9, 10, 11
1, 2, 4, 7, 8, 9, 10
1, 2, 4, 7, 8, 9, 11
1, 2, 4, 7, 8, 10, 11
1, 2, 4, 7, 9, 10, 11
1, 2, 4, 8, 9, 10, 11
1, 2, 5, 6, 7, 8, 9
1, 2, 5, 6, 7, 8, 10
1, 2, 5, 6, 7, 8, 11
1, 2, 5, 6, 7, 9, 10
1, 2, 5, 6, 7, 9, 11
1, 2, 5, 6, 7, 10, 11
1, 2, 5, 6, 8, 9, 10
1, 2, 5, 6, 8, 9, 11
1, 2, 5, 6, 8, 10, 11
1, 2, 5, 6, 9, 10, 11
1, 2, 5, 7, 8, 9, 10
1, 2, 5, 7, 8, 9, 11
1, 2, 5, 7, 8, 10, 11
1, 2, 5, 7, 9, 10, 11
1, 2, 5, 8, 9, 10, 11
1, 2, 6, 7, 8, 9, 10
1, 2, 6, 7, 8, 9, 11
1, 2, 6, 7, 8, 10, 11
1, 2, 6, 7, 9, 10, 11
1, 2, 6, 8, 9, 10, 11
1, 2, 7, 8, 9, 10, 11
1, 3, 4, 5, 6, 7, 8
1, 3, 4, 5, 6, 7, 9
1, 3, 4, 5, 6, 7, 10
1, 3, 4, 5, 6, 7, 11
1, 3, 4, 5, 6, 8, 9
1, 3, 4, 5, 6, 8, 10
1, 3, 4, 5, 6, 8, 11
1, 3, 4, 5, 6, 9, 10
1, 3, 4, 5, 6, 9, 11
1, 3, 4, 5, 6, 10, 11
1, 3, 4, 5, 7, 8, 9
1, 3, 4, 5, 7, 8, 10
1, 3, 4, 5, 7, 8, 11
1, 3, 4, 5, 7, 9, 10
1, 3, 4, 5, 7, 9, 11
1, 3, 4, 5, 7, 10, 11
1, 3, 4, 5, 8, 9, 10
1, 3, 4, 5, 8, 9, 11
1, 3, 4, 5, 8, 10, 11
1, 3, 4, 5, 9, 10, 11
1, 3, 4, 6, 7, 8, 9
1, 3, 4, 6, 7, 8, 10
1, 3, 4, 6, 7, 8, 11
1, 3, 4, 6, 7, 9, 10
1, 3, 4, 6, 7, 9, 11
1, 3, 4, 6, 7, 10, 11
1, 3, 4, 6, 8, 9, 10
1, 3, 4, 6, 8, 9, 11
1, 3, 4, 6, 8, 10, 11
1, 3, 4, 6, 9, 10, 11
1, 3, 4, 7, 8, 9, 10
1, 3, 4, 7, 8, 9, 11
1, 3, 4, 7, 8, 10, 11
1, 3, 4, 7, 9, 10, 11
1, 3, 4, 8, 9, 10, 11
1, 3, 5, 6, 7, 8, 9
1, 3, 5, 6, 7, 8, 10
1, 3, 5, 6, 7, 8, 11
1, 3, 5, 6, 7, 9, 10
1, 3, 5, 6, 7, 9, 11
1, 3, 5, 6, 7, 10, 11
1, 3, 5, 6, 8, 9, 10
1, 3, 5, 6, 8, 9, 11
1, 3, 5, 6, 8, 10, 11
1, 3, 5, 6, 9, 10, 11
1, 3, 5, 7, 8, 9, 10
1, 3, 5, 7, 8, 9, 11
1, 3, 5, 7, 8, 10, 11
1, 3, 5, 7, 9, 10, 11
1, 3, 5, 8, 9, 10, 11
1, 3, 6, 7, 8, 9, 10
1, 3, 6, 7, 8, 9, 11
1, 3, 6, 7, 8, 10, 11
1, 3, 6, 7, 9, 10, 11
1, 3, 6, 8, 9, 10, 11
1, 3, 7, 8, 9, 10, 11
1, 4, 5, 6, 7, 8, 9
1, 4, 5, 6, 7, 8, 10
1, 4, 5, 6, 7, 8, 11
1, 4, 5, 6, 7, 9, 10
1, 4, 5, 6, 7, 9, 11
1, 4, 5, 6, 7, 10, 11
1, 4, 5, 6, 8, 9, 10
1, 4, 5, 6, 8, 9, 11
1, 4, 5, 6, 8, 10, 11
1, 4, 5, 6, 9, 10, 11
1, 4, 5, 7, 8, 9, 10
1, 4, 5, 7, 8, 9, 11
1, 4, 5, 7, 8, 10, 11
1, 4, 5, 7, 9, 10, 11
1, 4, 5, 8, 9, 10, 11
1, 4, 6, 7, 8, 9, 10
1, 4, 6, 7, 8, 9, 11
1, 4, 6, 7, 8, 10, 11
1, 4, 6, 7, 9, 10, 11
1, 4, 6, 8, 9, 10, 11
1, 4, 7, 8, 9, 10, 11
1, 5, 6, 7, 8, 9, 10

TABLE 5-continued

Nucleotide Sequence Combinations 1, 5, 6, 7, 8, 9, 11
1, 5, 6, 7, 8, 10, 11
1, 5, 6, 7, 9, 10, 11
1, 5, 6, 8, 9, 10, 11
1, 5, 7, 8, 9, 10, 11
1, 6, 7, 8, 9, 10, 11
2, 3, 4, 5, 6, 7, 8
2, 3, 4, 5, 6, 7, 9
2, 3, 4, 5, 6, 7, 10
2, 3, 4, 5, 6, 7, 11
2, 3, 4, 5, 6, 8, 9
2, 3, 4, 5, 6, 8, 10
2, 3, 4, 5, 6, 8, 11
2, 3, 4, 5, 6, 9, 10
2, 3, 4, 5, 6, 9, 11
2, 3, 4, 5, 6, 10, 11
2, 3, 4, 5, 7, 8, 9
2, 3, 4, 5, 7, 8, 10
2, 3, 4, 5, 7, 8, 11
2, 3, 4, 5, 7, 9, 10
2, 3, 4, 5, 7, 9, 11
2, 3, 4, 5, 7, 10, 11
2, 3, 4, 5, 8, 9, 10
2, 3, 4, 5, 8, 9, 11
2, 3, 4, 5, 8, 10, 11
2, 3, 4, 5, 9, 10, 11
2, 3, 4, 6, 7, 8, 9
2, 3, 4, 6, 7, 8, 10
2, 3, 4, 6, 7, 8, 11
2, 3, 4, 6, 7, 9, 10
2, 3, 4, 6, 7, 9, 11
2, 3, 4, 6, 7, 10, 11
2, 3, 4, 6, 8, 9, 10
2, 3, 4, 6, 8, 9, 11
2, 3, 4, 6, 8, 10, 11
2, 3, 4, 6, 9, 10, 11
2, 3, 4, 7, 8, 9, 10
2, 3, 4, 7, 8, 9, 11
2, 3, 4, 7, 8, 10, 11
2, 3, 4, 7, 9, 10, 11
2, 3, 4, 8, 9, 10, 11
2, 3, 5, 6, 7, 8, 9
2, 3, 5, 6, 7, 8, 10
2, 3, 5, 6, 7, 8, 11
2, 3, 5, 6, 7, 9, 10
2, 3, 5, 6, 7, 9, 11
2, 3, 5, 6, 7, 10, 11
2, 3, 5, 6, 8, 9, 10
2, 3, 5, 6, 8, 9, 11
2, 3, 5, 6, 8, 10, 11
2, 3, 5, 6, 9, 10, 11
2, 3, 5, 7, 8, 9, 10
2, 3, 5, 7, 8, 9, 11
2, 3, 5, 7, 8, 10, 11
2, 3, 5, 7, 9, 10, 11
2, 3, 5, 8, 9, 10, 11
2, 3, 6, 7, 8, 9, 10
2, 3, 6, 7, 8, 9, 11
2, 3, 6, 7, 8, 10, 11
2, 3, 6, 7, 9, 10, 11
2, 3, 6, 8, 9, 10, 11
2, 3, 7, 8, 9, 10, 11
2, 4, 5, 6, 7, 8, 9
2, 4, 5, 6, 7, 8, 10
2, 4, 5, 6, 7, 8, 11
2, 4, 5, 6, 7, 9, 10
2, 4, 5, 6, 7, 9, 11
2, 4, 5, 6, 7, 10, 11
2, 4, 5, 6, 8, 9, 10
2, 4, 5, 6, 8, 9, 11
2, 4, 5, 6, 8, 10, 11
2, 4, 5, 6, 9, 10, 11
2, 4, 5, 7, 8, 9, 10
2, 4, 5, 7, 8, 9, 11
2, 4, 5, 7, 8, 10, 11
2, 4, 5, 7, 9, 10, 11
2, 4, 5, 8, 9, 10, 11
2, 4, 6, 7, 8, 9, 10
2, 4, 6, 7, 8, 9, 11
2, 4, 6, 7, 8, 10, 11
2, 4, 6, 7, 9, 10, 11
2, 4, 6, 8, 9, 10, 11
2, 4, 7, 8, 9, 10, 11
2, 5, 6, 7, 8, 9, 10
2, 5, 6, 7, 8, 9, 11
2, 5, 6, 7, 8, 10, 11
2, 5, 6, 7, 9, 10, 11
2, 5, 6, 8, 9, 10, 11
2, 5, 7, 8, 9, 10, 11
2, 6, 7, 8, 9, 10, 11
3, 4, 5, 6, 7, 8, 9
3, 4, 5, 6, 7, 8, 10
3, 4, 5, 6, 7, 8, 11
3, 4, 5, 6, 7, 9, 10
3, 4, 5, 6, 7, 9, 11
3, 4, 5, 6, 7, 10, 11
3, 4, 5, 6, 8, 9, 10
3, 4, 5, 6, 8, 9, 11
3, 4, 5, 6, 8, 10, 11
3, 4, 5, 6, 9, 10, 11
3, 4, 5, 7, 8, 9, 10
3, 4, 5, 7, 8, 9, 11
3, 4, 5, 7, 8, 10, 11
3, 4, 5, 7, 9, 10, 11
3, 4, 5, 8, 9, 10, 11
3, 4, 6, 7, 8, 9, 10
3, 4, 6, 7, 8, 9, 11
3, 4, 6, 7, 8, 10, 11
3, 4, 6, 7, 9, 10, 11
3, 4, 6, 8, 9, 10, 11
3, 4, 7, 8, 9, 10, 11
3, 5, 6, 7, 8, 9, 10
3, 5, 6, 7, 8, 9, 11
3, 5, 6, 7, 8, 10, 11
3, 5, 6, 7, 9, 10, 11
3, 5, 6, 8, 9, 10, 11
3, 5, 7, 8, 9, 10, 11
3, 6, 7, 8, 9, 10, 11
4, 5, 6, 7, 8, 9, 10
4, 5, 6, 7, 8, 9, 11
4, 5, 6, 7, 8, 10, 11
4, 5, 6, 7, 9, 10, 11
4, 5, 6, 8, 9, 10, 11
4, 5, 7, 8, 9, 10, 11
4, 6, 7, 8, 9, 10, 11
5, 6, 7, 8, 9, 10, 11
1, 2, 3, 4, 5, 6, 7, 8
1, 2, 3, 4, 5, 6, 7, 9
1, 2, 3, 4, 5, 6, 7, 10
1, 2, 3, 4, 5, 6, 7, 11
1, 2, 3, 4, 5, 6, 8, 9
1, 2, 3, 4, 5, 6, 8, 10
1, 2, 3, 4, 5, 6, 8, 11
1, 2, 3, 4, 5, 6, 9, 10
1, 2, 3, 4, 5, 6, 9, 11
1, 2, 3, 4, 5, 6, 10, 11
1, 2, 3, 4, 5, 7, 8, 9
1, 2, 3, 4, 5, 7, 8, 10
1, 2, 3, 4, 5, 7, 8, 11
1, 2, 3, 4, 5, 7, 9, 10
1, 2, 3, 4, 5, 7, 9, 11
1, 2, 3, 4, 5, 7, 10, 11
1, 2, 3, 4, 5, 8, 9, 10
1, 2, 3, 4, 5, 8, 9, 11
1, 2, 3, 4, 5, 8, 10, 11
1, 2, 3, 4, 5, 9, 10, 11
1, 2, 3, 4, 6, 7, 8, 9
1, 2, 3, 4, 6, 7, 8, 10
1, 2, 3, 4, 6, 7, 8, 11
1, 2, 3, 4, 6, 7, 9, 10
1, 2, 3, 4, 6, 7, 9, 11
1, 2, 3, 4, 6, 7, 10, 11
1, 2, 3, 4, 6, 8, 9, 10
1, 2, 3, 4, 6, 8, 9, 11
1, 2, 3, 4, 6, 8, 10, 11
1, 2, 3, 4, 6, 9, 10, 11

TABLE 5-continued

Nucleotide Sequence Combinations 1, 2, 3, 4, 7, 8, 9, 10
1, 2, 3, 4, 7, 8, 9, 11
1, 2, 3, 4, 7, 8, 10, 11
1, 2, 3, 4, 7, 9, 10, 11
1, 2, 3, 4, 8, 9, 10, 11
1, 2, 3, 5, 6, 7, 8, 9
1, 2, 3, 5, 6, 7, 8, 10
1, 2, 3, 5, 6, 7, 8, 11
1, 2, 3, 5, 6, 7, 9, 10
1, 2, 3, 5, 6, 7, 9, 11
1, 2, 3, 5, 6, 7, 10, 11
1, 2, 3, 5, 6, 8, 9, 10
1, 2, 3, 5, 6, 8, 9, 11
1, 2, 3, 5, 6, 8, 10, 11
1, 2, 3, 5, 6, 9, 10, 11
1, 2, 3, 5, 7, 8, 9, 10
1, 2, 3, 5, 7, 8, 9, 11
1, 2, 3, 5, 7, 8, 10, 11
1, 2, 3, 5, 7, 9, 10, 11
1, 2, 3, 5, 8, 9, 10, 11
1, 2, 3, 6, 7, 8, 9, 10
1, 2, 3, 6, 7, 8, 9, 11
1, 2, 3, 6, 7, 8, 10, 11
1, 2, 3, 6, 7, 9, 10, 11
1, 2, 3, 6, 8, 9, 10, 11
1, 2, 3, 7, 8, 9, 10, 11
1, 2, 4, 5, 6, 7, 8, 9
1, 2, 4, 5, 6, 7, 8, 10
1, 2, 4, 5, 6, 7, 8, 11
1, 2, 4, 5, 6, 7, 9, 10
1, 2, 4, 5, 6, 7, 9, 11
1, 2, 4, 5, 6, 7, 10, 11
1, 2, 4, 5, 6, 8, 9, 10
1, 2, 4, 5, 6, 8, 9, 11
1, 2, 4, 5, 6, 8, 10, 11
1, 2, 4, 5, 6, 9, 10, 11
1, 2, 4, 5, 7, 8, 9, 10
1, 2, 4, 5, 7, 8, 9, 11
1, 2, 4, 5, 7, 8, 10, 11
1, 2, 4, 5, 7, 9, 10, 11
1, 2, 4, 5, 8, 9, 10, 11
1, 2, 4, 6, 7, 8, 9, 10
1, 2, 4, 6, 7, 8, 9, 11
1, 2, 4, 6, 7, 8, 10, 11
1, 2, 4, 6, 7, 9, 10, 11
1, 2, 4, 6, 8, 9, 10, 11
1, 2, 4, 7, 8, 9, 10, 11
1, 2, 5, 6, 7, 8, 9, 10
1, 2, 5, 6, 7, 8, 9, 11
1, 2, 5, 6, 7, 8, 10, 11
1, 2, 5, 6, 7, 9, 10, 11
1, 2, 5, 6, 8, 9, 10, 11
1, 2, 5, 7, 8, 9, 10, 11
1, 2, 6, 7, 8, 9, 10, 11
1, 3, 4, 5, 6, 7, 8, 9
1, 3, 4, 5, 6, 7, 8, 10
1, 3, 4, 5, 6, 7, 8, 11
1, 3, 4, 5, 6, 7, 9, 10
1, 3, 4, 5, 6, 7, 9, 11
1, 3, 4, 5, 6, 7, 10, 11
1, 3, 4, 5, 6, 8, 9, 10
1, 3, 4, 5, 6, 8, 9, 11
1, 3, 4, 5, 6, 8, 10, 11
1, 3, 4, 5, 6, 9, 10, 11
1, 3, 4, 5, 7, 8, 9, 10
1, 3, 4, 5, 7, 8, 9, 11
1, 3, 4, 5, 7, 8, 10, 11
1, 3, 4, 5, 7, 9, 10, 11
1, 3, 4, 5, 8, 9, 10, 11
1, 3, 4, 6, 7, 8, 9, 10
1, 3, 4, 6, 7, 8, 9, 11
1, 3, 4, 6, 7, 8, 10, 11
1, 3, 4, 6, 7, 9, 10, 11
1, 3, 4, 6, 8, 9, 10, 11
1, 3, 4, 7, 8, 9, 10, 11
1, 3, 5, 6, 7, 8, 9, 10
1, 3, 5, 6, 7, 8, 9, 11
1, 3, 5, 6, 7, 8, 10, 11
1, 3, 5, 6, 7, 9, 10, 11
1, 3, 5, 6, 8, 9, 10, 11
1, 3, 5, 7, 8, 9, 10, 11
1, 3, 6, 7, 8, 9, 10, 11
1, 4, 5, 6, 7, 8, 9, 10
1, 4, 5, 6, 7, 8, 9, 11
1, 4, 5, 6, 7, 8, 10, 11
1, 4, 5, 6, 7, 9, 10, 11
1, 4, 5, 6, 8, 9, 10, 11
1, 4, 5, 7, 8, 9, 10, 11
1, 4, 6, 7, 8, 9, 10, 11
1, 5, 6, 7, 8, 9, 10, 11
2, 3, 4, 5, 6, 7, 8, 9
2, 3, 4, 5, 6, 7, 8, 10
2, 3, 4, 5, 6, 7, 8, 11
2, 3, 4, 5, 6, 7, 9, 10
2, 3, 4, 5, 6, 7, 9, 11
2, 3, 4, 5, 6, 7, 10, 11
2, 3, 4, 5, 6, 8, 9, 10
2, 3, 4, 5, 6, 8, 9, 11
2, 3, 4, 5, 6, 8, 10, 11
2, 3, 4, 5, 6, 9, 10, 11
2, 3, 4, 5, 7, 8, 9, 10
2, 3, 4, 5, 7, 8, 9, 11
2, 3, 4, 5, 7, 8, 10, 11
2, 3, 4, 5, 7, 9, 10, 11
2, 3, 4, 5, 8, 9, 10, 11
2, 3, 4, 6, 7, 8, 9, 10
2, 3, 4, 6, 7, 8, 9, 11
2, 3, 4, 6, 7, 8, 10, 11
2, 3, 4, 6, 7, 9, 10, 11
2, 3, 4, 6, 8, 9, 10, 11
2, 3, 4, 7, 8, 9, 10, 11
2, 3, 5, 6, 7, 8, 9, 10
2, 3, 5, 6, 7, 8, 9, 11
2, 3, 5, 6, 7, 8, 10, 11
2, 3, 5, 6, 7, 9, 10, 11
2, 3, 5, 6, 8, 9, 10, 11
2, 3, 5, 7, 8, 9, 10, 11
2, 3, 6, 7, 8, 9, 10, 11
2, 4, 5, 6, 7, 8, 9, 10
2, 4, 5, 6, 7, 8, 9, 11
2, 4, 5, 6, 7, 8, 10, 11
2, 4, 5, 6, 7, 9, 10, 11
2, 4, 5, 6, 8, 9, 10, 11
2, 4, 5, 7, 8, 9, 10, 11
2, 4, 6, 7, 8, 9, 10, 11
2, 5, 6, 7, 8, 9, 10, 11
3, 4, 5, 6, 7, 8, 9, 10
3, 4, 5, 6, 7, 8, 9, 11
3, 4, 5, 6, 7, 8, 10, 11
3, 4, 5, 6, 7, 9, 10, 11
3, 4, 5, 6, 8, 9, 10, 11
3, 4, 5, 7, 8, 9, 10, 11
3, 4, 6, 7, 8, 9, 10, 11
3, 5, 6, 7, 8, 9, 10, 11
4, 5, 6, 7, 8, 9, 10, 11
1, 2, 3, 4, 5, 6, 7, 8, 9
1, 2, 3, 4, 5, 6, 7, 8, 10
1, 2, 3, 4, 5, 6, 7, 8, 11
1, 2, 3, 4, 5, 6, 7, 9, 10
1, 2, 3, 4, 5, 6, 7, 9, 11
1, 2, 3, 4, 5, 6, 7, 10, 11
1, 2, 3, 4, 5, 6, 8, 9, 10
1, 2, 3, 4, 5, 6, 8, 9, 11
1, 2, 3, 4, 5, 6, 8, 10, 11
1, 2, 3, 4, 5, 6, 9, 10, 11
1, 2, 3, 4, 5, 7, 8, 9, 10
1, 2, 3, 4, 5, 7, 8, 9, 11
1, 2, 3, 4, 5, 7, 8, 10, 11
1, 2, 3, 4, 5, 7, 9, 10, 11
1, 2, 3, 4, 5, 8, 9, 10, 11
1, 2, 3, 4, 6, 7, 8, 9, 10
1, 2, 3, 4, 6, 7, 8, 9, 11
1, 2, 3, 4, 6, 7, 8, 10, 11
1, 2, 3, 4, 6, 7, 9, 10, 11
1, 2, 3, 4, 6, 8, 9, 10, 11
1, 2, 3, 4, 7, 8, 9, 10, 11

TABLE 5-continued

Nucleotide Sequence Combinations 1, 2, 3, 5, 6, 7, 8, 9, 10
1, 2, 3, 5, 6, 7, 8, 9, 11
1, 2, 3, 5, 6, 7, 8, 10, 11
1, 2, 3, 5, 6, 7, 9, 10, 11
1, 2, 3, 5, 6, 8, 9, 10, 11
1, 2, 3, 5, 7, 8, 9, 10, 11
1, 2, 3, 6, 7, 8, 9, 10, 11
1, 2, 4, 5, 6, 7, 8, 9, 10
1, 2, 4, 5, 6, 7, 8, 9, 11
1, 2, 4, 5, 6, 7, 8, 10, 11
1, 2, 4, 5, 6, 7, 9, 10, 11
1, 2, 4, 5, 6, 8, 9, 10, 11
1, 2, 4, 5, 7, 8, 9, 10, 11
1, 2, 4, 6, 7, 8, 9, 10, 11
1, 2, 5, 6, 7, 8, 9, 10, 11
1, 3, 4, 5, 6, 7, 8, 9, 10
1, 3, 4, 5, 6, 7, 8, 9, 11
1, 3, 4, 5, 6, 7, 8, 10, 11
1, 3, 4, 5, 6, 7, 9, 10, 11
1, 3, 4, 5, 6, 8, 9, 10, 11
1, 3, 4, 5, 7, 8, 9, 10, 11
1, 3, 4, 6, 7, 8, 9, 10, 11
1, 3, 5, 6, 7, 8, 9, 10, 11
1, 4, 5, 6, 7, 8, 9, 10, 11
2, 3, 4, 5, 6, 7, 8, 9, 10
2, 3, 4, 5, 6, 7, 8, 9, 11
2, 3, 4, 5, 6, 7, 8, 10, 11
2, 3, 4, 5, 6, 7, 9, 10, 11
2, 3, 4, 5, 6, 8, 9, 10, 11
2, 3, 4, 5, 7, 8, 9, 10, 11
2, 3, 4, 6, 7, 8, 9, 10, 11
2, 3, 5, 6, 7, 8, 9, 10, 11
2, 4, 5, 6, 7, 8, 9, 10, 11
3, 4, 5, 6, 7, 8, 9, 10, 11
1, 2, 3, 4, 5, 6, 7, 8, 9, 10
1, 2, 3, 4, 5, 6, 7, 8, 9, 11
1, 2, 3, 4, 5, 6, 7, 8, 10, 11
1, 2, 3, 4, 5, 6, 7, 9, 10, 11
1, 2, 3, 4, 5, 6, 8, 9, 10, 11
1, 2, 3, 4, 5, 7, 8, 9, 10, 11
1, 2, 3, 4, 6, 7, 8, 9, 10, 11
1, 2, 3, 5, 6, 7, 8, 9, 10, 11
1, 2, 4, 5, 6, 7, 8, 9, 10, 11
1, 3, 4, 5, 6, 7, 8, 9, 10, 11
2, 3, 4, 5, 6, 7, 8, 9, 10, 11
1, 2, 3, 4, 5, 6, 7, 8, 9, 10, 11

REFERENCES

U.S. Pat. No. 4,522,811
U.S. Pat. No. 4,987,071
U.S. Pat. No. 5,093,246
U.S. Pat. No. 5,116,742
U.S. Pat. No. 5,328,470
U.S. Pat. No. 5,843,509B
U.S. Pat. No. 6,168,587
U.S. Pat. No. 6,194,389
U.S. Pat. No. 6,468,798
U.S. Pat. No. 6,471,996
U.S. Pat. No. 6,472,375
U.S. Pat. No. 6,649,192B
Abbas-Terki, T. et al. 2002. Lentiviral-Mediated RNA Interference. *Hum Gene Ther.* 13:2197-201.
Altschul, et al. 1990. Basic local alignment search tool. *J. Mol. Biol.* 215:403-10.
Altschul et al. 1997. Gapped BLAST and PSI-BLAST: a new generation of protein database search programs. Nucleic Acids Res. 25:3389-3402.
Andrew, S. E. 2001. Ocular manifestations of feline herpesvirus. J. Feline Med. Surg. 3:9-16.
Asnagli et al. 2002 Cutting Edge: Identification of an Alternative GATA-3 Promoter Directing Tissue-Specific Gene Expression in Mouse and Human. J. Immunol. 168:4268-4271.
Arias, C. F., M. A. Dector, L. Segovia, T. Lopez, M. Camacho, P. Isa, R. Espinosa, and S. Lopez. 2004. RNA silencing of rotavirus gene expression. Virus Res. 102:43-51.
August, J. R. 1984. Feline viral respiratory-disease—The carrier state, vaccination, and control. Vet. Clin. N. Am. Sm. An. Pract. 14:1159-1171.
Ausubel et al. (1993 Current Protocols in Molecular Biology, Greene Publ. Assoc. Inc. & John Wiley & Sons, Inc., Boston, Mass.)
Bagella et al. 1998. Cloning of murine CDK9/PITALRE and its tissue-specific expression in development. J. Cell. Physiol. 177:206-213.
Bagheri S. et al. 2004. Ribozymes in the Age of Molecular Therapeutics. Curr. Mol. Med. 4(5):489-506.
Bannasch, M. J., and J. E. Foley. 2005. Epidemiologic evaluation of multiple respiratory pathogens in cats in animal shelters. J. Feline Med. Surg. 7:109-119.
Barton, G. M. and Medzhitov, R. 2002. Retroviral delivery of small interfering RNA into primary cells. Proc Natl Acad Sci USA. 99:14943-5.
Bhuyan, P. K., K. Kariko, J. Capodici, J. Lubinski, L. M. Hook, H. M. Friedman, and D. Weissman. 2004. Short interfering RNA-mediated inhibition of herpes simplex virus type 1 gene expression and function during infection of human keratinocytes. J. Virol. 78:10276-10281.
Bistner, S. I., J. H. Carlson, J. N. Shively, and F. W. Scott. 1971. Ocular manifestations of feline herpesvirus infection. J. Am. Vet. Med. Assoc. 159:1223-1237.
Bittle, J. L., and W. J. Rubic. 1975. Immunogenic and protective effects of F-2 strain of feline viral rhinotracheitis virus. Am. J. Vet. Res. 36:89-91.
Borkhardt, A. 2002. Blocking oncogenes in malignant cells by RNA interference—New hope for a highly specific cancer treatment? Cancer Cell. 2:167-8.
Bristeau et al. 2001. Conserved as well as divergent regulatory elements account for expression of the human and rodent phynylalanine hydroxylase genes. Gene. 274:283-291.
Brummelkamp et al. 2002. A System for Stable Expression of Short Interfering RNAs in Mammalian Cells. Science. 296:550-553.
Burgener, D. C., and R. K. Maes. 1988. Glycoprotein-specific immune responses in cats after exposure to feline herpesvirus-1. Am. J. Vet. Res. 49:1673-1576.
Burleson, F. G., T. M. Chambers, and D. L. Wiedbrauk. 1992. Virology a laboratory manual. Academic Press, San Diego, Calif.
Calegari et al. 2002. Tissue-specific RNA interference in postimplantation mouse embryos with endoribonuclease-prepared short interfering RNA. Proc. Natl. Acad. Sci. USA 99(22): 14236-40.
Chen et al. 1994. Gene therapy for brain tumors: regression of experimental gliomas by adenovirus-mediated gene transfer in vivo. Proc. Natl. Acad. Sci. USA. 91:3054-3057.
Chen, A. A. et al., 2005. Quantum dots to monitor RNAi delivery and improve gene silencing. Nucleic Acids Res. 33:e190.
Chiu et al 2002. RNAI in Human Cells: Basic Structural and Functional Features of Small Interfering RNA. Mol. Cell. 10:549-561.
Chiu et al. 2000. Tumorigenesis in transgenic mice in which the SV40 T antigen is driven by the brain-specific FGF1 promoter. *Oncogene.* 19:6229-6239.

Clawson G. A. et al. 2004. Inhibition of papilloma progression by antisense oligonucleotides targeted to HPV11 E6/E7 RNA. Gene Ther. 11(17):1331-1341.

Cortez et al. 2000. Primary astrocytes retrovirally transduced with a tyrosine hydroxylase transgene driven by a glial-specific promoter elicit behavioral recovery in experimental Parkinsonism. J. Neurosci. Res. 59:39-46.

Crandell, R. A., J. R. Ganaway, J. A. Rehkempe, F. D. Maurer, and W. H. Niemann. 1961. Experimental feline viral rhinotracheitis. J. Am. Vet. Med. Assoc. 138:191.

Davis et al. 1986. Basic Methods in Molecular Biology. Elsevier, New York.

de los Santos, T., Q. Wu, S. de Avila Botton, and M. J. Grubman. 2005. Short hairpin RNA targeted to the highly conserved 2B nonstructural protein coding region inhibits replication of multiple serotypes of foot-and-mouth disease virus. Virol. 335:222-231.

Devroe, E. and Silver, P. A. 2002. Retrovirus-delivered siRNA. BMC Biotechnol. 2:15.

Downward, J. 2004. RNA interference. *BMJ.* 328:1245-1248.

Dykxhoorn, D. M. et al. 2006. The silent treatment: siRNAs as small molecule drugs. Gene Ther. 13:541-552.

Elbashir, S. M., J. Harborth, W. Lendeckel, A. Yalcin, K. Weber, and T. Tuschl. 2001. Duplexes of 21-nucleotide RNAs mediate RNA interference in cultured mammalian cells. Nature 411:494-498.

El-Meanawy M A, Schelling J R, Pozuelo F, Churpek M M, Ficker E K, Iyengar S, Sedor J R. 2000. Use of serial analysis of gene expression to generate kidney expression libraries. Am J Physiol 279:F383-392.

Fattal et al. 1998. Biodegradable polyalkylcyanoacrylate nanoparticles for the delivery of oligonucleotides. *J. Control Release.* 53(1-3):137-43.

Franz et al. 1993. Heart-specific targeting of firefly luciferase by the myosin light chain-2 promoter and developmental regulation in transgenic mice. Circ. Res. 73:629-638.

Gaskell, R. M., and R. C. Povey. 1977. Experimental induction of feline viral rhinotracheitis virus re-excretion in FVR-recovered cats. Vet. Rec. 100:128-133.

Gaultier et al. 1987. Alpha-DNA. IV: Alpha-anomeric and beta-anomeric tetrathymidylates covalently linked to intercalating oxazolopyridocarbazole. Synthesis, physicochemical properties and poly (rA) binding. Nucleic Acids. Res. 15:6625-6641.

Gitlin, L., and R. Andino. 2003. Nucleic acid-based immune system: the antiviral potential of mammalian RNA silencing. J. Virol. 77:7159-7165.

Gluzman, Y. 1981. SV40-transformed simian cells support the replication of early SV40 mutants. Cell. 23:175-182.

Godard et al. 1995. Antisense effects of cholesterol-oligodeoxynucleotide conjugates associated with poly(alkylcyanoacrylate) nanoparticles. Eur. J. Biochem. 232(2):404-10.

Goodchild J. 2004. Oligonucleotide therapeutics: 25 years agrowing. Curr. Opin. Mol. Ther. 6(2): 120-128

Grail, A., D. A. Harbour, and W. Chia. 1991. Restriction endonuclease mapping of the genome of feline herpesvirus type-1. Arch. Virol. 116:209-220.

Grassi G. et al. 2004. Therapeutic Potential of Hammerhead Ribozymes in the Treatment of Hyper-Proliferative Diseases. Curr. Pharm. Biotechnol. 5(4):369-386.

Hamajima et al. 1998. Intranasal Administration of HIV-DNA Vaccine Formulated with a Polymer, Carboxymethylcellulose, Augments Mucosal Antibody Production and Cell-Mediated Immune Response Clin. Immunol. Immunopathol. 88(2):205-10.

Hammond, S. M. 2005. Dicing and slicing: The core machinery of the RNA interference pathway. FEBS Lett. 579: 5822.

Hannon, G. J. 2002. RNA interference. Nature. 418:244-51.

Hargis, A. M., P. E. Ginn, J. Mansell, and R. L. Garber. 1999. Ulcerative facial and nasal dermatitis and stomatitis in cats associated with feline herpesvirus 1. Vet. Dermatol. 10:267-274.

Haselhoff and Gerlach. 1988. Simple RNA enzymes with new and highly specific endoribonuclease activities. Nature. 334:585-591.

Helps, C., N. Reeves, K. Egan, P. Howard, and D. Harbour. 2003. Detection of *Chlamydophila felis* and feline herpesvirus by multiplex real-time PCR analysis. J. Clin. Microbiol. 41:2734-2736.

Hendry P. et al. 2004. Redesigned and chemically-modified hammerhead ribozymes with improved activity and serum stability. BMC Chem. Biol. 4(1):1.

Hopp et al. 1988. A Short Polypeptide Marker Sequence Useful for Recombinant Protein Identification and Purification. Bio/Technology. 6:1204.

Huppi, K. et al. 2005. Defining and Assaying RNAi in Mammalian Cells *Mol. Cell.* 17:1-10.

Hutvagner and Zamore. 2002. RNAi: nature abhors a double-strand. Curr. Opin. Genet. Dev. 12, 225-232.

Inoue et al. 1987. Synthesis and hybridization studies on two complementary nona(2'-O-methyl)ribonucleotides. Nucleic Acids Res. 15:6131-6148.

Inoue et al. 1987A. Sequence-dependent hydrolysis of RNA using modified oligonucleotide splints and RNase H. FEBS Lett. 215:327-330.

Jackson, A. L., S. R. Bartz, J. Schelter, S. V. Kobayashi, J. Burchard, M. Mao, B. Li, G. Cavet, and P. S. Linsley. 2003. Expression profiling reveals off-target gene regulation by RNAi. Nat. Biotech. 21:635.

Jepsen J. S. et al. 2004. Locked Nucleic Acid: A Potent Nucleic Acid Analog in Therapeutics and Biotechnology. Oligonucleotides. 14(2): 130-146.

Jiamg M. et al. 2004. Gel-Based Application of siRNA to Human Epithelial Cancer Cells Induces RNAi-Dependent Apoptosis. Oligonucleotides. 14(4):239-48.

Kashani-Sabet M. 2004. Non-viral delivery of ribozymes for cancer gene therapy. *Expert Opin. Biol. Ther.* 4(11):1749-1755.

Kim, D. H., and J. J. Rossi. 2007. Strategies for silencing human disease using RNA interference. Nat. Rev. Genet. 8:173.

Kim, D. H., M. A. Behlke, S. D. Rose, M. S. Chang, S. Choi, and J. J. Rossi. 2005. Synthetic dsRNA Dicer substrates enhance RNAi potency and efficacy. Nat. Biotechnol. 23:222-226.

Kim, D. H., M. Longo, Y. Han, P. Lundberg, E. Cantin, and J. J. Rossi. 2004. Interferon induction by siRNAs and ssRNAs synthesized by phage polymerase. Nat. Biotechnol. 22:321-325.

Kumar, R. et al. 2003. High-Throughput Selection of Effective RNAi Probes for Gene Silencing. Genome Res. 13:2333-2340.

Kusov, Y., T. Kanda, A. Palmenberg, J.-Y. Sgro, and V. Gauss-Muller. 2006. Silencing of hepatitis A virus infection by small interfering RNAs. J. Virol. 80:5599-5610.

Lambert et al. 2001. Nanoparticulate systems for the delivery of antisense oligonucleotides. Drug Deliv. Rev. 47(1): 99-112.

Lappin, M. R., J. Andrews, D. Simpson, and W. A. Jensen. 2002. Use of serologic tests to predict resistance to feline herpesvirus 1, feline calicivirus, and feline parvovirus infection in cats. J. Am. Vet. Med. Assoc. 220:38-42.

Lee et al. 2002. Expression of small interfering RNAs targeted against HIV-1 rev transcripts in human cells. 20:500-505.

Lewis, D. et al. 2002. Efficient delivery of siRNA for inhibition of gene expression in postnatal mice. Nature Genetics. 32:107-108.

Lori, F. et al. 2002. Gene Therapy Approaches to HIV Infection. Am J Pharmacogenomics. 2:245-52.

Love, D. N. 1971. Feline herpesvirus associated with interstitial pneumonia in a kitten. Vet. Rec. 89:178.

Maeda, K., T. Horimoto, and T. Mikami. 1998. Properties and functions of feline herpesvirus type 1 glycoproteins. J. Vet. Med. Sci. 60:881-888.

Maeda, K., Y. Kawaguchi, M. Ono, Y. Inoshima, T. Miyazawa, Y. Tohya, C. Kai, and T. Mikami. 1994. A gD homologous gene of feline herpesvirus type 1 encodes a hemagglutinin (gp60). Virol. 202:1034-1038.

Maggs, D. J., M. R. Lappin, J. S. Reif, J. K. Collins, J. Carman, D. A. Dawson, and C. Bruns. 1999. Evaluation of serologic and viral detection methods for diagnosing feline herpesvirus-1 infection in cats with acute respiratory tract or chronic ocular disease. J. Am. Vet. Med. Assoc. 214: 502-507.

Maggs, D. J., M. P. Nasisse, and P. H. Kass. 2003. Efficacy of oral supplementation with L-lysine in cats latently infected with feline herpesvirus. Am. J. Vet. Res. 64:37-42.

Manfredsson, F. P. et al. 2005. rAAV-Mediated Nigral Parkin Over-Expression Is Neuroprotective in the 6-OHDA Rat Model of Parkinson's Disease. Molecular Therapy. 11:S24-S25.

Maniatis et al. 1982. Molecular Cloning, Cold Spring Harbor Laboratory, Plainview, N.Y.

Matta, H. et al. 2003. Use of Lentiviral Vectors for Delivery of Small Interfering RNA. Cancer Biol Ther. 2:206-10.

McCaffrey et al. 2002. Gene expression: RNA interference in adult mice. Nature. 418(6893):38-39.

McManus et al. 2002. Gene silencing using micro-RNA designed hairpins. RNA. 8:842-850.

McManus, M. T. and Sharp, P. A. 2002. Gene silencing in mammals by small interfering RNAs Nat Rev Genet. 3:737-47.

Meyers, E. and Miller, W. 1989. Optimal alignments in linear space. CABIOS, 4:11-17.

Miller, et al. 1989. Improved Retroviral Vectors for Gene Transfer and Expression. Biotechniques. 7:980-990.

Minamino et al. 2001. Inducible Gene Targeting in Postnatal Myocardium by Cardiac-Specific Expression of a Hormone-Activated Cre Fusion Protein. Circ. Res. 88:587-592.

Miyagishi and Taira. 2002. U6 promoterÂ-driven siRNAs with four uridine 3' overhangs efficiently suppress targeted gene expression in mammalian cells. Nature Biotechnol. 20:497-500.

Morris, M. C. et al. 2000. Translocating peptides and proteins and their use for gene delivery Curr Opin Biotechnol. 11:461-6.

Muratovska, A. and Eccles, M. R. 2004. Conjugate for efficient delivery of short interfering RNA (siRNA) into mammalian cells. FEBS Lett. 558:63-68.

Murphy F A, G. E., Horzinek M C, Studdert M J. 1999. Veterinary virology, 3rd ed., Academic Press, San Diego, Calif.

Nasisse, M. P., T. L. Glover, C. P. Moore, and B. J. Weigler. 1998. Detection of feline herpesvirus 1 DNA in corneas of cats with eosinophilic keratitis or corneal sequestration. Am. J. Vet. Res. 59:856-858.

Nasisse, M. P., J. S. Guy, M. G. Davidson, W. A. Sussman, and N. M. Fairley. 1989. Experimental ocular herpesvirus infection in the cat. Sites of virus replication, clinical features and effects of corticosteroid administration. Invest. Ophthalmol. Vis. Sci. 30:1758-1768.

Navankasattusas et al. 1992. A ubiquitous factor (HF-1a) and a distinct muscle factor (HF-1b/MEF-2) form an E-box-independent pathway for cardiac muscle gene expression. Mol. Cell Biol. 12:1469-1479.

Needleman and Wunsch. 1970. A general method applicable to the search for similarities in the amino acid sequence of two proteins. J. Mol. Biol. 48:443-453.

Nguyen Van, N., K. Taglinger, C. R. Helps, S. Tasker, T. J. Gruffydd-Jones, and M. J. Day. 2006. Measurement of cytokine mRNA expression in intestinal biopsies of cats with inflammatory enteropathy using quantitative real-time RT-PCR. Vet. Immunol. Immunopathol. 113:404-414.

Paddison et al. 2002. Short hairpin RNAs (shRNAs) induce sequence-specific silencing in mammalian cells. Genes Dev. 16:948-958.

Pai, S. I. et al. 2005. Epigenetic changes in virus-associated human cancers. Cell Research. 15:262-271.

Paul et al. 2002. Effective expression of small interfering RNA in human cells. Nature Biotechnol. 20:505-508.

Persengiev, S. P., X. Zhu, and M. R. Green. 2004. Nonspecific, concentration-dependent stimulation and repression of mammalian gene expression by small interfering RNAs (siRNAs). RNA 10:12-18.

Povey, R. C. 1976. Feline respiratory-infections—clinical review. Can. Vet. J. 17:93-100.

Putnam, D. A. 1996. Antisense strategies and therapeutic applications. Am. J. Health Syst. Pharm. 53(2):151-160 erratum at Am. J. Health Syst. Pharm. 53(3):325.

Qin, X. F. et al 2003. Inhibiting HIV-1 infection in human T cells by lentiviral-mediated delivery of small interfering RNA against CCR5. Proc Natl Acad Sci USA. 100:183-8.

Raab, R. M. and Stephanopoulos, G. 2004. Dynamics of gene silencing by RNA interference. Biotechnol. Bioeng. 88:121-132.

Raoul, C. et al. 2005. Lentiviral-Mediated Silencing of SOD1 through RNA Interference Delays Disease Onset and Progression in a Mouse Model of ALS. Nat. Med. 11 (423-428).

Rodriguez-Lebron, E. et al. 2005. Intrastriatal rAAV-mediated delivery of anti-huntingtin shRNAs induces partial reversal of disease progression in R6/1 Huntington's disease transgenic mice. Molecular Therapy. 12:618-633.

Rota, P. A., R. K. Maes, and W. T. Ruyechan. 1986. Physical characterization of the genome of feline herpesvirus-1. Virol. 154:168.

Rozen, S., and H. J. Skaletsky. 2000. Primer3 on the WWW for general users and for biologist programmers. Humana Press.

Ruether et al. 1993. Inducible formation of liver tumors in transgenic mice. Oncogene. 8:87-93.

Samara et al. 2002. Mol. Cell Biol. 22:4702-4713.

Sambrook, et al. Molecular Cloning: A Laboratory Manual, Third Edition, Cold Spring Harbor, N.Y., (2001)

Sarkar T. et al. 2005. Condensation of oligonucleotides assembled into nicked and gapped duplexes: potential structures for oligonucleotide delivery. Nucleic Acids Research. 33(1):143-151.

Scherr, M. et al. 2003. Gene Silencing Mediated by Small Interfering RNAs in Mammalian Cells. Curr. Med. Chem. 10:245-56.

Scherr, M. et al. 2003. Lentivirus-mediated antagomir expression for specific inhibition of miRNA function. Cell Cycle. 2:251-7.

Schwab et al. 1994. An approach for new anticancer drugs: Oncogene-targeted antisense DNA. Ann. Oncol. 5 Suppl. 4:55-8.

Sharp, P. A. 2001. RNA interference. Genes Dev. 15:485-490.

Shen, C. et al 2003. Gene silencing by adenovirus-delivered siRNA. FEBS Lett. 539:111-4.

Shuey, D. J. et al. 2002. RNAi: gene-silencing in therapeutic intervention. Drug Discovery Today. 7:1040-6.

Simeoni, F. et al. 2003. Insight into the mechanism of the peptide-based gene delivery system MPG: implications for delivery of siRNA into mammalian cells. Nucleic Acids Res. 31:2717-24.

Sinn et al. 2000. Identification of three human renin mRNA isoforms from alternative tissue-specific transcriptional initiation. 3:25-31.

Song, E. et al. 2003. RNA interference targeting Fas protects mice from fulminant hepatitis. Nat Med. 9:347-51.

Sorensen, D. R. et al. 2003. Gene Silencing by Systemic Delivery of Synthetic siRNAs in Adult Mice. J Mol Biol. 327:761-6.

Spagnou, S. et al. 2004. Lipidic carriers of siRNA: differences in the formulation, cellular uptake, and delivery with plasmid DNA. Biochemistry. 43:13348-13356.

Stelzl, E., Z. Muller, E. Marth, and H. H. Kessler. 2004. Rapid quantification of hepatitis B virus DNA by automated sample preparation and real-time PCR. J. Clin. Microbiol. 42:2445-2449.

Stiles, J. 2003. Feline herpesvirus. Clin. Tech. Sm. An. Pract. 18:178-185.

Stiles, J. 1995. Treatment of cats with ocular disease attributable to herpesvirus infection: 17 cases (1983-1993). J. Am. Vet. Med. Assoc. 207:599-603.

Sui et al. 2002. A DNA vector-based RNAi technology to suppress gene expression in mammalian cells. Proc. Natl. Acad. Sci. USA. 99(6):5515-5520.

Tanaka et al. 1999. Characterization of novel promoter and enhancer elements of the mouse homologue of the Dent disease gene, CLCN5, implicated in X-linked hereditary nephrolithiasis. Genomics. 58:281-292.

Tuschl, T. 2002. Expanding small RNA interference. Nature Biotechnol. 20:446-448.

Velasco et al. 2001. Vascular gene transfer driven by endoglin and ICAM-2 endothelial-specific promoters. Gene Ther. 8:897-904.

Vibert et al. 1989. The brain-specific gene for rat aldolase C possesses an unusual housekeeping-type promoter. Eur. J. Biochem. 181:33-39.

Willoughby, K. 1996. Ph.D. thesis. University of Liverpool, Neston, UK.

Wilson et al. 1984. The structure of an antigenic determinant in a protein. *Cell.* 37:767-778.

Wilson, J. A., and C. D. Richardson. 2005. Hepatitis C virus replicons escape RNA interference induced by a short interfering RNA directed against the NS5b coding region. J. Virol. 79:7050-7058.

Wong, M. L., and J. F. Medrano. 2005. Real-time PCR for mRNA quantitation. Biotechniques 39:75-85.

Xia et al. 2002. siRNA-mediated gene silencing in vitro and in vivo. Nature Biotechnol. 20(10):1006-10.

Yu et al. 2002. RNA interference by expression of short-interfering RNAs and hairpin RNAs in mammalian cells. Proc. Natl. Acad. Sci. USA. 99(9):6047-6052.

Zeng et al. 2002. Both Natural and Designed Micro RNAs Can Inhibit the Expression of Cognate mRNAs When Expressed in Human Cells. Mol. Cell. 9:1327-1333.

Zhang et al. 2001. Characterization of the genomic structure and tissue-specific promoter of the human nuclear receptor NR5A2 (hB1F) gene. Gene. 273:239-249.

Zhu et al. 1993. A novel, tissue-restricted zinc-finger protein (HF-1b) binds to the cardiac regulatory element (HF-1b/MEF-2) in the rat myosin light-chain2 gene. Mol. Cell Biol. 13:4432-4444.

---

We claim:

1. A method of decreasing expression of FHV-1 DNA polymerase and/or glycoprotein D in cells, comprising administering a composition comprising a carrier and an effective amount of a polynucleotide that reduces expression of FHV-1 DNA polymerase and/or glycoprotein D, wherein said polynucleotide is selected from an interfering RNA that targets:
   a) nucleotides 23-5, 70-52, 95-77, 121-103 or 144-126 of the FHV-1 polymerase gene set forth in GenBank Accession No. AF079125 (SEQ ID NO:2); and/or
   b) nucleotides 1076-1058, 1351-1333, 1397-1379, 1556-1538 or 1591-1573 of the FHV-1 glycoprotein D gene set forth in GenBank Accession No. D30767 (SEQ ID NO:3).

2. A method of decreasing expresion of FHV-1 DNA polymerase and/or glycoprotein D in cells, comprising adminis-tering a composition comprising a carrier and an effective amount of a polynucleotide that reduces expression of FHV-1 DNA polymerase and/or glycoprotein D, wherein said polynucleotide is an interfering RNA sequence comprising SEQ ID NO: 7, 8, 9, 10, 11, 12, 13, 14, 15, 16 or 17.

3. A method of decreasing expresion of FHV-1 DNA polymerase and/or glycoprotein D in cells, comprising administering a composition comprising a carrier and an effective amount of interfering RNA molecules that reduce expression of FHV-1 DNA polymerase and/or glycoprotein D, wherein said composition comprises a combination of two or more interfering RNA molecules comprising SEQ ID NOs: 7, 8, 9, 10, 11, 12, 13, 14, 15, 16 or 17.

4. The method according to claim 2, wherein said interfering RNA sequence consists of SEQ ID NO: 7, 8, 9, 10, 11, 12, 13, 14, 15, 16 or 17.

5. The method according to claim 3, wherein said interfering RNA molecules have a sequence consisting of SEQ ID NO: 7, 8, 9, 10, 11, 12, 13, 14, 15, 16 or 17.

6. The method according to claim 3, wherein said combination of interfering RNA molecules have a sequence comprising SEQ ID NO: 7 and SEQ ID NO: 9.

7. The method according to claim 3, wherein said combination of interfering RNA molecules have a sequence consisting of SEQ ID NO: 7 and SEQ ID NO: 9.

8. The method according to claim 3, wherein said composition comprises a carrier and an effective amount of SEQ ID NO: 7 and SEQ ID NO: 9.

9. The method according to claim 1, wherein said composition is administered to a mucosal surface of a feline.

10. The method according to claim 2, wherein said composition is administered to a mucosal surface of a feline.

11. The method according to claim 3, wherein said composition is administered to a mucosal surface of a feline.

12. The method according to claim 4, wherein said interfering RNA is administered to a mucosal surface of a feline.

13. The method according to claim 5, wherein said interfering RNA molecules are administered to a mucosal surface of a feline.

14. The method according to claim 6, wherein said combination of interfering RNA molecules are administered to a mucosal surface of a feline.

15. The method according to claim 7, wherein said combination of interfering RNA molecules are administered to a mucosal surface of a feline.

16. The method according to claim 8, wherein said composition is administered to a mucosal surface of a feline.

17. The method according to claim 3, wherein said combination of two or more interfering RNA molecules are double stranded siRNA molecules of between 16 and 30 nucleotides, said double stranded siRNA molecules comprising a first sequence comprising SEQ ID NO: 7, 8, 9, 10, 11, 12, 13, 14, 15, 16 or 17 and a second sequence that is complementary thereto, wherein said siRNA molecule contains 0, 1, 2, 3 or 4 base mismatches.

18. The method according to claim 17, wherein said combination of nucleotides are SEQ ID NOs: 7 and 9 or SEQ ID NOs: 7 and 12.

* * * * *

UNITED STATES PATENT AND TRADEMARK OFFICE
CERTIFICATE OF CORRECTION

PATENT NO. : 7,977,321 B2                Page 1 of 1
APPLICATION NO. : 12/370213
DATED : July 12, 2011
INVENTOR(S) : Stephen A. Kania et al.

It is certified that error appears in the above-identified patent and that said Letters Patent is hereby corrected as shown below:

Column 4,
Line 21, "Control averaged" should read --Control = averaged--.

Column 7,
Line 57, "car still" should read --can still--.

Column 36,
Lines 38-39, "gD 3     UUGAUGUUACAUAACGUACUUCAG     1076-1058"
              (SEQ ID NO: 14) Cug
should read
              --gD3     UUGAUGUUACAUAACGUACUUCAG     1076-1058--.
              (SEQ ID NO: 14) Cug Signed and Sealed this
Eighteenth Day of October, 2011

David J. Kappos
*Director of the United States Patent and Trademark Office*

SEQUENCE LISTING

```
<160> NUMBER OF SEQ ID NOS: 39

<210> SEQ ID NO 1
<211> LENGTH: 1002
<212> TYPE: DNA
<213> ORGANISM: Felis catus
<220> FEATURE:
<221> NAME/KEY: exon
<222> LOCATION: (1)..(1002)

<400> SEQUENCE: 1 atg gtg aag gtc ggt gtg aac gga ttt ggc cgt att ggg cgc ctg gtc      48
Met Val Lys Val Gly Val Asn Gly Phe Gly Arg Ile Gly Arg Leu Val
1               5                   10                  15 acc agg gct gct ttt aac tct ggc aaa gtg gac att gtc gcc atc aat      96
Thr Arg Ala Ala Phe Asn Ser Gly Lys Val Asp Ile Val Ala Ile Asn
                20                  25                  30 gac ccc ttc att gac ctc aac tac atg gtc tac atg ttc cag tat gat     144
Asp Pro Phe Ile Asp Leu Asn Tyr Met Val Tyr Met Phe Gln Tyr Asp
            35                  40                  45 tcc acc cac ggc aaa ttc cac ggc aca gtc aag gct gag aac ggg aaa     192
Ser Thr His Gly Lys Phe His Gly Thr Val Lys Ala Glu Asn Gly Lys
        50                  55                  60
```

```
ctt gtc atc aat gga aag ccc atc acc atc ttc cag gag cga gat ccc        240
Leu Val Ile Asn Gly Lys Pro Ile Thr Ile Phe Gln Glu Arg Asp Pro
 65                  70                  75                  80 gcc aac atc aaa tgg ggt gat gct ggt gct gag tat gtt gtg gag tct        288
Ala Asn Ile Lys Trp Gly Asp Ala Gly Ala Glu Tyr Val Val Glu Ser
                 85                  90                  95 act ggg gtc ttc acc acc atg gag aag gct ggg gct cac ttg aag ggt        336
Thr Gly Val Phe Thr Thr Met Glu Lys Ala Gly Ala His Leu Lys Gly
            100                 105                 110 ggg gcc aag agg gtc atc atc tct gcc cct tct gct gat gcc ccc atg        384
Gly Ala Lys Arg Val Ile Ile Ser Ala Pro Ser Ala Asp Ala Pro Met
        115                 120                 125 ttt gtg atg ggc gtg aac cac gag aag tat gac aac tct ctc aag att        432
Phe Val Met Gly Val Asn His Glu Lys Tyr Asp Asn Ser Leu Lys Ile
    130                 135                 140 gtc agc aat gcc tcc tgc acc acc aac tgc ctg gcc cct ctg gcc aag        480
Val Ser Asn Ala Ser Cys Thr Thr Asn Cys Leu Ala Pro Leu Ala Lys
145                 150                 155                 160 gtc atc cat gac cac ttc ggc atc gtg gag gga ctc atg acc aca gtc        528
Val Ile His Asp His Phe Gly Ile Val Glu Gly Leu Met Thr Thr Val
                165                 170                 175 cat gcc atc acc gcc acc cag aag acc gtg gac ggc ccc tct ggg aag        576
His Ala Ile Thr Ala Thr Gln Lys Thr Val Asp Gly Pro Ser Gly Lys
            180                 185                 190 ctg tgg cgt gat ggc cga ggg gct gcc cag aac atc atc cct gct tct        624
Leu Trp Arg Asp Gly Arg Gly Ala Ala Gln Asn Ile Ile Pro Ala Ser
        195                 200                 205 act ggc gct gcc aag gct gtg ggc aag gtc atc cca gag ctg aat ggg        672
Thr Gly Ala Ala Lys Ala Val Gly Lys Val Ile Pro Glu Leu Asn Gly
    210                 215                 220 aag ctc act ggc atg gcc ttc cgt gtc ccc acc ccc aat gtg tcc gtc        720
Lys Leu Thr Gly Met Ala Phe Arg Val Pro Thr Pro Asn Val Ser Val
225                 230                 235                 240 gtg gat ctg acc tgc cgc ctg gag aaa gct gcc aaa tac gat gac atc        768
Val Asp Leu Thr Cys Arg Leu Glu Lys Ala Ala Lys Tyr Asp Asp Ile
                245                 250                 255 aag aag gtg gtg aag cag gca tca gag ggc ccc ctc aag ggc atc ctg        816
Lys Lys Val Val Lys Gln Ala Ser Glu Gly Pro Leu Lys Gly Ile Leu
            260                 265                 270 ggc tac act gag gac cag gtt gtc tcc tgc gac ttt aac agt gac acc        864
Gly Tyr Thr Glu Asp Gln Val Val Ser Cys Asp Phe Asn Ser Asp Thr
        275                 280                 285 cac tct tcc acc ttc gac gct ggg gct ggc att gcg ctc aat gac cac        912
His Ser Ser Thr Phe Asp Ala Gly Ala Gly Ile Ala Leu Asn Asp His
    290                 295                 300 ttt gtc aag ctc att tcc tgg tat gac aat gaa ttt ggc tac agc aac        960
Phe Val Lys Leu Ile Ser Trp Tyr Asp Asn Glu Phe Gly Tyr Ser Asn
305                 310                 315                 320 cgg gtg gtg gac ctc atg gcc cac atg gcc tcc aag gag taa               1002
Arg Val Val Asp Leu Met Ala His Met Ala Ser Lys Glu
                325                 330

<210> SEQ ID NO 2
<211> LENGTH: 180
<212> TYPE: DNA
<213> ORGANISM: Felid herpesvirus 1
<220> FEATURE:
<221> NAME/KEY: exon
<222> LOCATION: (1)..(180)

<400> SEQUENCE: 2
```

```
gct aat ggt ctt ctc cca tgt cta cag ata gcc gcc act gta act acg    48
Ala Asn Gly Leu Leu Pro Cys Leu Gln Ile Ala Ala Thr Val Thr Thr
1               5                   10                  15 ata gga aga gat atg cta ctc aat act aaa cat tac gtg gag tct aga    96
Ile Gly Arg Asp Met Leu Leu Asn Thr Lys His Tyr Val Glu Ser Arg
            20                  25                  30 tgg gca act aga gaa gga gtc gaa agt gat ttt cca gaa gct atg acc   144
Trp Ala Thr Arg Glu Gly Val Glu Ser Asp Phe Pro Glu Ala Met Thr
        35                  40                  45 gtt act att ccg gat aaa ccc tat aat gta cag gta                   180
Val Thr Ile Pro Asp Lys Pro Tyr Asn Val Gln Val
    50                  55                  60

<210> SEQ ID NO 3
<211> LENGTH: 2317
<212> TYPE: DNA
<213> ORGANISM: Felid herpesvirus 1
<220> FEATURE:
<221> NAME/KEY: exon
<222> LOCATION: (860)..(1984)

<400> SEQUENCE: 3
gagctcccgg aggaggatat acataactac tcagattgtc gtgcgactaa tatgtttgtt    60
ccgagagagc ccctcagtca agttcttggt tctcaaagtc tactggttgg tagtttaggt   120
ttccagataa ttactcaacc ctggcaactg aagcagaatg aaagttatga tggactaaga   180
aatgcctctc ttgaaccccg acaccttgac tccagtaacg atcgtgatct actagatgaa   240
actgaaatga ttgatcgat tattacgact ccaccaccaa cccatccaaa aggtgtcaat   300
gggggtttcc tccaagatct accaattatc gagcctacga ccgaaccatg cttagtacat   360
acaaagatca ttgggatcgg aacagtagtc gttgtatttt tgttatttat tctcatatcc   420
ctatgtgttt atacttgcgt tctacgatcc cgcatcggta tggtagatcg cgcctatgtg   480
aaacaagtac gatttaattc caatccatca tatcaacagt tgacaagata cccccaacca   540
taataaactg attaaattta attaaagtct catatgtggg gctgtgggga cgaggggtgt   600
ggggacgagg ggctgtgggg acgaggggct gtgggacgag gggctgtggg gacgaggggc   660
tgtggggacg aggggctgtg gggacgatta caaccgataa atgtcgtata tgaaatgtgg   720
tgttaacata acacggattt tttaagcaca ccacatgaca cacccccacg ataacggttt   780
aaatcaccag ctatgtgaac tgccctccat tctactcaaa tgagtggtgg tgtgtggcat   840
attagaacca tttcgtcta atg atg aca cgt cta cat ttt tgg tgg tgt gga    892
                      Met Met Thr Arg Leu His Phe Trp Trp Cys Gly
                       1               5                  10 atc ttt gcg gtc ctg aaa tat ctg gta tgt act tca agc ctt acg acc   940
Ile Phe Ala Val Leu Lys Tyr Leu Val Cys Thr Ser Ser Leu Thr Thr
             15                  20                  25 acg cca aaa aca act acg gtt tat gtg aag gga ttt aat ata cct cca   988
Thr Pro Lys Thr Thr Thr Val Tyr Val Lys Gly Phe Asn Ile Pro Pro
        30                  35                  40 cta cgc tac aat tat act caa gcc aga atc gtg cca aaa att ccc cag  1036
Leu Arg Tyr Asn Tyr Thr Gln Ala Arg Ile Val Pro Lys Ile Pro Gln
    45                  50                  55 gcg atg gat ccg aag ata aca gct gaa gta cgt tat gta aca tca atg  1084
Ala Met Asp Pro Lys Ile Thr Ala Glu Val Arg Tyr Val Thr Ser Met
60                  65                  70                  75 gat tca tgt ggg atg gtg gca ttg ata tca gag ccg gat ata gac gct  1132
Asp Ser Cys Gly Met Val Ala Leu Ile Ser Glu Pro Asp Ile Asp Ala
                80                  85                  90 act att cga acc ata caa cta tct caa aaa aaa aca tat aac gcg act  1180
```

```
                Thr Ile Arg Thr Ile Gln Leu Ser Gln Lys Lys Thr Tyr Asn Ala Thr
                                 95                 100                  105 ata agt tgg ttt aag gta acc cag ggt tgt gaa tac cct atg ttt ctt          1228
Ile Ser Trp Phe Lys Val Thr Gln Gly Cys Glu Tyr Pro Met Phe Leu
            110                 115                 120 atg gat atg aga ctt tgt gat cct aaa cgg gaa ttt gga ata tgt gct          1276
Met Asp Met Arg Leu Cys Asp Pro Lys Arg Glu Phe Gly Ile Cys Ala
        125                 130                 135 tta cgg tcg cct tca tat tgg ttg gaa cct tta aca aag tat atg ttc          1324
Leu Arg Ser Pro Ser Tyr Trp Leu Glu Pro Leu Thr Lys Tyr Met Phe
140                 145                 150                 155 cta aca gac gat gaa ctg ggt ttg att atg atg gcc ccg gcc caa ttt          1372
Leu Thr Asp Asp Glu Leu Gly Leu Ile Met Met Ala Pro Ala Gln Phe
                160                 165                 170 aat caa gga caa tat cga aga gtt ata acc atc gat ggt tcc atg ttt          1420
Asn Gln Gly Gln Tyr Arg Arg Val Ile Thr Ile Asp Gly Ser Met Phe
            175                 180                 185 tat aca gat ttt atg gta caa cta tct cca acg cca tgt tgg ttc gca          1468
Tyr Thr Asp Phe Met Val Gln Leu Ser Pro Thr Pro Cys Trp Phe Ala
        190                 195                 200 aaa ccc gat aga tac gaa gag att cta cat gaa tgg tgt cga aat gtt          1516
Lys Pro Asp Arg Tyr Glu Glu Ile Leu His Glu Trp Cys Arg Asn Val
    205                 210                 215 aaa act att ggc ctt gat gga gct cgt gat tac cac tat tat tgg gta          1564
Lys Thr Ile Gly Leu Asp Gly Ala Arg Asp Tyr His Tyr Tyr Trp Val
220                 225                 230                 235 ccc tat aac cca caa cct cac cat aaa gcc gta ctc tta tat tgg tat          1612
Pro Tyr Asn Pro Gln Pro His His Lys Ala Val Leu Leu Tyr Trp Tyr
                240                 245                 250 cgg act cat ggc cga gaa ccc cca gta aga ttc caa gag gcc att cga          1660
Arg Thr His Gly Arg Glu Pro Pro Val Arg Phe Gln Glu Ala Ile Arg
            255                 260                 265 tat gat cgt ccc gcc ata ccg tct ggg agt gag gat tcg aaa cgg tcc          1708
Tyr Asp Arg Pro Ala Ile Pro Ser Gly Ser Glu Asp Ser Lys Arg Ser
        270                 275                 280 aac gac tct aga gga gaa tcg agt gga ccc aat tgg ata gac att gaa          1756
Asn Asp Ser Arg Gly Glu Ser Ser Gly Pro Asn Trp Ile Asp Ile Glu
    285                 290                 295 aat tac act cct aaa aat aat gtg cct att ata ata tct gac gat gac          1804
Asn Tyr Thr Pro Lys Asn Asn Val Pro Ile Ile Ile Ser Asp Asp Asp
300                 305                 310                 315 gtt cct aca gcc cct ccc aag ggc atg aat aat cag tca gta gtg ata          1852
Val Pro Thr Ala Pro Pro Lys Gly Met Asn Asn Gln Ser Val Val Ile
                320                 325                 330 ccc gca atc gta cta agt tgt ctt ata ata gca ctg att cta gga gtg          1900
Pro Ala Ile Val Leu Ser Cys Leu Ile Ile Ala Leu Ile Leu Gly Val
            335                 340                 345 ata tat tat att ttg agg gta aag agg tct cga tca act gca tat caa          1948
Ile Tyr Tyr Ile Leu Arg Val Lys Arg Ser Arg Ser Thr Ala Tyr Gln
        350                 355                 360 caa ctt cct ata ata cat aca act cac cat cct taa gtccacattc              1994
Gln Leu Pro Ile Ile His Thr Thr His His Pro
    365                 370 caatcgagtt ggtagggaag atatgaagtg ggcggtacca accatcataa aataggttgg       2054
agtctggacc aacgttcact cttttgagtg taaaggacca cagcataata cttaatatgt       2114
cgtcgatagc cttcatctat atattgatgg cgattggaac agtttatggg attgtgtatc       2174
gtggagatca tgtaagtctt catgttgata caagctccgg ctttgtaata tatccaacac       2234
tggagaattt tacgatctac ggccatctaa tctttctcga cgaccaacca ttaccagtaa       2294
```

-continued acaattataa tggaaccctc gag                                          2317

<210> SEQ ID NO 4
<211> LENGTH: 21
<212> TYPE: DNA
<213> ORGANISM: Artificial sequence
<220> FEATURE:
<223> OTHER INFORMATION: siRNA

<400> SEQUENCE: 4
ugcuucacca ccuucuugat g                                            21

<210> SEQ ID NO 5
<211> LENGTH: 21
<212> TYPE: DNA
<213> ORGANISM: Artificial sequence
<220> FEATURE:
<223> OTHER INFORMATION: siRNA

<400> SEQUENCE: 5
ugagcuuccc auucagcuct g                                            21

<210> SEQ ID NO 6
<211> LENGTH: 21
<212> TYPE: DNA
<213> ORGANISM: Artificial sequence
<220> FEATURE:
<223> OTHER INFORMATION: siRNA

<400> SEQUENCE: 6
agaagcaggg augauguuct g                                            21

<210> SEQ ID NO 7
<211> LENGTH: 21
<212> TYPE: DNA
<213> ORGANISM: Artificial sequence
<220> FEATURE:
<223> OTHER INFORMATION: siRNA

<400> SEQUENCE: 7
ugaguagcau aucucuucct a                                            21

<210> SEQ ID NO 8
<211> LENGTH: 21
<212> TYPE: DNA
<213> ORGANISM: Artificial sequence
<220> FEATURE:
<223> OTHER INFORMATION: siRNA

<400> SEQUENCE: 8
ggucauagcu ucuggaaaat c                                            21

<210> SEQ ID NO 9
<211> LENGTH: 21
<212> TYPE: DNA
<213> ORGANISM: Artificial sequence
<220> FEATURE:
<223> OTHER INFORMATION: siRNA

<400> SEQUENCE: 9
uuucgacucc uucucuagut g                                            21

<210> SEQ ID NO 10
<211> LENGTH: 21
<212> TYPE: DNA
<213> ORGANISM: Artificial sequence

```
<220> FEATURE:
<223> OTHER INFORMATION: siRNA

<400> SEQUENCE: 10
cuagacucca cguaauguut a                                              21

<210> SEQ ID NO 11
<211> LENGTH: 21
<212> TYPE: DNA
<213> ORGANISM: Artificial sequence
<220> FEATURE:
<223> OTHER INFORMATION: siRNA

<400> SEQUENCE: 11
agacauggga gaagaccaut a                                              21

<210> SEQ ID NO 12
<211> LENGTH: 27
<212> TYPE: RNA
<213> ORGANISM: Artificial sequence
<220> FEATURE:
<223> OTHER INFORMATION: siRNA

<400> SEQUENCE: 12
ugguuauaac ucuucgauau uguccuu                                        27

<210> SEQ ID NO 13
<211> LENGTH: 27
<212> TYPE: RNA
<213> ORGANISM: Artificial sequence
<220> FEATURE:
<223> OTHER INFORMATION: siRNA

<400> SEQUENCE: 13
caucauaauc aaacccaguu caucguc                                        27

<210> SEQ ID NO 14
<211> LENGTH: 27
<212> TYPE: RNA
<213> ORGANISM: Artificial sequence
<220> FEATURE:
<223> OTHER INFORMATION: siRNA

<400> SEQUENCE: 14
uugauguuac auaacguacu ucagcug                                        27

<210> SEQ ID NO 15
<211> LENGTH: 21
<212> TYPE: DNA
<213> ORGANISM: Artificial sequence
<220> FEATURE:
<223> OTHER INFORMATION: siRNA

<400> SEQUENCE: 15
aaucaaaccc aguucaucgt c                                              21

<210> SEQ ID NO 16
<211> LENGTH: 21
<212> TYPE: DNA
<213> ORGANISM: Artificial sequence
<220> FEATURE:
<223> OTHER INFORMATION: siRNA

<400> SEQUENCE: 16
aauaguggua aucacgagct c                                              21
```

```
<210> SEQ ID NO 17
<211> LENGTH: 21
<212> TYPE: DNA
<213> ORGANISM: Artificial sequence
<220> FEATURE:
<223> OTHER INFORMATION: siRNA

<400> SEQUENCE: 17
uuuaugguga gguuguggggt t                                              21

<210> SEQ ID NO 18
<211> LENGTH: 20
<212> TYPE: DNA
<213> ORGANISM: Artificial sequence
<220> FEATURE:
<223> OTHER INFORMATION: primer/probe

<400> SEQUENCE: 18
cggagggaaa atgcttatga                                                 20

<210> SEQ ID NO 19
<211> LENGTH: 20
<212> TYPE: DNA
<213> ORGANISM: Artificial sequence
<220> FEATURE:
<223> OTHER INFORMATION: primer/probe

<400> SEQUENCE: 19
atccattctc tgggatgcac                                                 20

<210> SEQ ID NO 20
<211> LENGTH: 30
<212> TYPE: DNA
<213> ORGANISM: Artificial sequence
<220> FEATURE:
<223> OTHER INFORMATION: primer/probe

<400> SEQUENCE: 20
tcaatacata cgctcgccga ttagtggata                                      30

<210> SEQ ID NO 21
<211> LENGTH: 20
<212> TYPE: DNA
<213> ORGANISM: Artificial sequence
<220> FEATURE:
<223> OTHER INFORMATION: primer/probe

<400> SEQUENCE: 21
attgcctcaa ggacaggatg                                                 20

<210> SEQ ID NO 22
<211> LENGTH: 20
<212> TYPE: DNA
<213> ORGANISM: Artificial sequence
<220> FEATURE:
<223> OTHER INFORMATION: primer/probe

<400> SEQUENCE: 22
caggatcgtt tccaggtgtt                                                 20

<210> SEQ ID NO 23
<211> LENGTH: 30
<212> TYPE: DNA
<213> ORGANISM: Artificial sequence
<220> FEATURE:
<223> OTHER INFORMATION: primer/probe

<400> SEQUENCE: 23
```

-continued ttttcagtag aagcacctct agcacgggat                                    30

<210> SEQ ID NO 24
<211> LENGTH: 24
<212> TYPE: DNA
<213> ORGANISM: Artificial sequence
<220> FEATURE:
<223> OTHER INFORMATION: primer/probe

<400> SEQUENCE: 24
cgctaatagg gaatgtgagc tagg                                          24

<210> SEQ ID NO 25
<211> LENGTH: 24
<212> TYPE: DNA
<213> ORGANISM: Artificial sequence
<220> FEATURE:
<223> OTHER INFORMATION: primer/probe

<400> SEQUENCE: 25
tgtctgaacc tccagtttct ctgg                                          24

<210> SEQ ID NO 26
<211> LENGTH: 30
<212> TYPE: DNA
<213> ORGANISM: Artificial sequence
<220> FEATURE:
<223> OTHER INFORMATION: primer/probe

<400> SEQUENCE: 26
agaccgtcgt gagacaggtt agttttaccc                                    30

<210> SEQ ID NO 27
<211> LENGTH: 19
<212> TYPE: DNA
<213> ORGANISM: Artificial sequence
<220> FEATURE:
<223> OTHER INFORMATION: primer/probe

<400> SEQUENCE: 27
gctgcccaga acatcatcc                                                19

<210> SEQ ID NO 28
<211> LENGTH: 20
<212> TYPE: DNA
<213> ORGANISM: Artificial sequence
<220> FEATURE:
<223> OTHER INFORMATION: primer/probe

<400> SEQUENCE: 28
gtcagatcca cgacggacac                                               20

<210> SEQ ID NO 29
<211> LENGTH: 20
<212> TYPE: DNA
<213> ORGANISM: Artificial sequence
<220> FEATURE:
<223> OTHER INFORMATION: primer/probe

<400> SEQUENCE: 29
tcactggcat ggccttccgt                                               20

<210> SEQ ID NO 30
<211> LENGTH: 20
<212> TYPE: DNA
<213> ORGANISM: Artificial sequence

```
<220> FEATURE:
<223> OTHER INFORMATION: primer/probe

<400> SEQUENCE: 30
ccttgatgga gctcgtgatt                                              20

<210> SEQ ID NO 31
<211> LENGTH: 20
<212> TYPE: DNA
<213> ORGANISM: Artificial sequence
<220> FEATURE:
<223> OTHER INFORMATION: primer/probe

<400> SEQUENCE: 31
tcgaatcctc actcccagac                                              20

<210> SEQ ID NO 32
<211> LENGTH: 30
<212> TYPE: DNA
<213> ORGANISM: Artificial sequence
<220> FEATURE:
<223> OTHER INFORMATION: primer/probe

<400> SEQUENCE: 32
accctataac ccacaacctc accataaagc                                   30

<210> SEQ ID NO 33
<211> LENGTH: 20
<212> TYPE: DNA
<213> ORGANISM: Artificial sequence
<220> FEATURE:
<223> OTHER INFORMATION: primer/probe

<400> SEQUENCE: 33
attgcctcaa ggacaggatg                                              20

<210> SEQ ID NO 34
<211> LENGTH: 20
<212> TYPE: DNA
<213> ORGANISM: Artificial sequence
<220> FEATURE:
<223> OTHER INFORMATION: primer/probe

<400> SEQUENCE: 34
caggatcgtt tccaggtgtt                                              20

<210> SEQ ID NO 35
<211> LENGTH: 30
<212> TYPE: DNA
<213> ORGANISM: Artificial sequence
<220> FEATURE:
<223> OTHER INFORMATION: primer/probe

<400> SEQUENCE: 35
ttttcagtag aagcacctct agcacgggat                                   30

<210> SEQ ID NO 36
<211> LENGTH: 24
<212> TYPE: DNA
<213> ORGANISM: Artificial sequence
<220> FEATURE:
<223> OTHER INFORMATION: primer/probe

<400> SEQUENCE: 36
cgctaatagg gaatgtgagc tagg                                         24
```

-continued

```
<210> SEQ ID NO 37
<211> LENGTH: 24
<212> TYPE: DNA
<213> ORGANISM: Artificial sequence
<220> FEATURE:
<223> OTHER INFORMATION: primer/probe

<400> SEQUENCE: 37
tgtctgaacc tccagtttct ctgg                                          24

<210> SEQ ID NO 38
<211> LENGTH: 30
<212> TYPE: DNA
<213> ORGANISM: Artificial sequence
<220> FEATURE:
<223> OTHER INFORMATION: primer/probe

<400> SEQUENCE: 38
agaccgtcgt gagacaggtt agttttaccc                                    30

<210> SEQ ID NO 39
<211> LENGTH: 4848
<212> TYPE: DNA
<213> ORGANISM: Felid herpesvirus 1
<220> FEATURE:
<221> NAME/KEY: exon
<222> LOCATION: (518)..(4051)

<400> SEQUENCE: 39
gcatgcaagc ttgtaagata tcccatgtcc actgagacca gaggttttcg atccagacaa    60
cacggctacg ttatgaataa atccagtctc tacagtgaga ccttgaatca gaggaacaac   120
cgctaaatca gagtctgaac tccgagccga tagaatcccc aattctggaa tctgcaggga   180
atcacttctg catgcataga tgtaaccgag tggaccggct tgaagtgaga tggtctttgg   240
ggcagattcc attgtaggta ttatcctatt aagtctcgat gagaagctat ctctacaccg   300
taatttgtac ctggtgtaaa ctaagacgaa tgagtggata taccaaatac ctgggtatga   360
gttatactta agtgtgtgaa tgtccccgcc cacacaggtc acatgtaggt agtaggtttt   420
gtgtaaaagg atattaattt cccatctaga tacacatcga aacttttttc ttatctgggc   480
tcgtctataa tttacctccg atcaacggcg tcgagct atg aga aat ggg gag gat   535
                                       Met Arg Asn Gly Glu Asp
                                         1               5 cga aac atg cta tct aat cga ggt ggt ttt ttc aac cca ttc cta ttc   583
Arg Asn Met Leu Ser Asn Arg Gly Gly Phe Phe Asn Pro Phe Leu Phe
         10                  15                  20 aga ggg gcc tgt gga gac tcc tcc aga cta cct aaa aat gaa tcg atg   631
Arg Gly Ala Cys Gly Asp Ser Ser Arg Leu Pro Lys Asn Glu Ser Met
     25                  30                  35 cga tat aat gga tat aga cct acg tat tat aca gat ctg gct gaa ttt   679
Arg Tyr Asn Gly Tyr Arg Pro Thr Tyr Tyr Thr Asp Leu Ala Glu Phe
 40                  45                  50 aag ttt ata gct ccc cgc tgt ctt gat gaa aat cta cat cct gac caa   727
Lys Phe Ile Ala Pro Arg Cys Leu Asp Glu Asn Leu His Pro Asp Gln
55                  60                  65                  70 cgc aag ggg atg cat ata gga acc ctc tcc aga caa ccg aag gta tat   775
Arg Lys Gly Met His Ile Gly Thr Leu Ser Arg Gln Pro Lys Val Tyr
                 75                  80                  85 cgc gag gga caa gaa tat aac ata ttt gat ttt aat gat agc aca gaa   823
Arg Glu Gly Gln Glu Tyr Asn Ile Phe Asp Phe Asn Asp Ser Thr Glu
             90                  95                 100 cta cca tgg cct aga cgc ata tat aca tgg gag caa aaa tcc tta ctc   871
Leu Pro Trp Pro Arg Arg Ile Tyr Thr Trp Glu Gln Lys Ser Leu Leu
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 105 |     |     |     |     | 110 |     |     |     |     | 115 |     |     |      |
| cca | ccc | aac | ttc | gat | ttt | aga | ttt | gat | cgt | ttt | cat | gta | tac | gat | att | 919  |
| Pro | Pro | Asn | Phe | Asp | Phe | Arg | Phe | Asp | Arg | Phe | His | Val | Tyr | Asp | Ile |      |
|     | 120 |     |     |     |     | 125 |     |     |     |     | 130 |     |     |     |     |      |
| atc | gaa | aat | att | gaa | ata | gct | aca | ggg | gat | gat | tct | tcg | cgt | ttt | gca | 967  |
| Ile | Glu | Asn | Ile | Glu | Ile | Ala | Thr | Gly | Asp | Asp | Ser | Ser | Arg | Phe | Ala |      |
| 135 |     |     |     |     | 140 |     |     |     |     | 145 |     |     |     |     | 150 |      |
| aac | ttt | ata | cgt | ccc | aat | gga | agt | gtt | ata | acg | tta | ttg | ggt | ctt | agt | 1015 |
| Asn | Phe | Ile | Arg | Pro | Asn | Gly | Ser | Val | Ile | Thr | Leu | Leu | Gly | Leu | Ser |      |
|     |     |     |     | 155 |     |     |     |     | 160 |     |     |     |     | 165 |     |      |
| gcg | tgt | ggt | aaa | agg | gta | gcc | gtg | cat | gta | tat | gga | gtg | aat | cca | tat | 1063 |
| Ala | Cys | Gly | Lys | Arg | Val | Ala | Val | His | Val | Tyr | Gly | Val | Asn | Pro | Tyr |      |
|     |     |     | 170 |     |     |     |     | 175 |     |     |     |     | 180 |     |     |      |
| ttt | tac | atg | gat | aag | gat | cta | gtg | gat | agg | gtg | tgt | aat | att | tct | aat | 1111 |
| Phe | Tyr | Met | Asp | Lys | Asp | Leu | Val | Asp | Arg | Val | Cys | Asn | Ile | Ser | Asn |      |
|     |     |     |     | 185 |     |     |     |     | 190 |     |     |     |     | 195 |     |      |
| aat | caa | caa | ttg | gtg | tcg | ctc | atg | gtc | gag | tcc | att | aaa | aat | tca | tat | 1159 |
| Asn | Gln | Gln | Leu | Val | Ser | Leu | Met | Val | Glu | Ser | Ile | Lys | Asn | Ser | Tyr |      |
|     | 200 |     |     |     |     | 205 |     |     |     |     | 210 |     |     |     |     |      |
| ata | aat | aat | ggg | gtg | ggg | ggt | aaa | cat | tcg | ggg | gat | cgt | gga | ttg | aat | 1207 |
| Ile | Asn | Asn | Gly | Val | Gly | Gly | Lys | His | Ser | Gly | Asp | Arg | Gly | Leu | Asn |      |
| 215 |     |     |     |     | 220 |     |     |     |     | 225 |     |     |     |     | 230 |      |
| atg | aaa | att | tcc | caa | gaa | tgt | ttc | aag | ata | aac | gtg | gtt | tat | gcg | acc | 1255 |
| Met | Lys | Ile | Ser | Gln | Glu | Cys | Phe | Lys | Ile | Asn | Val | Val | Tyr | Ala | Thr |      |
|     |     |     |     | 235 |     |     |     |     | 240 |     |     |     |     | 245 |     |      |
| aat | att | tat | ttt | ttt | cac | tca | cga | ccc | aag | tta | tat | tat | aaa | att | act | 1303 |
| Asn | Ile | Tyr | Phe | Phe | His | Ser | Arg | Pro | Lys | Leu | Tyr | Tyr | Lys | Ile | Thr |      |
|     |     |     | 250 |     |     |     |     | 255 |     |     |     |     | 260 |     |     |      |
| acc | ggt | agc | agt | cga | tta | tgt | gga | tat | att | tgt | gat | aat | ttt | cat | cct | 1351 |
| Thr | Gly | Ser | Ser | Arg | Leu | Cys | Gly | Tyr | Ile | Cys | Asp | Asn | Phe | His | Pro |      |
|     |     | 265 |     |     |     |     | 270 |     |     |     |     | 275 |     |     |     |      |
| gaa | att | aca | aaa | tat | gaa | ggg | aac | gtt | gat | gta | ata | tcc | agg | ttc | ata | 1399 |
| Glu | Ile | Thr | Lys | Tyr | Glu | Gly | Asn | Val | Asp | Val | Ile | Ser | Arg | Phe | Ile |      |
| 280 |     |     |     |     | 285 |     |     |     |     | 290 |     |     |     |     |     |      |
| tta | gat | aat | gct | gga | ttt | ata | acc | ttt | gga | tgg | tat | agg | tta | cgc | cct | 1447 |
| Leu | Asp | Asn | Ala | Gly | Phe | Ile | Thr | Phe | Gly | Trp | Tyr | Arg | Leu | Arg | Pro |      |
| 295 |     |     |     | 300 |     |     |     |     | 305 |     |     |     |     | 310 |     |      |
| gga | gca | aac | ggg | gag | cgg | gtt | caa | ttc | cga | tca | atc | gat | aaa | tac | ttg | 1495 |
| Gly | Ala | Asn | Gly | Glu | Arg | Val | Gln | Phe | Arg | Ser | Ile | Asp | Lys | Tyr | Leu |      |
|     |     |     |     | 315 |     |     |     |     | 320 |     |     |     |     | 325 |     |      |
| acg | tca | agt | gat | gtt | gag | ata | aat | tgt | aca | gtt | gac | aat | tta | gag | gca | 1543 |
| Thr | Ser | Ser | Asp | Val | Glu | Ile | Asn | Cys | Thr | Val | Asp | Asn | Leu | Glu | Ala |      |
|     |     |     | 330 |     |     |     |     | 335 |     |     |     |     | 340 |     |     |      |
| tta | cca | aac | gat | gat | aca | tgg | cca | gac | tac | aaa | tta | cta | tgt | ttt | gat | 1591 |
| Leu | Pro | Asn | Asp | Asp | Thr | Trp | Pro | Asp | Tyr | Lys | Leu | Leu | Cys | Phe | Asp |      |
|     |     | 345 |     |     |     |     | 350 |     |     |     |     | 355 |     |     |     |      |
| ata | gag | tgt | aaa | gcc | gga | act | ggt | act | gaa | tta | gca | ttt | cct | gtc | gct | 1639 |
| Ile | Glu | Cys | Lys | Ala | Gly | Thr | Gly | Thr | Glu | Leu | Ala | Phe | Pro | Val | Ala |      |
| 360 |     |     |     |     | 365 |     |     |     |     | 370 |     |     |     |     |     |      |
| aca | aac | caa | gat | gac | gtt | gtc | att | caa | att | tca | tgt | ttg | ata | tat | tca | 1687 |
| Thr | Asn | Gln | Asp | Asp | Val | Val | Ile | Gln | Ile | Ser | Cys | Leu | Ile | Tyr | Ser |      |
| 375 |     |     |     | 380 |     |     |     |     | 385 |     |     |     |     | 390 |     |      |
| ttg | gcc | act | cgt | aaa | cac | gaa | ctc | acg | cta | cta | ttt | tct | ctg | ggt | tcc | 1735 |
| Leu | Ala | Thr | Arg | Lys | His | Glu | Leu | Thr | Leu | Leu | Phe | Ser | Leu | Gly | Ser |      |
|     |     |     | 395 |     |     |     |     | 400 |     |     |     |     | 405 |     |     |      |
| tgt | gat | cta | cca | gac | agc | tgt | ctg | ctc | gga | agt | act | gaa | agg | ggg | gag | 1783 |
| Cys | Asp | Leu | Pro | Asp | Ser | Cys | Leu | Leu | Gly | Ser | Thr | Glu | Arg | Gly | Glu |      |
|     |     |     | 410 |     |     |     |     | 415 |     |     |     |     | 420 |     |     |      |
| ccg | acg | ccc | atc | att | tta | gaa | ttc | gat | agc | gag | ttt | gaa | atg | ctt | ata | 1831 |
| Pro | Thr | Pro | Ile | Ile | Leu | Glu | Phe | Asp | Ser | Glu | Phe | Glu | Met | Leu | Ile |      |

```
                    425                 430                 435
gca ttc cta acc ttt ata aaa caa tac tcc cct gag ttt gct aca ggt    1879
Ala Phe Leu Thr Phe Ile Lys Gln Tyr Ser Pro Glu Phe Ala Thr Gly
    440                 445                 450 tat aat att gtc aat ttc gat tgg gcc tat atc atc gag aaa cta aaa    1927
Tyr Asn Ile Val Asn Phe Asp Trp Ala Tyr Ile Ile Glu Lys Leu Lys
455                 460                 465                 470 tcg gta tac aat att cgc ttg gat gga tat gga aaa ttt aat cga ggt    1975
Ser Val Tyr Asn Ile Arg Leu Asp Gly Tyr Gly Lys Phe Asn Arg Gly
            475                 480                 485 gga tta ttc aaa gtc tgg gat atg ggc cga gta aat ttt caa aaa cgg    2023
Gly Leu Phe Lys Val Trp Asp Met Gly Arg Val Asn Phe Gln Lys Arg
        490                 495                 500 agc aag gtc aag att aat ggt ctt gtg aca ctt gat atg tac acc gtc    2071
Ser Lys Val Lys Ile Asn Gly Leu Val Thr Leu Asp Met Tyr Thr Val
        505                 510                 515 gcc aca gag aaa ctt cgt tta tct agc tat aaa tta aac gcc gtc gcg    2119
Ala Thr Glu Lys Leu Arg Leu Ser Ser Tyr Lys Leu Asn Ala Val Ala
    520                 525                 530 gag gag gcc tta ggg gag tat aaa ata gac ctc ccc tat aaa gaa att    2167
Glu Glu Ala Leu Gly Glu Tyr Lys Ile Asp Leu Pro Tyr Lys Glu Ile
535                 540                 545                 550 cca cgc tat tac gcg agc ggt gcc agg caa cgg gga ata ata ggt gaa    2215
Pro Arg Tyr Tyr Ala Ser Gly Ala Arg Gln Arg Gly Ile Ile Gly Glu
            555                 560                 565 tat tgt atc caa gat tct cta ctc gtg ggg aag ttg ttt ttc aaa tat    2263
Tyr Cys Ile Gln Asp Ser Leu Leu Val Gly Lys Leu Phe Phe Lys Tyr
        570                 575                 580 ctc cca cat ctg gag cta tct gct ata gcg aaa tta gca aat ata act    2311
Leu Pro His Leu Glu Leu Ser Ala Ile Ala Lys Leu Ala Asn Ile Thr
        585                 590                 595 ctg aca cgt gcc atc ttc gac ggg caa caa atc cgg gta tac acg tgt    2359
Leu Thr Arg Ala Ile Phe Asp Gly Gln Gln Ile Arg Val Tyr Thr Cys
    600                 605                 610 ctc cta aaa tta gcc aga gac aga aat ttc atc cta cct gat aac cgc    2407
Leu Leu Lys Leu Ala Arg Asp Arg Asn Phe Ile Leu Pro Asp Asn Arg
615                 620                 625                 630 aac cgt ttc tgt gga gac ccg aat ata ccc tca gag gac ata gaa aat    2455
Asn Arg Phe Cys Gly Asp Pro Asn Ile Pro Ser Glu Asp Ile Glu Asn
            635                 640                 645 ata aac aca tgt gac agc atg gaa ggt gat tac aca gag gaa ttc gat    2503
Ile Asn Thr Cys Asp Ser Met Glu Gly Asp Tyr Thr Glu Glu Phe Asp
        650                 655                 660 cag cag tca tct acc gta gcc gag tgt gtg gct cct acc cca tct caa    2551
Gln Gln Ser Ser Thr Val Ala Glu Cys Val Ala Pro Thr Pro Ser Gln
        665                 670                 675 gcg aca tcg cgt tct gtt gga tat caa ggg gcc aag gtt cta gac cca    2599
Ala Thr Ser Arg Ser Val Gly Tyr Gln Gly Ala Lys Val Leu Asp Pro
    680                 685                 690 atc tcc gga ttt cat ata gac cca gta gtt gta ttg gat ttt gcc agc    2647
Ile Ser Gly Phe His Ile Asp Pro Val Val Val Leu Asp Phe Ala Ser
695                 700                 705                 710 ctc tac cca agt att atc cag gcc cat aat cta tgt ttc acg act ctt    2695
Leu Tyr Pro Ser Ile Ile Gln Ala His Asn Leu Cys Phe Thr Thr Leu
            715                 720                 725 acc aca gaa cgt caa tct ctc gaa acc ctc cga cca gga ata gat ttt    2743
Thr Thr Glu Arg Gln Ser Leu Glu Thr Leu Arg Pro Gly Ile Asp Phe
        730                 735                 740 tcg gaa ttt gat gtc ggt gga cat aaa tta tat ttt gta gat tct cat    2791
Ser Glu Phe Asp Val Gly Gly His Lys Leu Tyr Phe Val Asp Ser His
```

|     |     |     |     |     |     |     |     |     |     |     |     |     |     |     |     |
| --- | --- | --- | --- | --- | --- | --- | --- | --- | --- | --- | --- | --- | --- | --- | --- |
|     |     | 745 |     |     |     | 750 |     |     |     | 755 |     |     |     |     |     |
| gtt | cga | gaa | gag | cct | gct | ggt | gtt | tta | ctt | cgc | gat | tgg | ctt | gcc | atg | 2839 |
| Val | Arg | Glu | Glu | Pro | Ala | Gly | Val | Leu | Leu | Arg | Asp | Trp | Leu | Ala | Met |
|     | 760 |     |     |     |     | 765 |     |     |     | 770 |     |     |     |     |     |
| aga | aag | gcc | atc | cgg | gcc | cgt | att | ccc | gat | agc | aca | tca | gac | gag | gcg | 2887 |
| Arg | Lys | Ala | Ile | Arg | Ala | Arg | Ile | Pro | Asp | Ser | Thr | Ser | Asp | Glu | Ala |
| 775 |     |     |     |     | 780 |     |     |     |     | 785 |     |     |     |     | 790 |
| att | tta | ctg | gat | aaa | caa | caa | gct | gcc | ata | aag | gta | gta | tgt | aac | tcc | 2935 |
| Ile | Leu | Leu | Asp | Lys | Gln | Gln | Ala | Ala | Ile | Lys | Val | Val | Cys | Asn | Ser |
|     |     |     |     |     | 795 |     |     |     |     | 800 |     |     |     |     | 805 |
| gta | tat | gga | ttt | gcc | ggg | gtg | gct | aat | ggt | ctt | ctc | cca | tgt | cta | cag | 2983 |
| Val | Tyr | Gly | Phe | Ala | Gly | Val | Ala | Asn | Gly | Leu | Leu | Pro | Cys | Leu | Gln |
|     |     |     | 810 |     |     |     |     | 815 |     |     |     |     | 820 |     |     |
| ata | gcc | gcc | act | gta | act | acg | ata | gga | aga | gat | atg | cta | ctc | aat | act | 3031 |
| Ile | Ala | Ala | Thr | Val | Thr | Thr | Ile | Gly | Arg | Asp | Met | Leu | Leu | Asn | Thr |
|     |     | 825 |     |     |     |     | 830 |     |     |     |     | 835 |     |     |     |
| aaa | cat | tac | gtg | gag | tct | aga | tgg | gca | act | aga | gaa | gga | gtc | gaa | agt | 3079 |
| Lys | His | Tyr | Val | Glu | Ser | Arg | Trp | Ala | Thr | Arg | Glu | Gly | Val | Glu | Ser |
|     | 840 |     |     |     |     | 845 |     |     |     |     | 850 |     |     |     |     |
| gat | ttt | cca | gaa | gct | atg | acc | gtt | act | att | ccg | gat | aaa | ccc | tat | aat | 3127 |
| Asp | Phe | Pro | Glu | Ala | Met | Thr | Val | Thr | Ile | Pro | Asp | Lys | Pro | Tyr | Asn |
| 855 |     |     |     |     | 860 |     |     |     |     | 865 |     |     |     |     | 870 |
| gta | cag | gta | atc | tac | ggt | gat | aca | gat | tcc | gta | ttt | att | aag | ttt | aga | 3175 |
| Val | Gln | Val | Ile | Tyr | Gly | Asp | Thr | Asp | Ser | Val | Phe | Ile | Lys | Phe | Arg |
|     |     |     |     | 875 |     |     |     |     | 880 |     |     |     |     | 885 |     |
| ggc | ttc | acg | tat | gat | gga | gta | acg | aga | tta | ggt | gat | ctc | atg | gcc | aag | 3223 |
| Gly | Phe | Thr | Tyr | Asp | Gly | Val | Thr | Arg | Leu | Gly | Asp | Leu | Met | Ala | Lys |
|     |     |     | 890 |     |     |     |     | 895 |     |     |     |     | 900 |     |     |
| caa | att | tca | caa | gcc | ctg | ttc | aga | gct | cca | atc | aaa | ctc | gaa | tgt | gaa | 3271 |
| Gln | Ile | Ser | Gln | Ala | Leu | Phe | Arg | Ala | Pro | Ile | Lys | Leu | Glu | Cys | Glu |
|     |     | 905 |     |     |     |     | 910 |     |     |     |     | 915 |     |     |     |
| aaa | act | ttc | tgt | aaa | tta | ata | ttg | ata | aca | aag | aag | aaa | tac | atc | ggt | 3319 |
| Lys | Thr | Phe | Cys | Lys | Leu | Ile | Leu | Ile | Thr | Lys | Lys | Lys | Tyr | Ile | Gly |
|     | 920 |     |     |     |     | 925 |     |     |     |     | 930 |     |     |     |     |
| gtg | atc | aac | gga | ggg | aaa | atg | ctt | atg | aag | ggt | gtc | gac | ctt | gtt | cgt | 3367 |
| Val | Ile | Asn | Gly | Gly | Lys | Met | Leu | Met | Lys | Gly | Val | Asp | Leu | Val | Arg |
| 935 |     |     |     |     | 940 |     |     |     |     | 945 |     |     |     |     | 950 |
| aag | aat | aac | tgt | aat | ttt | atc | aat | aca | tac | gct | cgc | cga | tta | gtg | gat | 3415 |
| Lys | Asn | Asn | Cys | Asn | Phe | Ile | Asn | Thr | Tyr | Ala | Arg | Arg | Leu | Val | Asp |
|     |     |     |     | 955 |     |     |     |     | 960 |     |     |     |     | 965 |     |
| ata | tta | tta | tat | aat | gat | aca | gtt | tcc | gag | gca | gcc | gca | gaa | atc | gca | 3463 |
| Ile | Leu | Leu | Tyr | Asn | Asp | Thr | Val | Ser | Glu | Ala | Ala | Ala | Glu | Ile | Ala |
|     |     |     | 970 |     |     |     |     | 975 |     |     |     |     | 980 |     |     |
| agc | gtg | cat | ccc | aga | gaa | tgg | atg | gga | cgt | gcg | ttg | cct | gcc | aac | ttt | 3511 |
| Ser | Val | His | Pro | Arg | Glu | Trp | Met | Gly | Arg | Ala | Leu | Pro | Ala | Asn | Phe |
|     |     | 985 |     |     |     |     | 990 |     |     |     |     | 995 |     |     |     |
| tgg | gaa | ttt | gga | agg | gta | ctg | gct | gaa | gca | tat | act | cat | ata | acc |     | 3556 |
| Trp | Glu | Phe | Gly | Arg | Val | Leu | Ala | Glu | Ala | Tyr | Thr | His | Ile | Thr |     |
| 1000 |     |     |     |     | 1005 |     |     |     |     | 1010 |     |     |     |     |     |
| gct | cca | gat | ctc | gat | gtg | aac | gat | ttt | gtt | atg | acc | gcg | gaa | ctc |     | 3601 |
| Ala | Pro | Asp | Leu | Asp | Val | Asn | Asp | Phe | Val | Met | Thr | Ala | Glu | Leu |     |
|     | 1015 |     |     |     |     | 1020 |     |     |     |     | 1025 |     |     |     |     |
| agc | cgt | cca | cct | gat | gca | tat | atc | aat | aaa | agg | att | gcc | cat | ctc |     | 3646 |
| Ser | Arg | Pro | Pro | Asp | Ala | Tyr | Ile | Asn | Lys | Arg | Ile | Ala | His | Leu |     |
|     | 1030 |     |     |     |     | 1035 |     |     |     |     | 1040 |     |     |     |     |
| acg | gtg | tac | tat | aaa | ttg | gtt | atg | cgt | aac | gag | gaa | gtg | cct | agt |     | 3691 |
| Thr | Val | Tyr | Tyr | Lys | Leu | Val | Met | Arg | Asn | Glu | Glu | Val | Pro | Ser |     |
|     | 1045 |     |     |     |     | 1050 |     |     |     |     | 1055 |     |     |     |     |
| gtg | aaa | gaa | cgt | ata | cca | tat | gta | att | ata | tca | cca | gcg | cag | gtg |     | 3736 |
| Val | Lys | Glu | Arg | Ile | Pro | Tyr | Val | Ile | Ile | Ser | Pro | Ala | Gln | Val |     |

| | | | | | | | | | | | | |
|---|---|---|---|---|---|---|---|---|---|---|---|---|
| | | | | 1060 | | | | 1065 | | | 1070 | |
| tcg | gac | agt | gac | ctg | ctt | gga | gtc | gat | ggg | ttg | cgc | ggg act ata | 3781 |
| Ser | Asp | Ser | Asp | Leu | Leu | Gly | Val | Asp | Gly | Leu | Arg | Gly Thr Ile |
| | 1075 | | | | | 1080 | | | | | 1085 | |
| atc | aat | aag | gcc | ctc | aac | aat | acc | aaa | aaa | aga | aaa | ttg ctc gtg | 3826 |
| Ile | Asn | Lys | Ala | Leu | Asn | Asn | Thr | Lys | Lys | Arg | Lys | Leu Leu Val |
| | 1090 | | | | | 1095 | | | | | 1100 | |
| tcg | gat | ctt | gct | gaa | gac | cca | tcc | tat | gta | ata | gct | aat ggc ata | 3871 |
| Ser | Asp | Leu | Ala | Glu | Asp | Pro | Ser | Tyr | Val | Ile | Ala | Asn Gly Ile |
| | 1105 | | | | | 1110 | | | | | 1115 | |
| cac | ctg | aat | aca | gaa | tat | tac | ttt | tca | cat | ctt | tta | agt acg att | 3916 |
| His | Leu | Asn | Thr | Glu | Tyr | Tyr | Phe | Ser | His | Leu | Leu | Ser Thr Ile |
| | 1120 | | | | | 1125 | | | | | 1130 | |
| agc | gtt | aca | ttt | aaa | gct | ttg | ttt | gga | aat | gat | gtc | aaa aca act | 3961 |
| Ser | Val | Thr | Phe | Lys | Ala | Leu | Phe | Gly | Asn | Asp | Val | Lys Thr Thr |
| | 1135 | | | | | 1140 | | | | | 1145 | |
| gaa | ata | ctt | ctc | aag | agg | ttt | att | ccg | gaa | aca | tca | ata gta gac | 4006 |
| Glu | Ile | Leu | Leu | Lys | Arg | Phe | Ile | Pro | Glu | Thr | Ser | Ile Val Asp |
| | 1150 | | | | | 1155 | | | | | 1160 | |
| agc | gga | tac | aaa | cca | agt | tat | ctg | aat | atg | ggt | ttg | agg cat tga | 4051 |
| Ser | Gly | Tyr | Lys | Pro | Ser | Tyr | Leu | Asn | Met | Gly | Leu | Arg His |
| | 1165 | | | | | 1170 | | | | | 1175 | |

| | |
|---|---|
| tcgagaacta gcggggtgga ggaaactcgt cgaatagtga ataaagtttt ctgtattcca | 4111 |
| agagcaactc tccatcaaag ctaaggtccc tcatcttaac aataaatatc agttgcactc | 4171 |
| acggttggta tactccatat gccgtctgtc tttcaccatg ctcggcgaac caccaatata | 4231 |
| aacatagttt gccacacatg tgcgataatc ctatacccgt gacgagcaga taatagtctg | 4291 |
| tccaataaac gatggtgaag gtgtacggtc ttacctggga ataccacata catcatatac | 4351 |
| cccgaaaatt cgagaggtcg cgatagaata gaactttaaa gttttgtggt ccccatctc | 4411 |
| ttagaacatg atatacaaaa aacaattctg gttgactgag aacatcttct aaaaatctct | 4471 |
| ccgctgaacc tgtatttgtg tggatgtact accaccgatg tggttagcga gggagatgat | 4531 |
| tgatgccaca aatactctat attcgtatat gttatttaat tgttggacat aggctaaaac | 4591 |
| taaagccgcc cggctagtgt gatatagacg aggttctccg gagacggcac atgttggaca | 4651 |
| atagccacct atccctagat gatatcccat ggcagatagc gatacacagt tatcggcaac | 4711 |
| tgtctgattg agatcgagcg gtaatgatat tggcgtagtt tttactatag gaacaaccaa | 4771 |
| gtctcgtacg gccgcgagtt catctgatgg agaaaccgat acataatcca aaatatagac | 4831 |
| tataacgccc tctttct | 4848 |